US008846363B2

(12) United States Patent
Myette et al.

(10) Patent No.: US 8,846,363 B2
(45) Date of Patent: Sep. 30, 2014

(54) COMPOSITIONS OF AND METHODS OF USING SULFATASES FROM *FLAVOBACTERIUM HEPARINUM*

(76) Inventors: James R. Myette, Waltham, MA (US); Ram Sasisekharan, Bedford, MA (US)

(*) Notice: Subject to any disclaimer, the term of this patent is extended or adjusted under 35 U.S.C. 154(b) by 1013 days.

(21) Appl. No.: 12/910,767

(22) Filed: Oct. 22, 2010

(65) Prior Publication Data
US 2011/0033901 A1 Feb. 10, 2011

Related U.S. Application Data

(62) Division of application No. 12/006,794, filed on Jan. 4, 2008, now Pat. No. 7,842,492.

(60) Provisional application No. 60/879,272, filed on Jan. 5, 2007.

(51) Int. Cl.
*C12N 9/16* (2006.01)
*G01N 33/50* (2006.01)
*C12Q 1/34* (2006.01)
*A61K 38/00* (2006.01)

(52) U.S. Cl.
CPC .............. *C12Q 1/34* (2013.01); *G01N 33/5011* (2013.01); *A61K 38/00* (2013.01); *C12N 9/16* (2013.01); *G01N 2400/40* (2013.01)
USPC ....................... 435/196; 435/252.3; 435/320.1

(58) Field of Classification Search
CPC .............. C12N 9/16; C12Q 1/34; A61K 38/00
USPC ................................................. 435/18, 193
See application file for complete search history.

(56) References Cited

U.S. PATENT DOCUMENTS

| | | | |
|---|---|---|---|
| 5,198,355 A | 3/1993 | Kikuchi et al. | |
| 5,254,801 A | 10/1993 | Dotson et al. | |
| 5,798,239 A | 8/1998 | Wilson et al. | |
| 5,932,211 A | 8/1999 | Wilson et al. | |
| 5,935,850 A | 8/1999 | Clark et al. | |
| 6,153,188 A | 11/2000 | Wilson et al. | |
| 6,217,863 B1 | 4/2001 | Godavarti et al. | |
| 6,597,996 B1 | 7/2003 | Venkataraman et al. | |
| 6,869,789 B2 | 3/2005 | Liu et al. | |
| 6,962,699 B2 | 11/2005 | Pojasek et al. | |
| 7,056,504 B1 | 6/2006 | Sasisekharan et al. | |
| 7,083,937 B2 | 8/2006 | Sasisekharan et al. | |
| 7,090,973 B1 | 8/2006 | Breton | |
| 7,105,334 B2 | 9/2006 | Pojasek et al. | |
| 7,110,889 B2 | 9/2006 | Venkataraman et al. | |
| 7,117,100 B2 | 10/2006 | Venkataraman et al. | |
| 7,129,335 B2 | 10/2006 | Pojasek et al. | |
| 7,139,666 B2 | 11/2006 | Venkataraman | |
| 7,150,981 B2 | 12/2006 | Habuchi et al. | |
| 7,247,445 B2 | 7/2007 | Sasisekharan et al. | |
| 7,270,815 B2 | 9/2007 | Sasisekharan et al. | |
| 7,390,633 B2 | 6/2008 | Liu et al. | |
| 7,396,824 B2 | 7/2008 | Sasisekharan et al. | |
| 7,399,604 B2 | 7/2008 | Sasisekharan et al. | |
| 7,412,332 B1 | 8/2008 | Venkataraman et al. | |
| 7,429,474 B2 * | 9/2008 | Sasisekharan et al. | ....... 435/196 |
| 7,455,986 B2 | 11/2008 | Liu et al. | |
| 7,476,730 B2 | 1/2009 | Habuchi et al. | |
| 7,504,247 B2 | 3/2009 | Sasisekharan et al. | |
| 7,507,570 B2 | 3/2009 | Prabhakar et al. | |
| 7,508,206 B2 | 3/2009 | Sasisekharan et al. | |
| 7,553,950 B2 | 6/2009 | Prabhakar et al. | |
| 7,560,106 B2 | 7/2009 | Sasisekharan et al. | |
| 7,585,642 B2 | 9/2009 | Sasiskeharan et al. | |
| 7,592,152 B2 | 9/2009 | Prabhakar et al. | |
| 2002/0122793 A1 | 9/2002 | Liu et al. | |
| 2002/0128225 A1 | 9/2002 | Liu et al. | |
| 2002/0169143 A1 | 11/2002 | Sasisekharan et al. | |
| 2003/0008820 A1 | 1/2003 | Kwan et al. | |
| 2003/0099628 A1 | 5/2003 | Liu et al. | |
| 2003/0147875 A1 | 8/2003 | Rosen et al. | |
| 2003/0191587 A1 | 10/2003 | Venkataraman et al. | |
| 2004/0091471 A1 | 5/2004 | Myette et al. | |
| 2004/0091472 A1 | 5/2004 | Pojasek et al. | |
| 2004/0092037 A1 | 5/2004 | Sasisekharan et al. | |
| 2004/0197933 A1 | 10/2004 | Venkataraman et al. | |
| 2004/0204869 A1 | 10/2004 | Venkataraman et al. | |
| 2005/0037376 A1 | 2/2005 | Sasisekharan et al. | |
| 2005/0214276 A9 | 9/2005 | Myette et al. | |
| 2005/0227320 A1 | 10/2005 | Pojasek et al. | |
| 2005/0233402 A1 | 10/2005 | Liu et al. | |
| 2005/0233419 A1 | 10/2005 | Pojasek et al. | |
| 2006/0024664 A1 | 2/2006 | Sasisekharan et al. | |
| 2006/0057638 A1 | 3/2006 | Bosques et al. | |
| 2006/0067927 A1 | 3/2006 | Chandrasekaran et al. | |
| 2006/0067928 A1 | 3/2006 | Liu et al. | |
| 2006/0078959 A1 | 4/2006 | Prabhakar et al. | |
| 2006/0083711 A1 | 4/2006 | Berry et al. | |
| 2006/0105430 A1 | 5/2006 | Sasisekharan et al. | |
| 2006/0127950 A1 | 6/2006 | Bosques et al. | |
| 2006/0154894 A1 | 7/2006 | Berry et al. | |
| 2006/0177885 A1 | 8/2006 | Myette et al. | |
| 2006/0177910 A1 | 8/2006 | Myette et al. | |
| 2006/0177911 A1 | 8/2006 | Myette et al. | |
| 2006/0182734 A1 | 8/2006 | Liu et al. | |
| 2006/0183713 A1 | 8/2006 | Liu et al. | |
| 2006/0183891 A1 | 8/2006 | Myette et al. | |
| 2006/0292130 A1 | 12/2006 | Sasisekharan et al. | |
| 2006/0292655 A1 | 12/2006 | Sasisekharan et al. | |
| 2006/0292673 A1 | 12/2006 | Sasisekharan et al. | |
| 2007/0004012 A1 | 1/2007 | Sasisekharan et al. | |
| 2007/0020243 A1 | 1/2007 | Sengupta et al. | |
| 2007/0065424 A1 | 3/2007 | Pojasek et al. | |
| 2007/0065921 A1 | 3/2007 | Sasisekharan et al. | |
| 2007/0066769 A1 | 3/2007 | Venkataraman et al. | |

(Continued)

FOREIGN PATENT DOCUMENTS

EP 0355831 2/1990
EP 0423818 A1 4/1991

(Continued)

OTHER PUBLICATIONS

Genbank Submission; NIH/NCBI, Accession No. AA605721; Ekker et al.; Sep. 29, 1997.

(Continued)

*Primary Examiner* — Tekchand Saidha
(74) *Attorney, Agent, or Firm* — Wolf, Greenfield & Sacks, P.C.

(57) ABSTRACT

This invention is related, in part, to sulfatase enzymes and methods of their use.

31 Claims, 14 Drawing Sheets

(56) References Cited

U.S. PATENT DOCUMENTS

| | | | |
|---|---|---|---|
| 2007/0072268 A1 | 3/2007 | Habuchi et al. |
| 2007/0148157 A1 | 6/2007 | Prabhakar et al. |
| 2007/0148158 A1 | 6/2007 | Sasisekharan et al. |
| 2007/0148740 A1 | 6/2007 | Prabhakar et al. |
| 2007/0161073 A1 | 7/2007 | Sasisekharan et al. |
| 2007/0202563 A1 | 8/2007 | Prabhakar et al. |
| 2007/0224670 A1 | 9/2007 | Prabhakar et al. |
| 2008/0071148 A1 | 3/2008 | Bosques et al. |
| 2008/0278164 A1 | 11/2008 | Sasisekharan et al. |
| 2008/0301178 A1 | 12/2008 | Venkataraman et al. |
| 2009/0045811 A1 | 2/2009 | Sasisekharan et al. |
| 2009/0081635 A1 | 3/2009 | Liu et al. |
| 2009/0105463 A1 | 4/2009 | Berry et al. |
| 2009/0119027 A1 | 5/2009 | Venkataraman et al. |
| 2009/0156477 A1 | 6/2009 | Berry et al. |
| 2009/0269326 A1 | 10/2009 | Myette et al. |
| 2010/0062468 A1 | 3/2010 | Sasisekharan et al. |
| 2010/0129868 A1 | 5/2010 | Myette et al. |

FOREIGN PATENT DOCUMENTS

| | | |
|---|---|---|
| JP | 69006619 B | 12/1965 |
| WO | WO 97/16556 A1 | 5/1997 |
| WO | WO 00/12726 A2 | 3/2000 |
| WO | WO 00/26393 A1 | 5/2000 |
| WO | WO 00/65521 A2 | 11/2000 |
| WO | WO 01/21640 A1 | 3/2001 |
| WO | WO 01/66772 A2 | 9/2001 |
| WO | WO 02/18539 A2 | 3/2002 |
| WO | WO 02/23190 A2 | 3/2002 |
| WO | WO 02/32406 A2 | 4/2002 |
| WO | WO 02/059327 A2 | 8/2002 |
| WO | WO 02/077199 A2 | 10/2002 |
| WO | WO 03/102160 A3 | 12/2003 |
| WO | WO 2004/031365 A2 | 4/2004 |
| WO | WO 2004/055491 A2 | 7/2004 |
| WO | WO 2004/062592 A2 | 7/2004 |
| WO | WO 2004/069152 A2 | 8/2004 |
| WO | WO 2005/017118 A2 | 2/2005 |
| WO | WO 2005/087920 A2 | 9/2005 |
| WO | WO 2005/110438 A2 | 11/2005 |
| WO | WO 2005/111627 A2 | 11/2005 |
| WO | WO 2006/076627 A2 | 7/2006 |
| WO | WO 2006/083328 A2 | 8/2006 |
| WO | WO 2006/088491 A2 | 8/2006 |
| WO | WO 2006/089206 A2 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

Genbank Submission; NIH/NCBI, Accession No. AAA51784.1; Peters et al.; Oct. 31, 1994.
Genbank Submission; NIH/NCBI, Accession No. AAA63197.1; Wilson et al.; Mar. 7, 1995.
Genbank Submission; NIH/NCBI, Accession No. AAB03341.1; Loftus et al.; Feb. 3, 2000.
Genbank Submission; NIH/NCBI, Accession No. AAC51350.1; Morris et al.; Oct. 11, 2005.
Genbank Submission; NIH/NCBI, Accession No. AAF72520.1, AF248951_1; Wright et al.; May 29, 2000.
Genbank Submission; NIH/NCBI, Accession No. AAG03573.1; Stover et al.; Jul. 7, 2006.
Genbank Submission; NIH/NCBI, Accession No. AAG05721.1; Stover et al.; Jul. 7, 2006.
Genbank Submission; NIH/NCBI, Accession No. AAL18999.1; McClelland et al.; Aug. 9, 2005.
Genbank Submission; NIH/NCBI, Accession No. AAL19003; McClelland et al.; Aug. 9, 2005.
Genbank Submission; NIH/NCBI, Accession No. AAL45441; Wood et al.; May 28, 2004.
Genbank Submission; NIH/NCBI, Accession No. AAL45442.1; Wood et al.; May 28, 2004.
Genbank Submission; NIH/NCBI, Accession No. AL355753; Redenbach et al.; May 12, 2002.
Genbank Submission; NIH/NCBI, Accession No. BAB38042.1; Makino et al.; May 26, 2006.
Genbank Submission; NIH/NCBI, Accession No. BAB79937; Shimizu et al; Oct. 21, 2004.
Genbank Submission; NIH/NCBI, Accession No. CAA51272.1; Modaressi et al.; Jun. 25, 1997.
Genbank Submission; NIH/NCBI, Accession No. CAA88421.2; Beil et al.; Jun. 30, 2006.
Genbank Submission; NIH/NCBI, Accession No. NP_248873.1; Stover et al.; Aug. 3, 2006.
Genbank Submission; NIH/NCBI, Accession No. P51691; Beil et al.; Sep. 19, 2006.
Database UniProt EBI Accession No. Q89YS5. (Jun. 1, 2003).
Database UniProt EBI Accession No. Q5LAU2. (Jun. 21, 2005).
[No Author Listed] Iduronate-2-sulfatase. Glyko Catalogue No. GAG-5009. Revised Sep. 2000.
Behr, Novel tools for sequence and epitope analysis of glycosaminoglycans. Submitted to the Biological Engineering Division in partial fulfillment of the requirements for the degree of Doctor of Philosophy in Biological Engineering at the Massachusetts Institute of Technology. Sep. 2007. 243 pages.
Beil et al., Purification and characterization of the arylsulfatase synthesized by *Pseudomonas aeruginosa* PAO during growth in sulfate-free medium and cloning of the arylsulfatase gene (atsA). Eur J Biochem. Apr. 15, 1995;229(2):385-94.
Bennett et al., High resolution analysis of functional determinants on human tissue-type plasminogen activator. J Biol Chem. Mar. 15, 1991;266(8):5191-201.
Bernfield et al., Functions of cell surface heparan sulfate proteoglycans. Annu Rev Biochem. 1999;68:729-77. Review.
Berteau et al., A new type of bacterial sulfatase reveals a novel maturation pathway in prokaryotes. J Biol Chem. Aug. 11, 2006;281(32):22464-70. Epub Jun. 9, 2006.
Bielicki et al., Human liver iduronate-2-sulphatase. Purification, characterization and catalytic properties. Biochem J. Oct. 1, 1990;271(1):75-86.
Boltes et al., 1.3 A structure of arylsulfatase from *Pseudomonas aeruginosa* establishes the catalytic mechanism of sulfate ester cleavage in the sulfatase family. Structure. Jun. 2001;9(6):483-91.
Bond et al., Structure of a human lysosomal sulfatase. Structure. Feb. 15, 1997;5(2):277-89.
Bruce et al., *Flavobacterium heparinum* 3-O-sulphatase for N-substituted glucosamine 3-O-sulphate. Eur J Biochem. Apr. 15, 1985;148(2):359-65.
Bruce et al., *Flavobacterium heparinum* 6-O-sulphatase for N-substituted glucosamine 6-O-sulphate. Eur J Biochem. Oct. 1, 1985;152(1):75-82.
Bruce et al., *Flavobacterium heparinum* sulphamidase for D-glucosamine sulphamate. Purification and haracterization. Eur J Biochem. Jun. 15, 1987;165(3):633-8.
Carlson et al., The determination of recombinant human tissue-type plasminogen activator activity by turbidimetry using a microcentrifugal analyzer. Anal Biochem. Feb. 1, 1988;168(2):428-35.
Chen et al., Analysis of mono- and oligosaccharide isomers derivatized with 9-aminopyrene-1,4,6-trisulfonate by capillary electrophoresis with laser-induced fluorescence. Anal Biochem. Sep. 20, 1995;230(2):273-80.
Cohlberg et al., Heparin and other glycosaminoglycans stimulate the formation of amyloid fibrils from alpha-synuclein in vitro. Biochemistry. Feb. 5, 2002;41(5):1502-11.
Dahiyat et al., De novo protein design: fully automated sequence selection. Science. Oct. 3, 1997;278(5335):82-7.
Desai et al., Specificity studies on the heparin lyases from *Flavobacterium heparinum*. Biochemistry. Aug. 17, 1993;32(32):8140-5.
Dierks et al., Conversion of cysteine to formylglycine in eukaryotic sulfatases occurs by a common mechanism in the endoplasmic reticulum. FEBS Lett. Feb. 13, 1998;423(1):61-5.

(56) References Cited

OTHER PUBLICATIONS

Dierks et al., Molecular basis for multiple sulfatase deficiency and mechanism for formylglycine generation of the human formylglycine-generating enzyme. Cell. May 20, 2005;121(4):541-52.
Dierks et al., Posttranslational formation of formylglycine in prokaryotic sulfatases by modification of either cysteine or serine. J Biol Chem. Oct. 2, 1998;273(40):25560-4.
Dietrich et al., Enzymic degradation of heparin. A glucosaminidase and a glycuronidase from *Flavobacterium heparinum*. Biochemistry. May 1969;8(5):2089-94.
Dietrich et al., Enzymic degradation of heparin. A sulphamidase and a sulphoesterase from *Flavobacterium heparinum*. Biochem J. Jan. 1969;111(1):91-5.
Dietrich et al., Sequential degradation of heparin in *Flavobacterium heparinum*. Purification and properties of five enzymes involved in heparin degradation. J Biol Chem. Sep. 25, 1973;248(18):6408-15.
Ernst et al., Enzymatic degradation of glycosaminoglycans. Crit Rev Biochem Mol Biol. 1995;30(5):387-444.
Ernst et al., Expression in *Escherichia coli*, purification and characterization of heparinase I from *Flavobacterium heparinum*. Biochem J. Apr. 15, 1996;315 ( Pt 2):589-97.
Esko et al., Molecular diversity of heparan sulfate. J Clin Invest. Jul. 2001;108(2):169-73. Review.
Feingold et al., Conformational aspects of the reaction mechanisms of polysaccharide lyases and epimerases. FEBS Lett. Nov. 2, 1987;223(2):207-11. Review.
Folkman et al., Control of angiogenesis by heparin and other sulfated polysaccharides. Adv Exp Med Biol. 1992;313:355-64.
Freeman et al., Human liver glucuronate 2-sulphatase. Purification, characterization and catalytic properties. Biochem J. Apr. 1, 1989;259(1):209-16.
Gacesa, Alginate-modifying enzymes: a proposed unified mechanism of action for the lyases and epimerases. FEBS Letters. 1987;212(2):199-202.
Glockner et al., Complete genome sequence of the marine planctomycete *Pirellula* sp. strain 1. Proc Natl Acad Sci U S A. Jul. 8, 2003;100(14):8298-303. Epub Jun. 30, 2003.
Godavarti et al., Heparinase III from *Flavobacterium heparinum*: cloning and recombinant expression in *Escherichia coli*. Biochem Biophys Res Commun. Aug. 23, 1996;225(3):751-8.
Gu et al., Purification, characterization and specificity of chondroitin lyases and glycuronidase from *Flavobacterium heparinum*. Biochem J. Dec. 1, 1995;312 ( Pt 2):569-77.
Häcker et al., Heparan sulphate proteoglycans: the sweet side of development. Nat Rev Mol Cell Biol. Jul. 2005;6(7):530-41. Review.
Hennekens et al., Current issues concerning thrombolytic therapy for acute myocardial infarction. J Am Coll Cardiol. Jun. 1995;25(7 Suppl):18S-22S. Review.
Higgins et al., Using Clustal for multiple sequence alignments. Methods Enzymol. 1996;266:383-402.
Holmes et al., Lessons we have learned from the GUSTO trial. Global Utilization of Streptokinase and Tissue Plasminogen Activator for Occluded Arteries. J Am Coll Cardiol. Jun. 1995;25(7 Suppl):10S-17S. Review.
Homans et al., A molecular mechanical force field for the conformational analysis of oligosaccharides: comparison of theoretical and crystal structures of Man alpha 1-3Man beta 1-4GlcNAc. Biochemistry. Oct. 2, 1990;29(39):9110-8.
Hovingh et al., Specificity of flavobacterial glycuronidases acting on disaccharides derived from glycosaminoglycans. Biochem J. Aug. 1, 1977;165(2):287-93.
Huige et al., Force field parameters for sulfates and sulfamates bases on Ab Initio calculations: Extensions of AMBER and CHARMm fields. J Comp Chem. 1995;16(1):56-79.
Ishikawa et al., Inhibition of glomerular cell apoptosis by heparin. Kidney Int. Sep. 1999;56(3):954-63.
Jandik et al., Action pattern of polysaccharide lyases on glycosaminoglycans. Glycobiology. 1994;4:289-296.
Kapila et al., The heparin-binding domain and V region of fibronectin regulate apoptosis by suppression of p53 and c-myc in human primary cells. J Biol Chem. Mar. 8, 2002;277(10):8482-91.
Kertesz et al., Riding the sulfur cycle—metabolism of sulfonates and sulfate esters in gram-negative bacteria. FEMS Microbiol Rev. Apr. 2000;24(2):135-75. Review.
Lai et al., hSulf1 Sulfatase promotes apoptosis of hepatocellular cancer cells by decreasing heparin-binding growth factor signaling. Gastroenterology. Jan. 2004;126(1):231-48.
Langer, New methods of drug delivery. Science. Sep. 28, 1990;249(4976):1527-33. Review.
Law et al., Studies on the particle-bound carbohydrate sulphoamide sulphohydrolase and carbohydrate sulphate sulphohydrolase of *Flavobacterium heparinum*. Biochem J. Nov. 1969;115(3):10P-11P.
Lindahl et al., Regulated diversity of heparan sulfate. J Biol Chem. Sep. 25, 1998;273(39):24979-82.
Linhardt et al., Examination of the substrate specificity of heparin and heparan sulfate lyases. Biochemistry. Mar. 13, 1990;29(10):2611-7.
Linhardt et al., Polysaccharide lyases. Appl Biochem Biotechnol. Apr. 1986;12(2):135-76.
Linker et al., The enzymatic degradation of heparin and heparitin sulfate. I. The fractionation of a crude heparinase from flavobacteria. J Biol Chem. Oct. 1965;240(10):3724-8.
Liu et al., Cell surface heparan sulfate and its roles in assisting viral infections. Med Res Rev. Jan. 2002;22(1):1-25.
Liu et al., Characterization of a heparan sulfate octasaccharide that binds to herpes simplex virus type 1 glycoprotein D. J Biol Chem. Sep. 6, 2002;277(36):33456-67. Epub Jun. 21, 2002.
Liu et al., Heparan sulfate D-glucosaminyl 3-O-sulfotransferase-3A sulfates N-unsubstituted glucosamine residues. J Biol Chem. Dec. 31, 1999;274(53):38155-62.
Lohse et al., Purification and characterization of heparin lyases from *Flavobacterium heparinum*. J Biol Chem. Dec. 5, 1992;267(34):24347-55.
Lukatela et al., Crystal structure of human arylsulfatase A: the aldehyde function and the metal ion at the active site suggest a novel mechanism for sulfate ester hydrolysis. Biochemistry. Mar. 17, 1998;37(11):3654-64.
Lyon et al., Bio-specific sequences and domains in heparan sulphate and the regulation of cell growth and adhesion. Matrix Biol. Nov. 1998;17(7):485-93.
McLean et al., Action of heparinase II on pig mucosal heparin. Proc. of the 8th International Symposium on Glycoconjugates. 1985. Abstract 73-74.
McLean et al., Enzymic removal of 2-O-sulphato-Δ4,5-glycuronic acid residues from heparin oligosaccharides. Proceedings of the 7th International Symposium of Glycoconjugates. Lund, Sweden. 1983;68-9.
McLean et al., *Flavobacterium heparinum* 2-O-sulphatase for 2-O-sulphato-delta 4,5-glycuronate-terminated oligosaccharides from heparin. Eur J Biochem. Dec. 17, 1984;145(3):607-15.
Morimoto-Tomita et al., Cloning and characterization of two extracellular heparin-degrading endosulfatases in mice and humans. J Biol Chem. Dec. 20, 2002;277(51):49175-85. Epub Oct. 3, 2002.
Myette et al., Expression in *Escherichia coli*, purification and kinetic characterization of human heparan sulfate 3-O-sulfotransferase-1. Biochem Biophys Res Commun Feb. 1, 2002;290(4):1206-13.
Myette et al., Heparin/heparan sulfate 6-O-sulfatase from *Flavobacterium heparinum*: integrated structural and biochemical investigation of enzyme active site and substrate specificity. J Biol Chem. Dec. 11, 2009;284(50):35177-88.
Myette et al., Heparin/heparan sulfate N-sulfamidase from *Flavobacterium heparinum*: structural and biochemical investigation of catalytic nitrogen—sulfur bond cleavage. J Biol Chem. Dec. 11, 2009;284(50):35189-200. Epub Sep. 2, 2009.
Myette et al., Molecular cloning of the heparin/heparan sulfate delta 4,5 unsaturated glycuronidase from *Flavobacterium heparinum*, its recombinant expression in *Escherichia coli*, and biochemical determination of its unique substrate specificity. Biochemistry. Jun. 11, 2002;41(23):7424-34.
Myette et al., The heparin/heparan sulfate 2-O-sulfatase from *Flavobacterium heparinum*. Molecular cloning, recombinant

(56) References Cited

OTHER PUBLICATIONS expression, and biochemical characterization. J Biol Chem. Apr. 4, 2003;278(14):12157-66. Epub Jan. 7, 2003.

Nakamura et al., Purification and properties of *Bacteroides heparinolyticus* heparinase (heparin lyase, EC 4.2.2.7). J Clin Microbiol. May 1988;26(5):1070-1.

Nielsen et al., Identification of prokaryotic and eukaryotic signal peptides and prediction of their cleavage sites. Protein Eng. Jan. 1997;10(1):1-6.

Parenti et al., The sulfatase gene family. Curr Opin Genet Dev. Jun. 1997;7(3):386-91. Review.

Perrimon et al., Specificities of heparan sulphate proteoglycans in developmental processes. Nature. Apr. 13, 2000;404(6779):725-8.

Petitou et al., Synthetic oligosaccharides having various functional domains: potent and potentially safe heparin mimetics. Bioorg Med Chem Lett. Apr. 19, 1999;9(8):1161-6.

Prince et al., Cell-matrix interactions during development and apoptosis of the mouse mammary gland in vivo. Dev Dyn. Apr. 2002;223(4):497-516.

Raman et al., Identification of structural motifs and amino acids within the structure of human heparan sulfate 3-O-sulfotransferase that mediate enzymatic function. Biochem Biophys Res Commun. Feb. 1, 2002;290(4):1214-9.

Raman et al., The heparin/heparan sulfate 2-O-sulfatase from *Flavobacterium heparinum*. A structural and biochemical study of the enzyme active site and saccharide substrate specificity. J Biol Chem. Apr. 4, 2003;278(14):12167-74. Epub Jan. 7, 2003.

Razi et al., Structural and functional properties of heparin analogues obtained by chemical sulphation of *Escherichia coli* K5 capsular polysaccharide.Biochem J. Jul. 15, 1995;309 ( Pt 2):465-72.

Rhomberg et al., Mass spectrometric and capillary electrophoretic investigation of the enzymatic degradation of heparin-like glycosaminoglycans. Proc Natl Acad Sci U S A. Apr. 14, 1998;95(8):4176-81.

Rhomberg et al., Mass spectrometric evidence for the enzymatic mechanism of the depolymerization of heparin-like glycosaminoglycans by heparinase II. Proc Natl Acad Sci U S A. Oct. 13, 1998;95(21):12232-7.

Roberton et al., Assays for bacterial mucin-desulfating sulfatases. Methods Mol Biol. 2000;125:417-26. Review.

Sasisekharan et al., Cloning and expression of heparinase I gene from *Flavobacterium heparinum*. Proc Natl Acad Sci U S A. Apr. 15, 1993;90(8):3660-4.

Sasisekharan et al., Heparinase inhibits neovascularization. Proc Natl Acad Sci U S A. Feb. 15, 1994;91(4):1524-8.

Sasisekharan et al., Roles of heparan-sulphate glycosaminoglycans in cancer. Nat Rev Cancer. Jul. 2002;2(7):521-8. Review.

Sehayek et al., Binding to heparan sulfate is a major event during catabolism of lipoprotein lipase by HepG2 and other cell cultures. Atherosclerosis. Apr. 7, 1995;114(1):1-8.

Selva et al., Role of heparan sulfate proteoglycans in cell signaling and cancer. Adv Cancer Res. 2001;83:67-80.

Shaklee et al., A sulfatase specific for glucuronic acid 2-sulfate residues in glycosaminoglycans. J Biol Chem. Aug. 5, 1985;260(16):9146-9.

Shriver et al., Emerging views of heparan sulfate glycosaminoglycan structure/activity relationships modulating dynamic biological functions. Trends Cardiovasc Med. Feb. 2002;12(2):71-7.

Silver et al., Amino terminus of the yeast GAL4 gene product is sufficient for nuclear localization. PNAS. 1984;81:5951-5955.

Simeon et al., Expression of glycosaminoglycans and small proteoglycans in wounds: modulation by the tripeptide-copper complex glycyl-L-histidyl-L-lysine-Cu(2+). J Invest Dermatol. Dec. 2000;115(6):962-8.

Sugahara et al., Specificity studies of bacterial sulfatases by means of structurally defined sulfated oligosaccharides isolated from shark cartilage chondroitin sulfate D. Eur J Biochem. Aug. 1, 1996;239(3):865-70. Abstract only.

Toida et al., Enzymatic preparation of heparin oligosaccharides containing antithrombin III binding sites. J Biol Chem. Dec. 13, 1996;271(50):32040-7.

Tumova et al., Heparan sulfate proteoglycans on the cell surface: versatile coordinators of cellular functions. Int J Biochem Cell Biol. Mar. 2000;32(3):269-88.

Venkataraman et al., Sequencing complex polysaccharides. Science. Oct. 15, 1999;286(5439):537-42.

Vivès et al., Heparan sulphate proteoglycans and viral vectors : ally or foe? Curr Gene Ther. Feb. 2006;6(1):35-44. Review.

Vlodavsky et al., Mammalian heparanase as mediator of tumor metastasis and angiogenesis. Isr Med Assoc J. Jul. 2000;2 Suppl:37-45.

Vlodavsky et al., Mammalian heparanase: gene cloning, expression and function in tumor progression and metastasis. Nat Med. Jul. 1999;5(7):793-802.

Von Bulow et al., Crystal structure of an enzyme-substrate complex provides insight into the interaction between human arylsulfatase A and its substrates during catalysis. J Mol Biol. Jan. 12, 2001;305(2):269-77.

Von Figura et al., A novel protein modification generating an aldehyde group in sulfatases: its role in catalysis and disease. Bioessays. Jun. 1998;20(6):505-10. Abstract only.

Waldow et al., Amino acid residues forming the active site of arylsulfatase A. Role in catalytic activity and substrate binding. J Biol Chem. Apr. 30, 1999;274(18):12284-8.

Warnick et al., Purification of an unusual—glycuronidase from *Flavobacteria*. Biochemistry. Feb. 15, 1972;11(4):568-72.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Wright et al., Cloning of a mucin-desulfating sulfatase gene from *Prevotella* strain RS2 and its expression using a *Bacteroides* recombinant system. J Bacteriol. Jun. 2000;182(11):3002-7.

Xiang et al., A method to increase contaminant tolerance in protein matrix-assisted laser desorption/ionization by the fabrication of thin protein-doped polycrystalline films. Rapid Commun Mass Spectrom 1994;8:199-204.

Yang et al., Purification and characterization of heparinase from *Flavobacterium heparinum*. J Biol Chem. Feb. 10, 1985;260(3):1849-57.

Yates et al., 1H and 13C NMR spectral assignments of the major sequences of twelve systematically modified heparin derivatives. Carbohydr Res. Nov. 20, 1996;294:15-27.

Zhang et al., 6-O-sulfotransferase-1 represents a critical enzyme in the anticoagulant heparan sulfate biosynthetic pathway. J Biol Chem. Nov. 9, 2001;276(45):42311-21. Epub Sep. 10, 2001.

\* cited by examiner

```
   1 - ATACTAAAAATGGGTAAATTGAAATTAATTTTACCGGTTTTGTTTGCCGGTGCCACCTTA -   60
  (1)- I  L  K  M  G  K  L  K  L  I  L  P  V  L  F  A  G  A↓ T  L    - (17)
  61 - ATGTCTTGCCAGCAGCCTAAACCTGCTGAAAGTGCCAAAAGGCCCAATATTGTGTTCATC -  120
 (18)- M  S  C  Q  Q  P  K  P  A  E  S  A  K  R  P  N  I  V  F  I    - (37)
 121 - ATGACAGATGACCATACCATTCAGGCCATAAGCGCTTATGGCAGCAAATTGGTAAAAACG -  180
 (38)- M  T  D  D  H  T  I  Q  A  I  S  A  Y  G  S  K  L  V  K  T    - (57)
 181 - CCCAACCTGGACAGAATTGCCAACGAGGGTATGTTGTTTAACAACTGTTTTGTAACCAAT -  240
 (58)- P  N  L  D  R  I  A  N  E  G  M  L  F  N  N  C  F  V  T  N    - (77)
 241 - GCAGTTTGCGGGCCATCCAGGGCTACTATCCTGACCGGAAAATATAGCCACCTGAATGGT -  300
 (78)- A  V [C  G  P  S  R  A  T  I  L  T  G] K  Y  S  H  L  N  G    - (97)
 301 - TTAACAGACAATTCAAAGGTATTTGACAGTACTCAGGTTATTTATCCGCAGTTGTTAAAG -  360
 (98)- L  T  D  N  S  K  V  F  D  S  T  Q  V  I  Y  P  Q  L  L  K    -(117)
 361 - AAAGCAGGGTACCAGACCGCAATGATTGGCAAGTGGCACCTGGGCTCAACACCAATGGGC -  420
(118)- K  A  G  Y  Q  T  A  M  I  G  K  W  H  L  G  S  T  P  M  G    -(137)
 421 - TTTGACTATTACAGTATTTTGCCCAACCAGGGACAATATATCAGCCTGAATTTATAGAA  -  480
(138)- F  D  Y  Y  S  I  L  P  N  Q  G  Q  Y  Y  Q  P  E  F  I  E    -(157)
 481 - AACGGGCATCTGGTTAAAGAAAAAGGATATGTAACAGACCTCATCACCGATAAGGCCATC -  540
(158)- N  G  H  L  V  K  E  K  G  Y  V  T  D  L  I  T  D  K  A  I    -(177)
 541 - GGCTTCCTTGAAAAAGGGACCATGATAAACCCTTTCTGATGATTTACCAGCACAAAGCA  -  600
(178)- G  F  L  E  K  R  D  H  D  K  P  F  L  M  I  Y  Q  H  K  A    -(197)
 601 - CCGCACCGCAACTGGTTGCCGGCACCAAGACACCTGGGGATGTTTGACGATACGGTTTTT -  660
(198)- P  H  R  N  W  L  P  A  P  R  H  L  G  M  F  D  D  T  V  F    -(217)
 661 - CCTGAACCTGCCAATTTACTGGATGATTTAAGGGCAGGGGCAGGGCAGCAAAGGAGCAG  -  720
(218)- P  E  P  A  N  L  L  D  D  F  K  G  R  G  R  A  A  K  E  Q    -(237)
 721 - CTGATGAACATTTCTACCGATATGTGGCCTGCATGGGACCTTAAAATGCTTTCTACAGCC -  780
(238)- L  M  N  I  S  T  D  M  W  P  A  W  D  L  K  M  L  S  T  A    -(257)
 781 - CAGCTTGATTCTATGGCGAAACTACCTGTTTCCCCTAAGTTTAAAGATGCCAAGGGTGAT -  840
(258)- Q  L  D  S  M  A  K  L  P  V  S  P  K  F  K  D  A  K  G  D    -(277)
 841 - GATTATCAACAGGCCAATGATCCTTCACTGGATAAAGCCCGTTTTTTTGAAGTGTACAAC -  900
(278)- D  Y  Q  Q  A  N  D  P  S  L  D  K  A  R  F  F  E  V  Y  N    -(297)
 901 - CGCATGACAGATGCTGAAAAGGTACAATGGAGAAAAGTATATGACAAACGCGTAGCCGAA -  960
(298)- R  M  T  D  A  E  K  V  Q  W  R  K  V  Y  D  K  R  V  A  E    -(317)
 961 - TTTAAAAGGCTGAACCCGAAAGGGGCCGACCTGGTGCGATGGAAATACCAGCAGTATATG - 1020
(318)- F  K  R  L  N  P  K  G  A  D  L  V  R  W  K  Y  Q  Q  Y  M    -(337)
1021 - CGCGATTATCTGGCCTGCGTGGTTTCGGTAGATGAAAATGTAGGCAGGCTGATGGATTAC - 1080
(338)- R  D  Y  L  A  C  V  V  S  V  D  E  N  V  G  R  L  M  D  Y    -(357)
1081 - CTGAAAAAGATAGGGGAGCTGGACAATACCATTATTGTCTATACTTCCGATCAGGGCTTT - 1140
(358)- L  K  K  I  G  E  L  D  N  T  I  I  V  Y  T  S  D  Q  G  F    -(377)
1141 - TATTTGGGTGAGCATGGGTATTTCGACAAACGTTTTATGTACGATGAATCTTTCCGTACA - 1200
(378)- Y  L  G  E  H  G  Y  F  D  K  R  F  M  Y  D  E  S  F  R  T    -(397)
1201 - CCTTTAATGGTGAGGTATCCGCCTTCGGTTAAAGCCGGTTCAGTAAGTAATGCCTTTGCC - 1260
(398)- P  L  M  V  R  Y  P  P  S  V  K  A  G  S  V  S  N  A  F  A    -(417)
1261 - ATGAACCTCGATTTTGCACCAACTTTACTGGATTATGCAGGGGTAAAAATACCAGCCGAT - 1320
(418)- M  N  L  D  F  A  P  T  L  L  D  Y  A  G  V  K  I  P  A  D    -(437)
1321 - ATGCAGGGCCTGTCGTTACGTCCGGTATTGGATAACGCAGGAAAATCGCCGGAAAACTGG - 1380
(438)- M  Q  G  L  S  L  R  P  V  L  D  N  A  G  K  S  P  E  N  W    -(457)
1381 - CGCAAGGCTGTATATTATCATTATTATGAATTTCCAAGCTGGCACATGGTTAAAAGGCAC - 1440
(458)- R  K  A  V  Y  Y  H  Y  Y  E  F  P  S  W  H  M  V  K  R  H    -(477)
1441 - TATGGCATCAGAACGGAGCGCTATAAACTTGATCCATTTTTACAATGACATTGATGAATGG - 1500
(478)- Y  G  I  R  T  E  R  Y  K  L  I  H  F  Y  N  D  I  D  E  W    -(497)
1501 - GAATTATACGATATGCAGAAAGATCCGCATGAGATGCAAAACCTGTATAACGATAAGGCC - 1560
(498)- E  L  Y  D  M  Q  K  D  P  H  E  M  Q  N  L  Y  N  D  K  A    -(517)
1561 - TATGAGCCGATTATTAAAGACCTGAAAGTGCAAATGAAAAAGCTGCAGGTACAATATAAA - 1620
(518)- Y  E  P  I  I  K  D  L  K  V  Q  M  K  K  L  Q  V  Q  Y  K    -(537)
1621 - GATACGAATCCAACTGAAGCTTTATAA - 1647
(538)- D  T  N  P  T  E  A  L  stop (545)
```

Fig. 1

```
   1 - AGCTTTATAAAATTGATAAAGATGAAATTTAACAAATTGAAATATTTCCCTGCAGCACTT -   60
  (1)- S  F  I  K  L  I  K  M  K  F  N  K  L  K  Y  F  P  A  A  L    -(13)
  61 - TCAATGGTGCTGATATGGGCTTCCTGCACTTCGCCGGAAAAAAAAACGGATCGTCCGAAT -  120
 (14)- S  M  V  L  I  W  A ↓S  C  T  S  P  E  K  K  T  D  R  P  N    -(33)
 121 - ATCCTGATGATCATGTCCGATAACCAATCCTGGAACCACGTAGGGAGCTATGGTGATCAA -  180
 (34)- I  L  M  I  M  S  D  N  Q  S  W  N  H  V  G  S  Y  G  D  Q    -(53)
 181 - ACGGTACGCACGCCCAATATGGACCGGATTGCGAAAGAAGGGGTACGTTTTACCAATGCT -  240
 (54)- T  V  R  T  P  N  M  D  R  I  A  K  E  G  V  R  F  T  N  A    -(73)
 241 - TTTTGCAGTTCACCTTCCTGTACGCCCGCAAGGGCTGGAATGCTGACCGGACAGGATATA -  300
 (74)- F  C  S  S  P  S │C  T  P  A  R  A  G  M  L  T  G│ Q  D  I    -(93)
 301 - TGGAGGTTAGAAGATGGGGGCAATTTATGGGGTGTTTTACCGGTTAAATATAAAGTATAT -  360
 (94)- W  R  L  E  D  G  G  N  L  W  G  V  L  P  V  K  Y  K  V  Y    -(113)
 361 - CCGGATTTGCTGGAAGAAGCTGGCTATGCCATAGGTTTTCAGGGAAAAGGCTGGGGCCCG -  420
(114)- P  D  L  L  E  E  A  G  Y  A  I  G  F  Q  G  K  G  W  G  P    -(133)
 421 - GGAAGCTTTGAGGCCAATAAACGCCCAAGAAATCCTGCAGGGAATGAGTTTAAAAGTTTT -  480
(134)- G  S  F  E  A  N  K  R  P  R  N  P  A  G  N  E  F  K  S  F    -(153)
 481 - GGCGCATTTTTAAAAGATAAAAAAGAAGGTCCCTGGTGTTATTGGATCAGTAGTCATGAA -  540
(154)- G  A  F  L  K  D  K  K  E  G  P  W  C  Y  W  I  S  S  H  E    -(173)
 541 - CCTCACCGTCCTTATGTGGAAGGTTCCGGCGAAAAAGCTGGTATCGATCCAAATAAAGTA -  600
(174)- P  H  R  P  Y  V  E  G  S  G  E  K  A  G  I  D  P  N  K  V    -(193)
 601 - AAAGTTCCTGCCTATTTGCCAGATCATATCAGTATAAGAAAAGACATTGCAGATTACTAC -  660
(194)- K  V  P  A  Y  L  P  D  H  I  S  I  R  K  D  I  A  D  Y  Y    -(213)
 661 - GCTCGGTTGAAACCTTTGATCGTGAACTGGGCGAGGCCCTTGACCAGTTGAAAGCAAGT -  720
(214)- A  A  V  E  T  F  D  R  E  L  G  E  A  L  D  Q  L  K  A  S    -(233)
 721 - GGTGAGCTGGACAATACGGTAATTGTGGTATGCAGTGACAACGGCTGGCAAATGCCGCGT -  780
(234)- G  E  L  D  N  T  V  I  V  V  C  S  D  N  G  W  Q  M  P  R    -(253)
 781 - GGACTGGCCAACTTGTACGATTTTGGTACACATGTGCCCCTGATCATTTCATGGCCAGGT -  840
(254)- G  L  A  N  L  Y  D  F  G  T  H  V  P  L  I  I  S  W  P  G    -(273)
 841 - AAGTTTAAACAGGATGTAGTTGCCGATAACCTGGTCACACTGAATGACCTTGCCCCAACA -  900
(274)- K  F  K  Q  D  V  V  A  D  N  L  V  T  L  N  D  L  A  P  T    -(293)
 901 - TTCTTACAACTGGGTAAGGTACCTGTACCGGCCGATATGACGGGTAAAAGTTTATTGCCC -  960
(294)- F  L  Q  L  G  K  V  P  V  P  A  D  M  T  G  K  S  L  L  P    -(313)
 961 - ATTGTTGAGGCAGGTAAAAAAGATGAAAAACCCCGGGATTATGTAGTACTGGGAAGAGAG - 1020
(314)- I  V  E  A  G  K  K  D  E  K  P  R  D  Y  V  V  L  G  R  E    -(333)
1021 - CGTCATGCATTCGTTCGTCGGCATGGCCTTGGCTATCCTGGCAGGGCAATTCGTACTAAA - 1080
(334)- R  H  A  F  V  R  R  H  G  L  G  Y  P  G  R  A  I  R  T  K    -(353)
1081 - GATTATCTTTACATTAAAAATTATGAACCAAATAGATGGCCGGCAGGTGATCCGCCGTTT - 1140
(354)- D  Y  L  Y  I  K  N  Y  E  P  N  R  W  P  A  G  D  P  P  F    -(373)
1141 - TATGGAGACATTGATCCCTACATGTTCAACTGGCCGGGTGAAACCAAATATTACCTGATA - 1200
(374)- Y  G  D  I  D  P  Y  M  F  N  W  P  G  E  T  K  Y  Y  L  I    -(393)
1201 - GAACATAAAGATGATCCGAAAGTAAAGTCTTTCTTTGAACTGGGAATGGGCAAACGTCCG - 1260
(394)- E  H  K  D  D  P  K  V  K  S  F  F  E  L  G  M  G  K  R  P    -(413)
1261 - GCAGAAGAATTATTTGATATCAATAAAGATCCGGATGAATTACACAATCTGGCAGCACTT - 1320
(414)- A  E  E  L  F  D  I  N  K  D  P  D  E  L  H  N  L  A  A  L    -(433)
1321 - CCTGAATATCAAAAAATAAAACAGGAGCTTGTTGCTAAATTGCGTAATTATTTGGTAGCA - 1380
(434)- P  E  Y  Q  K  I  K  Q  E  L  V  A  K  L  R  N  Y  L  V  A    -(453)
1381 - ACGAAAGATCCGAGAGAAACTAATGGTAATATACAGATCTGGGATACTGCTGCTTATTTT - 1440
(454)- T  K  D  P  R  E  T  N  G  N  I  Q  I  W  D  T  A  A  Y  F    -(473)
1441 - AGTGAAATAGATAAAACGCCAAAACCAAGTAAAGAGATGCAAAAGCGTTTTAAATTAGAT - 1500
(474)- S  E  I  D  K  T  P  K  P  S  K  E  M  Q  K  R  F  K  L  D    -(493)
1501 - TCCAGTTACAATTATTTGAAGTAA - 1524
(494)- S  S  Y  N  Y  L  K  stop (500)
```

Fig. 2

```
Flavo ORF B      MGKLKEILPVLFAGATLMSCQQPKPAESAKRPNIVFIMTDDHTIQAISAYG---SKLVKI
Bacter. mucin    MKSNPSTLLLPLAALSLASCANPQ-KEETKRPNIFMMTDDHTTQAMSCYG---GNLIQI
Prev. AptA       MKSDN----MRFYSAMLMAGCGLHAAAQTQRPNIVFILTDDHSTQTISAYGSEVSKLAPI
Human Gal-6      -MAAVWAATRWWQLLLVISAAGMGASGAPQPPNILLLLMDDMGWGDIGVYG---EPSREI
CONSENSUS        mks--l-l-l-faa--lmscaqp-aae-t-rPNIvfimtDDhtfqaisaYG---skli-T Flavo ORF B      PNLDRIANEGMLFNNCIVTNAVCGPSRATNLTGKYSHLNGLTDN-------------SKV
Bacter. mucin    PNMDRIANEGIRFDNCKAVNALSGPSRACILTGKFSHENGFTDN-------------AST
Prev. AptA       PNIDRLANEGARFDDAEVENSLSTPARACILTGLYSHQNGQRTL-------------QKG
Human Gal-6      PNLDRMAAEGILLPNFYSANPLCSPSRAALLTGRLPIRNGFYTTNAHARNAYTPQEIVGG
CONSENSUS        PNlDRiAnEGi-Fdncyv-Nal-gPsRAciLTGkysh-NGft-n-------------akg Flavo ORF B      FDSTQVIYPQLLKKAGYQTAMIGKWHLGSTPM------GFDIYS-----ILP---NQGQY
Bacter. mucin    FNGDQQTFPKLLQQAGYQTAMIGKWHLTSEPQ------GFDHWS-----ILSGQHEQGDY
Prev. AptA       IDSTKTFVSELLQDAGYQTGVVGKWHMQCRPK------GFDFER-----IFE---GQGDY
Human Gal-6      IPDSEQELPELLKKAGYVSKIVGKWHLGHRPQFHPLKHGFDEWFGSPNCHFGPYDNKARP
CONSENSUS        -dstqqi-peLL-kAGYqtamiGKWHlgsrPq------GFDyws-----i-----nqgdy Flavo ORF B      YQPEFIE---NGHLVKEK---------GYVTDLITDKAIGFLEKRDHDKPFLMIYQHKAPH
Bacter. mucin    YDPDFWE---DGKHIVEK---------GYATDIITDKAINFLENRDKNKPFCMMYHQKAPH
Prev. AptA       YNPLVLSHDSNGKYEREQ---------GYATDIMTEHAVEFLNQRDEQKPFFLLVEHKAPH
Human Gal-6      NIEVYRDWEMVGRYYEEFPINLKTGEANLTQIYLQEALDEIKRQARHHPFFLYWAVDATH
CONSENSUS        yqP-fie-d-nGkyikEk---------gyaTdiitdkAieFle-rdknkPFfmmy-hkApH Flavo ORF B      RNWLPAPRHLGMFDDTVFPEPANLLDDIKGRGRAAKEQLMNISTDWWPAWDLKMLSTAQI
Bacter. mucin    RNWMPAPRHLGIFNNTIFPEPANLFDDYEGRGKAAREQDMSIEHTITNDWDLKILLREEM
Prev. AptA       RTWMPNLKYLGIYDKVEFPLPTTFWDDYATRGTCASQQEMILARHMQLAYDNKVFEIDNA
Human Gal-6      APVYASKPFLGTSQRGRVGDAVREIDDSIG-------KILELLQDLHVADNTFVFFTSDN
CONSENSUS        rnwmpaprhLGifdktifpepanl-DDy-grgkaareq-msi--dl-lawdlkv-tte-m Flavo ORF B      DSMAKLPVSPKFKDAKGDDYQQANDPSLDKARFIEVYNRMLDAEKVQWRKVYDKRWAEEK
Bacter. mucin    -----------IKDTTN-------------RLYSVYKRMPSEVQDKWDSAYAQRIAENR
Prev. AptA       -----------MRTR-------------------MLDRMDRLQKQAWDAYYSPRNRAML
Human Gal-6      -------------------------------GAALISAPEQGCSNGPELCGKQTTF
CONSENSUS        -----------lkd-----------------r-y-vy-rmt-e--awda-y--riaeyr Flavo ORF B      RLNPKGADLVRWKYQQYMRDYLACVMSVDENVGRLMDYLKKIGELDNTIIVYTSDQGFYL
Bacter. mucin    KGDLKGKALISWKYQQYMRDYLATVLAVDENIGRLLNYLEKIGELDNTIIVYTSDQGFEL
Prev. AptA       DAHLTDSALTVWKYQRYMHDYLSTIHSVDESVGEIYEYLKNHNLLDNTIIVYCSDQGFYM
Human Gal-6      EGGMREPALAWWPGHVTAGQVSHQLGSIMDLFTTSLALAGLTPPSDRAIDGLNLLPTLLQ
CONSENSUS        -g-lkg-aLi-WkyqqymrdylatvlsvdenvgrlldylkkigelDntIivytsdqgfyl Flavo ORF B      GEHGWFDKRFMYDESFRTPLMVRYPPSMKAGS-VSNAFAMNLDFAPTLLDYAGVKIPADM
Bacter. mucin    GEHGWFDKRFMYEECQRMPLILIRYPKAIKAGS-TSSAISMNVDFAPTFLDFAGVEVPSDI
Prev. AptA       GEHGWFDKRFMYEESLRTPLVVRYPKAIKPGI-VDKHLVQNIDFAPTLLDFAGVTKPETM
Human Gal-6      GRLMDRPIFYYRGDILMAATLGQHKAHFWTWINSWENFRQGLDFCP-GQNVSGVTT-HNI
CONSENSUS        Gehgwfdkrfmyeeslrtplivrypkaikags-vs-af--niDFaPtlldvaGVtvp-dm Flavo ORF B      QGLSLRPVLDNAGKSPENWRKAVYYHYYEEPSWHMVKRHYGIRTERYKLIHFY-------
Bacter. mucin    QGASLKPVLENEGKTPADWRKAAYYHYYEYPAEHSVKRHYGIRTQDEKLIHFY-------
Prev. AptA       SGRSFLDIFDGKGQ---DWRQSIYYHYYDYPAEHHVRRHDGVRTDRYKLIHFYGAPMEGD
Human Gal-6      EDHTKLPIIFHLGRDPGERFPLSEASAEYQEALSRITSVVQQHQEALVPAQP--------
CONSENSUS        qg-sllpvldn-Gktpadwrkavyyhyyeypaeh-vkrhygirteryklihfy-------

Flavo ORF B      -NDIDEWELYDMQKDPHEMQNLYNDKAYEPTIKDIKVQMKKLQVQYKDTNPTEAL-----
Bacter. mucin    -NDIDEWEMYDMKADPREMNNIRGKAEYAKKQKELMQLLEETQKQYKDNPPDEKETVLFK
Prev. AptA       HDTVDYEELYDMQNDPNELNNLYGKKGYEKITKELRKALKDYRKNLKVDEY--------
Human Gal-6      QLNVCNWAVMN---------------WAPPGCEKEGKCLTPPESIPKKCLWSH-------
CONSENSUS        -ndidewelydmq-dp-emnnlygkkgyeki-KeLk--lke-qkq-kd-dp-e-------
```

```
Human_ARS_B   MGPRGAASLPRGPGPRRLEEPVVLPLLWLLLLAPPGSGAGASRPHHLVFLLADDLGWNDV
Human_ARS_A   ------------------MSMGAPRSLLLALA---AGLAVARPPNIVLTFADDLGVGDL
PARSA_        -----------------------------------MSKRPNFLVIWADDLGFSDI
ORF_B_[6-0]   -----------MGKLKLILPVLFAGATLMSCQQPKP-AESAKRPNIVFIMTDDHTIQAL
ORFC_[NS]     -----------MKFNKLKYFPAALSMVLIWASCTSPEKKTDRRNILMIMSDNQSWNHV
CONSENSUS     ------------------lI-v-----lll---n-----srrPnivlilaDdlgwndv Human_ARS_B   GFHGS-RIRTPHLDALAAGGVLLDNVTQP-LCTPSRSQLLTG--RYQIRTGLQNQIFWP
Human_ARS_A   GCYGHPSSTTPNLDQLAAGGLRFLTDFYVPVSLCTPSRAALLTG--RLPVRMGMYPGVLVP
PARSA_        GAEGG-EFATPNLDALAIAGLRLTDPHTAS-TCSPTRSMLLTG-TDHHIAGICTMAEALTP
ORF_B_[6-0]   SAYGSKLVKTPNLDRFANEGMLFNNCEVTNAVCGPSRATRLTG--KYSHLNGLTDNSKVF
ORFC_[NS]     GSIYGDQTVRITPNMDRLAKEGVRFTNARCSSPSCTPARAGMLTGQDIWRLEDGGNLWGVIP
CONSENSUS     g-yG---IrrPnlD-lA-gGvrFtnyy----lctPsRn-lLTG--ry-l---Gl----lvp Human_ARS_B   CQPS------CVPLDEKLLPQLLKEAGYTTHMVGK-WHLGMYR-KECLPTRRGFEIYIEGY
Human_ARS_A   SSRG------GLPLEEVTVALVLAARGYLTGMACK-WHLGLEKP-EQTPHARGFERSFSL
PARSA_        ELEGKPGYEGHINERVVAALPELLREAGYQTLMAGK-WHLGEKP--EQTPHARGFERSFSL
ORF_B_[6-0]   DS--------TQVTYPQLLKKAGYQTAMICK-WHLGSTP---------MGFD-MYSI
ORFC_[NS]     ------------VKYKVYPDLLEEAGYAIGFQGKGWGPGS--------------
CONSENSUS     ----------v-I---vllpelLkeaGY-tga-GK-WhlGm-p-----p---gfd-yf-I Human_ARS_B   LLGSED--------VYSHERCTLIDALNVTRCALDFRDGEEVATGMKN-MYSTNIFTKRA
Human_ARS_A   PYSHDQGPCQNLTCEFPATPCDGGCDQGIVPIPLLANLSVEAQPPWLP-GLEARYMAFAH
PARSA_        LPGAAN--------HVGFEPPYDESTPRIEKGTPALYVEDERYLDTLPEGFYSSDAFGDKL
ORF_B_[6-0]   LPNQCD--------MYQPEFIENCHLVKEKCYVTDLITDKAIGFLEKRDHDKPFLMIYQH
ORFC_[NS]     --------------REANKRPRNPAGNEFKSFGAFLKDKKEGPWCM--------------
CONSENSUS     I----q--------y------d------vk---------d--e----y-------------

Human_ARS_B   IALITNHPEEKPLFLYLALQSVHEPLQVPEEYLKPYDFIQDKNRHHYAGMVSLMDEAVGN
Human_ARS_A   DLMADAQRQDREPFFLYYASHHTHYPQFS------GQSFAERSRGPEGDSIMELDAAVGT
PARSA_        LQYLKERDQSRPPFAVLPFSAPHWPLQAPREIVEKYRGRYDAGPEALRQERLARLKELGL
ORF_B_[6-0]   KAPHRNWLPAPRHLGMFDDTVFPEDANMLDDPKGRGRAAKEQLMNISTDMWPAWDLKMLS
ORFC_[NS]     --WISSHEPHREPKVEGSGFKAGIDPNKVKVPAYLPDHISIRKDIADMYAAMETFDRELGH
CONSENSUS     ---I----p-rpff-y-a----heP-qv--e---------d-----y---v---d--vg- Human_ARS_B   VTAALKSSGLWNNTVFIFSTDNGGQTL---AGGNNWPIRG------RKWSLWEGGVRGVG
Human_ARS_A   EMTARGDLGLLEETLVFFTADNGPETMRMSRGGCSGLLRC------GKGTTYEGGVREPA
PARSA_        VEADVEAHPVLALTREWEALEDEERAKSARANEVYAAMVERMDWNIGRVVQWREPA
ORF_B_[6-0]   TAQLDSMAKLPVSPKFKDAKGDDYQQANDPSLDKARFFEVYNRMTDAEKVQWRKVYDKRV
ORFC_[NS]     ALDQLKASCELDNTVIVCSDNGWQMPRCLANLYDFGTHVPLIISWPGKFKQDVVADNEV
CONSENSUS     v---I----gII--tv-I----dng-q-----a------I-------gk---we-----v-

Human_ARS_B   FVASPLLK--QKGVKNRELIHISDWLPTLVKLAR---GHTNGTKPLDGFDVWKTISEGSP
Human_ARS_A   LAFWPGHI--APGVT-HELASSLDLLPTLAALAG---APLP-NVTEDGFDLSPILLGTGK
PARSA_        NTFVLFMS--DNGAEGALLEAFPKSLEGPDLIGFLD---RHYDNSLENIGRANSYVWYGPRW
ORF_B_[6-0]   AEEKRLNPKGADLVRWKYQQYMRDALACVWSVDENVGRLMDYLKKIGELDNTILWYTSDQ
ORFC_[NS]     TLNDLAPTFLQLGKVPVPADMTGKSLLPIVEAGKK--DEKPRDYVVLGRERHAFVRRHGL
CONSENSUS     --f----------gv----I------dwlp-Iv-Ia-------------I-g-d-s-II-----

Human_ARS_B   SPRIELLHNIDPNFVDS--------SPCPRNSMAPAKDDSSLPEYSAFNTSWHAA-IRHG
Human_ARS_A   SPRQSLFF--YPSYPDE---------VRGVFAVRTGKYKAHFFTQGSAHSDITADP-ACHA
PARSA_        AQAATAPSRLYKAFTTQGGIRVPALVRYPFRLSRQGAISHAFATVMDVTPTLEDLAGVEHP
ORF_B_[6-0]   GFYLGEHGYFDKREMYDESFRTPLMVRYPFSVKAGSVSNAFAMNLDFAPTLIEDYAGVKIP
ORFC_[NS]     GYPGRAIRTKDYLYDKN------YEPNRWPAGDPPFYGDIDPYMFNWPGETKYYLIEHKD
CONSENSUS     a-----------d--fv---------vr-p----r-g------f-------tsv-a-irh- Human_ARS_B   NWKELTGYPGCGYWFPPPSQKVSEIPSSDPPTKTLWLFDIDRDPEERHDLSREYPHIVT
Human_ARS_A   SSSLTAHEP---------PLLMDESKDPGENYNLLGGVAGATPEVLQALKQLQLLKAQLDA
PARSA_        GKRWRGREIAEPRGRSWLGWLSGETEAAHDENTVTGWELFGMRAIRQGDWKAVYLPAPVG
ORF_B_[6-0]   -ADMQGLSLRPVLDNAGKSPENWRKAVYYHYYEFPSWHMVK-RHYGIRTERYKLHFYND
ORFC_[NS]     DPKWKSFFELGMGKRPAEELEDTNKDPDELHNLAALPEYQKIKQELVAKLRNYLMATKDP
CONSENSUS     --kI-n-----------y-v-kdp----n------w------r--------k-II-----

Human_ARS_B   KLLSRLQFYHKHSVPVYFPAQ-DPRCDPKATGVWGPWM----------------
Human_ARS_A   AVTEGPSQVARGEDPALQDCC-HPGCTPRPACCHCPDPHA---------------
PARSA_        PATWQLYDIEARDPGEIHDEADSQPCKLAELIEHWKRYVSETGVVEGASPFLVR
ORF_B_[6-0]   IDEWELIWDMQKDPHEMQNDYN-DKAYEPIIKDLKVQMKKLQVQYKDTNPTEAL
ORFC_[NS]     RETNGNIQKWDTAAYFSEIDKTPKPSKEMQKRFKLDSSYNYLK----------
CONSENSUS     --tf-I---v-k-----v-I-----pg--p-----------------
```

COMPOSITIONS OF AND METHODS OF USING SULFATASES FROM *FLAVOBACTERIUM HEPARINUM*

RELATED APPLICATIONS

This application is a divisional of U.S. application Ser. No. 12/006,794, filed Jan. 4, 2008, which claims priority under 35 U.S.C. §119 from U.S. provisional application Ser. No. 60/879,272, filed Jan. 5, 2007. The entire contents of both prior applications are herein incorporated by reference.

GOVERNMENT SUPPORT

This invention was made with government support under grant number GM 57073 awarded by the National Institutes of Health. Accordingly, the government has certain rights in the invention.

FIELD OF THE INVENTION

This invention is related, in part, to sulfatase enzymes and methods of their use.

BACKGROUND OF THE INVENTION

Heparan sulfate glycosaminoglycans (HSGAGs) comprise an important polysaccharide constituent of many proteoglycans (Bernfield et al., 1999 *Annu Rev Biochem* 68, 729-777). These glycans are linear polymers based on the variably repeating disaccharide unit (uronic acid α/β1→4 glucosamine)$_n$, where n represents a variably repeating number (typically 10-200). As present in nature, these sugars possess an extensive chemical heterogeneity which is largely attributed to the mosaic arrangement of O- and N-linked sulfates present at different positions along each sugar chain (Esko et al., 2001 *J Clin Invest* 108, 169-173; Sasisekharan et al., 2002 *Nat Rev Cancer* 2, 521-528). Additional structural variations include the presence of N-linked acetates at the glucosamine C2 position as well as the epimerization of the uronic acid C5 carboxylate that distinguishes β-D-glucuronic acid from α-L-iduronic acid. Fundamental to understanding HSGAG structure-activity relationships is the appreciation that the polydispersity of glycan fine structure is not random. Instead, it is the end product of activities regulated in a cell and tissue specific fashion. This programmed diversity of HSGAG structure (Esko et al., 2001 *J Clin Invest* 108, 169-173) ultimately plays out at a functional level, namely through the dynamic regulation of numerous biochemical signaling pathways (Esko et al., 2001 *J Clin Invest* 108, 169-173) relating to such processes as cell growth and differentiation (Sasisekharan et al., 2002 *Nat Rev Cancer* 2, 521-528), cell death (Prince et al., 2002 *Dev Dyn* 223, 497-516; Lai et al., 2004 *Gastroenterology* 126, 231-248), intercellular communication, adhesion and tissue morphogenesis (Hacker et al., 2005 *Nat Rev Mol Cell Biol* 6, 530-541). HSGAGs (present as structurally-defined binding epitopes on the cell surface) also play an important role in microbial pathogenesis (Liu et al., 2002 *J Biol Chem* 277, 33456-33467; Vives et al., 2006 *Curr Gene Ther* 6, 35-44).

In contrast to the complex enzymatic process by which these polysaccharides are made, it appears that their catabolism is more straightforward, both in the scope of its purpose and the means by which it is carried out at the biochemical level. In the mammalian lysosome for example, GAG degradation follows an obligatory sequence of depolymerization steps, using enzymes which follow a predominantly exolytic mode of action. As such, the substrate specificity of one enzyme is largely predicated on the activity of the enzymes which precede it. Essential to this sequence are several sulfohydrolases which desulfate the sugar backbone as a prerequisite to the ensuing glycosidase step. These sulfatases are structure-specific enzymes, each one hydrolyzing a unique sulfate position within the heparin disaccharide repeat unit present at the non-reducing end.

Sequential GAG degradation is not unique to the eukaryotic lysosome. This process has been demonstrated in several microorganisms as well (Dietrich et al., 1973 *J Biol Chem* 248, 6408-6415; Nakamura et al., 1988 *J Clin Microbiol* 26, 1070-1071; Lohse et al., 1992 *J Biol Chem* 267, 24347-24355), which depend on sulfated polysaccharides not only as a carbon source but often as a means of scavenging inorganic sulfate (Kertesz, 2000 *FEMS Microbiol Rev* 24, 135-175). The gram-negative soil bacterium *Flavobacterium heparinum* (a.k.a. *Pedobacter heparinus*) is an excellent example of this process, having also proven to be a particularly rich biological source for the isolation and molecular cloning of several GAG-degrading enzymes (Sasishekaran et al., 1993 *Proc Natl Acad Sci USA* 90, 3660-3664; Godavarti et al., 1996 *Biochem Biophys Res Commun* 225, 751-758). Like the lysosomal pathway, many of the flavobacterial enzymes possess a high degree of substrate specificity.

SUMMARY OF THE INVENTION

The invention relates, in part, to sulfatase enzymes and polypeptides, nucleic acids that encode them, as well as compositions of the aforementioned molecules and methods of their use.

In one aspect a sulfatase enzyme is provided, wherein the sulfatase comprises an amino acid sequence set forth in SEQ ID NO: 2, 4, 17 or 18. In one embodiment, the sulfatase comprises an amino acid sequence set forth in SEQ ID NO: 2. In another embodiment, the sulfatase comprises an amino acid sequence set forth in SEQ ID NO: 4.

In another aspect of the invention, modified sulfatases are provided. In one aspect, the modified sulfatase comprises an amino acid sequence set forth in SEQ ID NO: 2 or 17, wherein at least one amino acid residue has been substituted or deleted, and wherein the at least one amino acid residue that has been substituted or deleted is the residue at position 39, 40, 80, 83, 127, 129, 206, 277, 386 or 503 (said positions are relative to the numbering of the residues in SEQ ID NO: 17). In another aspect, the modified sulfatase comprises an amino acid sequence set forth in SEQ ID NO: 4 or 18, wherein at least one amino acid residue has been substituted or deleted, and wherein the at least one amino acid residue that has been substituted or deleted is the residue at position 39, 80, 83, 128, 175 or 245 (said positions are relative to the numbering of the residues in SEQ ID NO: 18). In other embodiments, the at least one amino acid residue that has been substituted or deleted is any of the residues specifically listed herein, such as in the Examples or as identified by the alignment provided in FIG. 11. In still another aspect, the modified sulfatase comprises an amino acid sequence set forth in SEQ ID NO: 2 or 17, wherein at least one amino acid residue has been substituted or deleted, and wherein the at least one amino acid residue that has been substituted or deleted is not the residue at position 39, 40, 80, 83, 127, 129, 206, 277, 386 or 503. In a further aspect, the modified sulfatase comprises an amino acid sequence set forth in SEQ ID NO: 4 or 18, wherein at least one amino acid residue has been substituted or deleted, and wherein the at least one amino acid residue that has been substituted or deleted is not the residue at position 39, 80, 83, 128, 175 or 245. In further embodiments, the at least one amino acid residue that has been substituted or deleted is not any of the residues specifically listed herein.

In one aspect, the modified sulfatase comprises an amino acid sequence set forth in SEQ ID NO: 2 or 17, wherein at least one amino acid residue has been substituted or deleted, and wherein the at least one amino acid residue that has been substituted or deleted is the residue at position 40, 41, 80, 84, 128, 130, 206, 277, 387 or 504 (said positions are relative to the numbering of the residues in SEQ ID NO: 17). In one embodiment, residue 207 is substituted or deleted. In another embodiment, residue 276 is substituted or deleted. In another aspect, the modified sulfatase comprises an amino acid sequence set forth in SEQ ID NO: 4 or 18, wherein at least one amino acid residue has been substituted or deleted, and wherein the at least one amino acid residue that has been substituted or deleted is the residue at position 40, 80, 84, 129, 176 or 246 (said positions are relative to the numbering of the residues in SEQ ID NO: 18). In other embodiments, the at least one amino acid residue that has been substituted or deleted is any of the residues specifically listed herein, such as in the Examples or as identified by the alignment provided in FIG. 11. In still another aspect, the modified sulfatase comprises an amino acid sequence set forth in SEQ ID NO: 2 or 17, wherein at least one amino acid residue has been substituted or deleted, and wherein the at least one amino acid residue that has been substituted or deleted is not the residue at position 40, 41, 80, 84, 128, 130, 206, 277, 387 or 504 (said positions are relative to the numbering of the residues in SEQ ID NO: 17). In one embodiment, residue 207 has not been substituted or deleted. In another embodiment, residue 276 has not been substituted or deleted. In a further aspect, the modified sulfatase comprises an amino acid sequence set forth in SEQ ID NO: 4 or 18, wherein at least one amino acid residue has been substituted or deleted, and wherein the at least one amino acid residue that has been substituted or deleted is not the residue at position 40, 80, 84, 129, 176 or 246. In further embodiments, the at least one amino acid residue that has been substituted or deleted is not any of the residues specifically listed herein.

In another embodiment, the sulfatase enzyme comprises an amino acid sequence wherein the active site cysteine is in its modified form (FGLy).

In still another embodiment, the sulfatase enzymes provided are substantially pure. In a further embodiment, the sulfatase enzymes provided are isolated. In still a further embodiment, the sulfatase enzymes provided are recombinant.

In another aspect, a method is provided comprising producing or obtaining a modified sulfatase and determining an activity of the modified sulfatase. In one embodiment, the modified sulfatase comprises an amino acid sequence set forth in SEQ ID NO: 2 or 17, wherein at least one amino acid residue has been substituted or deleted, and wherein the at least one amino acid residue that has been substituted or deleted is the residue at position 39, 40, 80, 83, 127, 129, 206, 277, 386 or 503. In another embodiment, the modified sulfatase comprises an amino acid sequence set forth in SEQ ID NO: 4 or 18, wherein at least one amino acid residue has been substituted or deleted, and wherein the at least one amino acid residue that has been substituted or deleted is the residue at position 39, 80, 83, 128, 175 or 245. In still another embodiment, the at least one amino acid residue that has been substituted or deleted is any of the residues specifically listed herein. In a further embodiment, the modified sulfatase comprises an amino acid sequence set forth in SEQ ID NO: 2 or 17, wherein at least one amino acid residue has been substi-tuted or deleted, and wherein the at least one amino acid residue that has been substituted or deleted is not the residue at position 39, 40, 80, 83, 127, 129, 206, 277, 386 or 503. In another embodiment, the modified sulfatase comprises an amino acid sequence set forth in SEQ ID NO: 4 or 18, wherein at least one amino acid residue has been substituted or deleted, and wherein the at least one amino acid residue that has been substituted or deleted is not the residue at position 39, 80, 83, 128, 175 or 245. In further embodiments, the at least one amino acid residue that has been substituted or deleted is not any of the residues specifically listed herein. In another embodiment, the modified sulfatase comprises an amino acid sequence set forth in SEQ ID NO: 2 or 17, wherein at least one amino acid residue has been substituted or deleted, and wherein the at least one amino acid residue that has been substituted or deleted is the residue at position 40, 41, 80, 84, 128, 130, 206, 277, 387 or 504 (said positions are relative to the numbering of the residues in SEQ ID NO: 17). In one embodiment, residue 207 is substituted or deleted. In another embodiment, residue 276 is substituted or deleted. In still another embodiment, the modified sulfatase comprises an amino acid sequence set forth in SEQ ID NO: 4 or 18, wherein at least one amino acid residue has been substituted or deleted, and wherein the at least one amino acid residue that has been substituted or deleted is the residue at position 40, 80, 84, 129, 176 or 246 (said positions are relative to the numbering of the residues in SEQ ID NO: 18). In another embodiment, the at least one amino acid residue that has been substituted or deleted is any of the residues specifically listed herein. In still another embodiment, the modified sulfatase comprises an amino acid sequence set forth in SEQ ID NO: 2 or 17, wherein at least one amino acid residue has been substituted or deleted, and wherein the at least one amino acid residue that has been substituted or deleted is not the residue at position 40, 41, 80, 84, 128, 130, 206, 277, 387 or 504 (said positions are relative to the numbering of the residues in SEQ ID NO: 17). In one embodiment, residue 207 has not been substituted or deleted. In another embodiment, residue 276 has not been substituted or deleted. In a further embodiment, the modified sulfatase comprises an amino acid sequence set forth in SEQ ID NO: 4 or 18, wherein at least one amino acid residue has been substituted or deleted, and wherein the at least one amino acid residue that has been substituted or deleted is not the residue at position 40, 80, 84, 129, 176 or 246. In further embodiments, the at least one amino acid residue that has been substituted or deleted is not any of the residues specifically listed herein.

In yet another embodiment, producing the modified sulfatase includes the step of modifying a nucleic acid or amino acid sequence that encodes the native sulfatase. In still another embodiment, the activity that is determined can be determining the enzyme's activity towards a particular substrate (e.g., the $k_{cat}$ or $K_M$ value (or ratio thereof) or the products of the reaction of the enzyme with the substrate).

In a further aspect, compositions comprising a sulfatase enzyme are also provided. In one embodiment, the compositions further comprise a pharmaceutically acceptable carrier.

In another embodiment, the compositions further comprise calcium.

In a further embodiment, the compositions do not contain a chelator. In another embodiment, the chelator that is not present is EDTA or EGTA. In still another embodiment, the compositions have a concentration of EDTA or EGTA that is less than or equal to 3 mM, 2 mM or 1 mM.

In another embodiment, the compositions provided herein do not contain sulfate ions, phosphate ions or both. In one embodiment, the compositions have a phosphate ion concentration of less than or equal to 5 mM or 2 mM. In another embodiment, the compositions have a sulfate ion concentration of less than or equal to 20 mM.

In yet another embodiment, the compositions provided have a sodium chloride concentration of less than 1 M. In a further embodiment, the compositions have a sodium chloride concentration of less than 0.5 M. In still a further embodiment, the sodium chloride concentration is less than 200 mM.

In still another embodiment, the compositions provided have a pH that is greater than 4.5. In a further embodiment, the pH of the compositions is less than 9. In one embodiment, the pH of the compositions is greater than 4.5 and less than 9. In another embodiment, the pH is in the range of 5-9. In yet another embodiment, the pH is in the range of 6-8. In still another embodiment, the pH is in the range of 5.5-6.5.

In another embodiment, the compositions provided further comprise acetate buffer.

In still another embodiment, the compositions provided further comprise at least one additional polysaccharide-degrading enzyme, such as a GAG-degrading enzyme. In one embodiment, the at least one additional GAG-degrading enzyme is heparinase I, heparinase II, heparinase III, 2-O sulfatase or Δ4,5 glycuronidase. In another embodiment, the at least one additional GAG-degrading enzyme is another sulfatase, glycosyl hydrolase, endoglucuronidase or lyase.

In a further aspect of the invention, compositions are provided that comprise a sulfatase enzyme and a solid support membrane, wherein the sulfatase is immobilized on the solid support membrane.

In still another aspect of the invention, nucleic acid molecules encoding the enzymes or polypeptides of the invention are provided. In one aspect, the nucleic acid is an isolated nucleic acid molecule selected from the group consisting of (a) nucleic acid molecules which hybridize under stringent conditions to a nucleic acid molecule having a nucleotide sequence set forth in SEQ ID NO: 1 or 3 (b) nucleic acid molecules that differ from the nucleic acid molecules of (a) in codon sequence due to degeneracy of the genetic code, and (c) complements of (a) or (b). In one embodiment, the complement is a full complement. In another embodiment the nucleic acid codes for a sulfatase. In yet another embodiment, the isolated nucleic acid molecule has a nucleotide sequence set forth in SEQ ID NO: 1 or a fragment thereof. In another embodiment, the isolated nucleic acid molecule has a nucleotide sequence set forth in SEQ ID NO: 3 or a fragment thereof. In one embodiment, the nucleic acid fragment encodes a polypeptide that has the amino acid sequence of SEQ ID NO: 2, 4, 17 or 18 or an amino acid sequence present therein. In another embodiment, such a polypeptide consists of at least 8, 9, 10, 11, 12, 15, 18, 20, 25, 30, 40, 50, 75, 100, 150, 200, 250, 300, 350, 400, 450 or 550, etc. amino acids (up to the full-length of the enzyme amino acid sequence).

In another aspect of the invention, an expression vector comprising an isolated nucleic acid molecule as provided herein operably linked to a promoter is provided. In a further aspect of the invention, a host cell comprising the expression vector is provided. In still another aspect, compositions comprising the isolated nucleic acid molecule, vector or host cell are provided. In one embodiment, the compositions further comprise a pharmaceutically acceptable carrier.

In another aspect of the invention, methods of degrading monosaccharides or polysaccharides with the molecules provided herein are provided. In one aspect, the methods of degrading comprise contacting a glycosaminoglycan with a sulfatase or composition thereof in an amount effective to degrade the glycosaminoglycan. In one embodiment, the glycosaminoglycan is a HSGAG.

In another aspect of the invention, a degraded monosaccharide or polysaccharide (e.g., a degraded glycosaminoglycan, such as a degraded HSGAG) produced by a method provided herein is provided.

In a further aspect, a composition comprising the degraded monosaccharide or polysaccharide is provided. In another aspect, the composition further comprises a pharmaceutically acceptable carrier.

In still another aspect of the invention, methods of analyzing monosaccharides or polysaccharides with the molecules provided herein are provided. In one aspect, the methods of analyzing comprises contacting a glycosaminoglycan (e.g., a HSGAG) with a sulfatase or composition thereof in an amount effective to analyze the glycosaminoglycan. In one embodiment, the method is a method for identifying the presence of a particular glycosaminoglycan in a sample. In another embodiment, the method is a method for determining the purity of a glycosaminoglycan in a sample. In yet another embodiment, the method is a method for determining the composition of a glycosaminoglycan in a sample. In a further embodiment, the method is a method for determining the sequence of saccharide units in a glycosaminoglycan. In another embodiment, the method further comprises using an analytic technique, such as mass spectrometry, NMR spectroscopy, gel electrophoresis, capillary electrophoresis and/or HPLC.

In one embodiment, any of the methods provided can include contacting with at least one additional polysaccharide-degrading enzyme, such as a glycosaminoglycan-degrading enzyme. In another embodiment, the at least one additional glycosaminoglycan-degrading enzyme is used prior to, subsequent to or concurrently with a 6-O-sulfatase and/or N-sulfamidase. In a further embodiment, the at least one additional glycosaminoglycan-degrading enzyme is heparinase I, heparinse II, heparinase III, 2-O sulfatase or Δ4,5 glycuronidase. In yet a further embodiment, the at least one additional GAG-degrading enzyme is another sulfatase, glycosyl hydrolase, endoglucuronidase or lyase. In one embodiment, the at least one additional glycosaminoglycan-degrading enzyme is Δ4,5 glycuronidase. In another embodiment, the Δ4,5 glycuronidase is contacted with the glycosaminoglycan prior to the 6-O-sulfatase or N-sulfamidase. In a further embodiment, the glycosaminoglycan is contacted with a 2-O sulfatase and the contact with the 2-O sulfatase is prior to the contact with the Δ4,5 glycuronidase. In yet another embodiment, the glycosaminoglycan is contacted with a heparinase and the contact with the heparinase is prior to the contact with the 2-O sulfatase. In another embodiment, the glycosaminoglycan is contacted with 6-O sulfatase and with N-sulfamidase, wherein the glycosaminoglycan is contacted with the 6-O sulfatase prior to the N-sulfamidase. In a further embodiment, the glycosaminoglycan is 3-O desulfated prior to contact with 6-O sulfatase or N-sulfamidase.

In another aspect of the invention, methods of treatment with the compositions provided herein are provided. In one aspect, a method of inhibiting angiogenesis, comprising administering to a subject in need thereof an effective amount of a composition provided herein for inhibiting angiogenesis is provided. In another aspect, a method of treating cancer, comprising administering to a subject in need thereof an effective amount of a composition provided herein for treating cancer is provided. In still another aspect of the invention, a method of inhibiting metastasis, comprising administering to a subject in need thereof an effective amount of a composition provided herein for inhibiting metastasis is provided. In a further aspect, a method of treating a coagulation disorder in a subject, comprising administering a composition provided herein to a subject in need thereof an effective amount for treat the coagulation disorder is provided. In yet another aspect of the invention, a method of treating an inflammatory disorder, comprising administering a composition provided herein to a subject in need thereof an effective amount for treating the inflammatory disorder is provided.

In still another aspect of the invention, compositions and methods for treating the conditions provided herein include an additional therapeutic agent.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 1 provides the flavobacterial 6-O-sulfatase (ORF B) coding sequence. The gene sequence (SEQ ID NO: 1) described as ORF B encodes a polypeptide with 548 amino acids (SEQ ID NO: 19) (545 amino acids starting at the initiating methionine (SEQ ID NO: 17)). The translated protein sequence is highlighted in bold. Numbering of amino acids is noted in parentheses and begins with initiating Met (position noted above corresponding ATG codon). The PFAM sulfatase motif CXPXRXXXXS/TG (SEQ ID NO: 5) is boxed. The predicted signal sequence is overscored with the peptide cleavage site represented by an arrow. Vicinal glutamines (Q) are shaded in gray. The Hind III restriction site is doubled underscored.

FIG. 2 provides the flavobacterial N-sulfamidase (ORF C) coding sequence. The gene sequence, described as ORF C (SEQ ID NO: 3), encodes a polypeptide with 507 amino acids (SEQ ID NO: 20) (500 amino acids starting at the initiating methionine (SEQ ID NO: 18)). The translated protein sequence is highlighted in bold. See FIG. 1 legend for details.

FIG. 3 shows a multiple sequence alignment for ORF B and putative functional assignment as a carbohydrate 6-O-desulfating enzyme. The cloned flavobacterial gene sequence corresponding to ORF B encodes a protein which is a member of a large sulfatase gene family identified by the PFAM sulfatase consensus sequence CXPXRXXXXS/TG (SEQ ID NO: 5). Shown in this representative alignment are the primary amino acid sequences of two bacterial enzymes to which the flavobacterial sequence (as set forth in SEQ ID NO: 17) exhibited the strongest homology: Bacteroides (abbr. Bacter.; SEQ ID NO: 6) and Prevotella sp. (abbr. Prev.; SEQ ID NO: 7) The sequence of the human galactosamine-6-O-sulfatase (Gal-6) is also shown for comparison (SEQ ID NO: 8). The putative functional assignment of the flavobacterial enzyme as a GAG 6-O-sulfatase is based on the functionality of the two bacterial enzymes (especially the Prevotella sp. mucin desulfating enzyme which specifically hydrolyzes the N-acetylglucosamine 6-O-sulfate). Sequence alignment was generated using CLUSTALW (EMBL, Heidelberg, Germany). A consensus sequence is also shown (SEQ ID NO: 21).

FIG. 4 shows a multiple sequence alignment for ORF C and putative functional assignment as a heparan/heparin N-sulfamidase. The cloned flavobacterial gene sequence corresponding to ORF C likewise encodes a protein which is a member of a large sulfatase gene family. As was the case for the 6-O-sulfatase, the functional assignment of the flavobacterial enzyme (as set forth in SEQ ID NO: 20) as a GAG N-sulfamidase is inferred from the putative functionality of the two bacterial enzymes to which it shows the strongest sequence homology: Pirellula sp. (abbr. Pirell.; SEQ ID NO: 9) and Bacteroides (abbr. Bacter.; SEQ ID NO: 22). Also included in this alignment is the primary amino acid sequence of the human lysosomal enzyme, heparin-N-sulfamidase (SEQ ID NO: 10). A consensus sequence is also shown (SEQ ID NO: 23).

FIG. 5 demonstrates the substrate specificity of recombinant 6-O-sulfatase.

FIG. 7 provides sulfatase reaction conditions.

FIG. 8 demonstrates the effect of divalent metals on sulfatase activities.

FIG. 9 demonstrates the sequential degradation of a HSGAG tetrasaccharide using recombinantly expressed flavobacterial enzymes. The ability of the 6-O-sulfatase to hydrolyze the non-reducing end of an oligosaccharide is demonstrated in the context of exo-sequencing the heparin derived tetrasaccharides $\Delta U_{2S}H_{NS,6S}I_{2S}H_{NS,6S}$ and structurally related $\Delta UH_{NS,6S}I_{2S}H_{NS,6S}$ lacking a 2-O-sulfate at the internal iduronic acid position. Sequential treatment of the HSGAG tetrasaccharide was physically assessed after each enzyme step (FIG. 9A-9E) by MALDI-MS. Masses listed in each panel represent either peptide alone (~3216 Da) or oligosaccharide-peptide complex. The net mass of the oligosaccharide is listed in parentheses.

FIG. 11 shows a structure-oriented multiple sequence alignment of cloned flavobacterial sulfatases. The sequence alignment of ORF B (6-O-sulfatase) (as set forth in SEQ ID NO: 17) and ORF C(N-sulfamidase) (as set forth in SEQ ID NO: 18) with the primary sequences of three sulfatases (bacterial arylsulfatase from *Pseudomonas aeruginosa* (PARSA) (SEQ ID NO: 26), human arylsulfatase A (Human ARS A) (SEQ ID NO: 25), and human arylsulfatase B (Human ARS B) (SEQ ID NO: 24), which is actually a N-acetylgalactosamine-4-sulfatase) is shown. Select residues known to comprise the enzyme active site are boxed. The position of the catalytic cysteine modification is noted by an asterisk. A consensus sequence is also shown (SEQ ID NO: 27).

DETAILED DESCRIPTION OF THE INVENTION

Figure 5A:
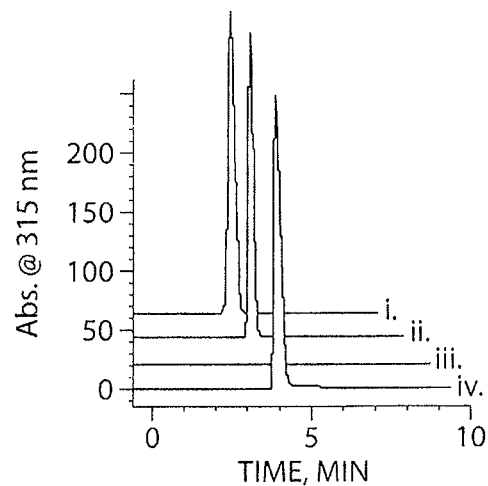
FIG. 5A shows the specificity of the 6-O-sulfatase as a heparin/heparan desulfating enzyme. Desulfation of 4MUGal-6S (i), 4MUGalNAc,6S (ii), or 4MUGlcNAc,6S (iii and iv) by the recombinant 6-O-sulfatase was followed by capillary electrophoresis. Exclusive desulfation of 4MUGlcNAc,6S by 6-O-sulfatase is evidenced by a singular disappearance of absorbance at 315 nm in electrophoretagram (iii) (that normally appears at approximately 4 minutes). Minus enzyme control is shown in (iv). Electrophoretagrams are offset for illustrative purposes.

Previously the cloning, characterization, and recombinant expression in *Escherichia coli* of the *Flavobacterium heparinum* (a.k.a. *Pedobacter heparinus*) 2-O-sulfatase was reported. Two additional sulfatases have been cloned, a 6-O-sulfatase and a N-sulfamidase from the same microorganism. These two enzymes were expressed in *E. coli* in a soluble, active form and their functionality as HSGAG sulfatases was confirmed and their respective kinetic and biochemical properties determined.

The two sulfatase genes described were identified during the process of screening a genomic library with hybridization probes directed toward the flavobacterial 2-O-sulfatase. Two overlapping phagemid clones identified during this process were expanded by chromosomal walking and restriction mapping. Sequence analyses of this genomic region revealed two sizeable open reading frames of 1647 and 1524 base pairs (described hereafter as ORF B and ORF C, respectively). The two gene sequences putatively encode proteins of 545 and 500 amino acids in length (starting at the initiating Met). Neither sequence possessed an obvious Shine-Dalgarno ribosomal binding site within 10 nucleotides of the initiating ATG codon. A closer examination of their respective sequences at the protein level noted several important features. Both flavobacterial ORFs possess a N-terminal hydrophobic signal peptide and corresponding cleavage site sequence predicted by the Von Heijne method for gram-negative bacteria (Nielsen et al., 1997 *Protein Eng* 10, 1-6). Both genes encode basic protein sequences of comparable amino acid composition (by mol percent). Of the two proteins, the ORF B gene product possesses a slightly higher theoretical pI (8.6 vs. 8.0) relative to ORF C. A BLASTP sequence homology search of the two flavobacterial genes against the protein database unambiguously identified both gene products as members of a large sulfatase family (BLASTP, NLM; Bethesda, Md.). Both protein sequences possess the signature PFAM sulfatase motif C/SXPXRXXXXS/TG (SEQ ID NO: 5) as well as the highly conserved sequence LTG (at the +9 through +11 positions relative to this motif). As is the case for many other sulfatases that comprise this large enzyme family, this sulfatase domain is likewise located in the N-terminal region of the encoded polypeptide.

The data presented here demonstrate that both the 6-O-sulfatase and the N-sulfamidase are exolytic enzymes. In addition, in the studies performed, it was found that the 6-O-sulfatase was strongly activated by calcium and inhibited by sulfate and phosphate, while the N-sulfamidase requires calcium but was not apparently inhibited by either sulfate or phosphate. The 6-O-sulfatase was shown to act on either N-sulfated or N-acetylated 6-O-sulfated glucosamines, while being completely inhibited by 3-O-sulfation or unsubstituted amines on the same pyranose ring. The N-sulfamidase was shown to act solely on N-sulfated glucosamines, while being completely inhibited by 3-O or 6-O sulfation. Both enzymes were completely inactive when a glycosidically linked uronic acid was present at the non-reducing C4 position. Taken together with the reported substrate specificities for the previously characterized *F. Heparinum* 2-O-sulfatase and unsaturated glucuronyl hydrolase, the in vitro exolytic sequence for the heparin and heparan sulfate degradation pathway of *F. heparinum* was defined. In addition, these enzymes can be applied in tandem toward the exo-sequencing of heparin-derived oligosaccharides.

The invention provides, in part, 6-O-sulfatase and N-sulfamidase enzymes as well as compositions thereof and methods of their use. Also provided are polypeptides comprising the amino acid sequence of either enzyme as well as nucleic acids that encode them. A polypeptide that comprises the amino acid sequence of 6-O-sulfatase, therefore, can comprise the amino acid sequence provided in FIG. 1 starting at the initiating methionine (SEQ ID NO: 17) or the amino acid sequence of the mature 6-O-sulfatase polypeptide (SEQ ID NO: 2) (i.e., SEQ ID NO: 17 without the signal sequence). Likewise, a polypeptide that comprises the amino acid sequence of N-sulfamidase can comprise the amino acid sequence provided in FIG. 2 starting at the initiating methionine (SEQ ID NO: 18) or the amino acid sequence of the mature N-sulfamidase polypeptide (SEQ ID NO: 4) (i.e., SEQ ID NO: 18 without the signal sequence). Fragments of these polypeptides and compositions that contain them are also provided. In some embodiments the fragments are at least 8, 9, 10, 11, 12, 15, 18, 20, 25, 30, 40, 50, 75, 100, 150, 200, 250, 300, 350, 400, 450, 550, etc. up to the full-length of SEQ ID NO: 2, 4, 17 or 18 minus 1. In some embodiments the cysteine of the cysteine active site of the 6-O-sulfatase or N-sulfamidase is present in its modified form (FGly) in the enzyme or polypeptide provided.

Polypeptides (or enzymes) can be isolated from biological samples, and can also be expressed recombinantly in a variety of prokaryotic and eukaryotic expression systems, such as those described below, by constructing an expression vector appropriate to the expression system, introducing the expression vector into the expression system, and isolating the recombinantly expressed protein. Polypeptides can also be synthesized chemically using well-established methods of peptide synthesis.

The polypeptides (or enzymes) provided herein are in some embodiments isolated or substantially pure. As used herein, "isolated" means the polypeptide or enzyme is separated from its native environment and present in sufficient quantity to permit its identification or use. This means, for example: (i) selectively produced by expression cloning or (ii) purified as by chromatography or electrophoresis. Isolated proteins or polypeptides may be, but need not be, substantially pure. Because an isolated polypeptide or enzyme may be admixed with a pharmaceutically acceptable carrier in a pharmaceutical preparation, the polypeptide or enzyme may comprise only a small percentage by weight of the preparation. The polypeptide or enzyme is nonetheless isolated in that it has been separated from the substances with which it may be associated in living systems, i.e., isolated from other proteins.

As used herein, the term "substantially pure" means that the proteins or polypeptides are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. As used herein, a "substantially pure 6-O-sulfatase or N-sulfamidase" is a preparation of 6-O-sulfatase or N-sulfamidase, respectively, which has been isolated or synthesized and which is greater than about 90% free of contaminants. Preferably, the material is greater than 80%, 85%, 90%, 91%, 92%, 93%, 94%, 95%, 96%, 97%, 98%, or even greater than 99% free of contaminants. The degree of purity may be assessed by means known in the art. One method for assessing the purity of the material may be accomplished through the use of specific activity assays.

Recombinant 6-O-sulfatase or N-sulfamidase enzymes are also provided. As used herein, a "recombinant 6-O-sulfatase or N-sulfamidase" is a 6-O-sulfatase or N-sulfamidase that has been produced through human manipulation of a nucleic acid that encodes the enzyme. The human manipulation usually involves joining a nucleic acid that encodes the 6-O-sulfatase or N-sulfamidase to the genetic material of a different organism and, generally, a different species. "Recombinant" is a term of art that is readily known to one of skill, and techniques for the recombinant expression of 6-O-sulfatase or N-sulfamidase are readily available to those of skill in the art and include those described in Sambrook et al.,
Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998). Other techniques for recombinant expression including examples of expression systems are described further below.

Recombinant technology can also be used to produce modified versions of 6-O-sulfatase or N-sulfamidase. As used herein, "modified" refers to any alteration of the enzyme as compared to the native enzyme (i.e., as it would be found in nature). The modified 6-O-sulfatase, in some embodiments, can comprise an amino acid sequence set forth in SEQ ID NO: 2, wherein at least one amino acid residue has been substituted or deleted, and wherein the at least one amino acid residue that has been substituted or deleted is the residue at position 39, 40, 80, 83, 127, 129, 206, 277, 386 or 503. The modified 6-O-sulfatase, in other embodiments, can comprise an amino acid sequence set forth in SEQ ID NO: 2, wherein at least one amino acid residue has been substituted or deleted, and wherein the at least one amino acid residue that has been substituted or deleted is the residue at position 40, 41, 80, 84, 128, 130, 206, 277, 387 or 504. In another embodiment, the amino acid that has been substituted or deleted is at position 207. In still another embodiment, the amino acid that has been substituted or deleted is at position 276. In other embodiments, the modified 6-O-sulfatase comprises an amino acid sequence set forth in SEQ ID NO: 2, wherein at least one amino acid residue has been substituted or deleted, and wherein the at least one amino acid residue that has been substituted or deleted is not the residue at position 40, 41, 80, 84, 128, 130, 206, 277, 387 or 504. In another embodiment, the amino acid that has not been substituted or deleted is at position 207. In still another embodiment, the amino acid that has not been substituted or deleted is at position 276. In some of these embodiments the cysteine of the cysteine active site is present in its modified form (FGly).

In other embodiments, it is the N-sulfamidase that is modified. For example, the modified N-sulfamidase can comprise an amino acid sequence set forth in SEQ ID NO: 4, wherein at least one amino acid residue has been substituted or deleted, and wherein the at least one amino acid residue that has been substituted or deleted is the residue at position 39, 80, 83, 128, 175 or 245. In another embodiment, the modified N-sulfamidase can comprise an amino acid sequence set forth in SEQ ID NO: 4, wherein at least one amino acid residue has been substituted or deleted, and wherein the at least one amino acid residue that has been substituted or deleted is the residue at position 40, 80, 84, 129, 176 or 246. In a further embodiment, the modified N-sulfamidase can comprise an amino acid sequence set forth in SEQ ID NO: 4, wherein at least one amino acid residue has been substituted or deleted, and wherein the at least one amino acid residue that has been substituted or deleted is not the residue at position 39, 80, 83, 128, 175 or 245. In still a further embodiment, the modified N-sulfamidase can comprise an amino acid sequence set forth in SEQ ID NO: 4, wherein at least one amino acid residue has been substituted or deleted, and wherein the at least one amino acid residue that has been substituted or deleted is not the residue at position 40, 80, 84, 129, 176 or 246. In some of these embodiments the cysteine of the cysteine active site is present in its modified form (FGly).

Based on the understanding of the important residues involved, functional variants can be produced. As used herein, a "functional variant" of a 6-O-sulfatase and N-sulfamidase polypeptide is a polypeptide which contains one or more modifications to the primary amino acid sequence of the 6-O-sulfatase and N-sulfamidase polypeptide, respectively.

The polypeptide can contain 1, 2, 3, 4, 5, 6, 7, 8, 9, 10, 11, 12, 13, 14, 15, 16, 17, 18, 19, 20, 25, 30, 35, 40, 50 or more amino acid modifications. These modifications are intended to encompass modifications that result in a 6-O-sulfatase or N-sulfamidase with altered activity relative to the native 6-O-sulfatase or N-sulfamidase but also include modifications that do not result in altered activity relative to the native enzyme. The term "native" as used herein refers to the 6-O-sulfatase or N-sulfamidase as it would be found in nature. Modifications which create a 6-O-sulfatase or N-sulfamidase polypeptide functional variant are typically made to the nucleic acid which encodes the 6-O-sulfatase or N-sulfamidase polypeptide, and can include deletions, point mutations, truncations, amino acid substitutions and addition of amino acids or non-amino acid moieties to, for example: 1) enhance a property of a 6-O-sulfatase or N-sulfamidase polypeptide, such as protein stability in an expression system or the stability of protein-protein binding; 2) provide a novel activity or property to a 6-O-sulfatase or N-sulfamidase polypeptide, such as addition of a detectable moiety; or 3) to provide equivalent or better interaction with other molecules (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the 6-O-sulfatase or N-sulfamidase amino acid sequences. One of skill in the art will be familiar with methods for predicting the effect on protein conformation of a change in protein sequence, and can thus "design" a functional variant 6-O-sulfatase or N-sulfamidase polypeptide according to known methods. One example of such a method is described by Dahiyat and Mayo in Science 278: 82-87, 1997, whereby proteins can be designed de novo. The method can be applied to a known protein to vary only a portion of the polypeptide sequence. By applying the computational methods of Dahiyat and Mayo, specific variants of a polypeptide can be proposed and tested to determine whether the variant retains a desired conformation.

Functional variants can include 6-O-sulfatase or N-sulfamidase polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a 6-O-sulfatase or N-sulfamidase polypeptide by eliminating proteolysis by proteases in an expression system (e.g., dibasic amino acid residues in yeast expression systems in which KEX2 protease activity is present). Functional variants, therefore, can also include variant 6-O-sulfatase or N-sulfamidase that maintain the same enzymatic function as the native 6-O-sulfatase or N-sulfamidase but include some modification to the amino acid sequence that does not alter native enzyme activity. These modifications include conservative amino acid substitutions as well as non-conservative amino acid substitutions that are remote from the binding and catalytic sites of the enzyme.

Mutations of a nucleic acid which encode a 6-O-sulfatase or N-sulfamidase polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant 6-O-sulfatase or N-sulfamidase polypeptides) which are silent as to the amino acid sequence of the polypeptide, but which provide preferred codons for translation in a particular host. The preferred codons for translation of a nucleic acid in, e.g., $E.\ coli$, are well known to those of ordinary skill in the art. Still other mutations can be made to the noncoding sequences of a 6-O-sulfatase or N-sulfamidase gene or cDNA clone to enhance expression of the polypeptide.

In the description herein, reference is made to the amino acid residues and residue positions of native 6-O-sulfatase or N-sulfamidase (SEQ ID NO: 17 and 18, respectively). In particular, residues and residue positions will be referred to as "corresponding to" a particular residue or residue position of 6-O-sulfatase or N-sulfamidase. As will be obvious to one of ordinary skill in the art, these positions are relative and, therefore, insertions or deletions of one or more residues would have the effect of altering the numbering of downstream residues. In particular, N-terminal insertions or deletions would alter the numbering of all subsequent residues. Therefore, as used herein, a residue in a modified enzyme will be referred to as "corresponding to" a residue of the native enzyme if, using standard sequence comparison programs, they would be aligned. Many such sequence alignment programs are now available to one of ordinary skill in the art and their use in sequence comparisons has become standard (e.g., "LALIGN" available via the Internet at phaedra.crbm.cnrs-mop.fr/fasta/lalign-query.html). As used herein, this convention of referring to the positions of residues of the recombinant modified heparinases by their corresponding 6-O-sulfatase or N-sulfamidase residues shall extend not only to embodiments including N-terminal insertions or deletions but also to internal insertions or deletions (e.g., insertions or deletions in "loop" regions).

One type of amino acid substitution is referred to as a "conservative substitution." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

One skilled in the art will appreciate that the effect can be evaluated by routine screening assays, preferably the biological assays described herein. Modifications of peptide properties including thermal stability, enzymatic activity, hydrophobicity, susceptibility to proteolytic degradation or the tendency to aggregate with carriers or into multimers are assayed by methods well known to the ordinarily skilled artisan. For additional detailed description of protein chemistry and structure, see Schulz, G. E. et al., Principles of Protein Structure, Springer-Verlag, New York, 1979, and Creighton, T. E., Proteins: Structure and Molecular Principles, W.H. Freeman & Co., San Francisco, 1984.

Additionally, some of the amino acid substitutions are non-conservative substitutions. In certain embodiments where the substitution is remote from the active or binding sites, the non-conservative substitutions are easily tolerated provided that they preserve a tertiary structure characteristic of, or similar to, native 6-O-sulfatase or N-sulfamidase, thereby preserving the active and binding sites. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

The enzymes, can be recombinantly produced using a vector including a coding sequence operably joined to one or more regulatory sequences. As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria, in addition to *E. coli, Flavobacterium heparinum, Bacillus, Streptomyces, Pseudomonas, Salmonella, Serratia*, and the like.

To express the enzymes of the invention in a prokaryotic cell, it is desirable to operably join the nucleic acid sequence to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176-182 (1985)) and the ζ-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)).

Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365-404 (1981)).

Because prokaryotic cells may not produce the enzymes of the invention with glycosylation, expression of the enzymes of the invention in eukaryotic hosts is useful when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453-1459 (1988)). Alternatively, baculovirus vectors can be engineered to express large amounts of the enzymes of the invention in insect cells (Jasny, *Science* 238:1653 (1987); Miller et al., In: *Genetic Engineering* (1986), Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals that are temperature-sensitive so that by varying the temperature, expression can be repressed or initiated, or which are subject to chemical (such as metabolite) regulation.

As discussed above, expression of the enzymes of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature* (London) 290:304-310 (1981)); the yeast gal4 gene sequence promoter (Johnston et al., *Proc. Natl. Acad. Sci. (USA)* 79:6971-6975 (1982); Silver et al., *Proc. Natl. Acad. Sci. (USA)* 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the enzyme of the invention does not contain any intervening codons which are capable of encoding a methionine (i.e., AUG). The presence of such codons results either in the formation of a fusion protein (if the AUG codon is in the same reading frame as the enzyme of the invention coding sequence) or a frame-shift mutation (if the AUG codon is not in the same reading frame as the enzyme of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of 6-O-sulfatase and N-sulfamidase mRNA. These elements may include splice signals, as well as transcription promoters, enhancers, and termination signals. cDNA expression vectors incorporating such elements include those described by Okayama, *Molec. Cell. Biol.* 3:280 (1983).

In another embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, and πVX). Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable *Streptomyces* plasmids include pIJ101 (Kendall et al., *J. Bacteriol.* 169:4177-4183 (1987)), and *streptomyces* bacteriophages such as φC31 (Chater et al., In: *Sixth International Symposium on Actinomycetales Biology*, Akademiai Kaido, Budapest, Hungary (1986), pp. 45-54). *Pseudomonas* plasmids are reviewed by John et al. (*Rev. Infect. Dis.* 8:693-704 (1986)), and Izaki (*Jpn. J. Bacteriol.* 33:729-742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 (1982); Bollon et al., *J. Clin. Hematol. Oncol.* 10:39-48 (1980); Maniatis, In: *Cell Biology: A Comprehensive Treatise*, Vol. 3, Gene Sequence Expression, Academic Press, NY, pp. 563-608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. Additionally, DNA or RNA encoding the polypeptides of the invention may be directly injected into cells or may be impelled through cell membranes after being adhered to microparticles. After the introduction of the vector, recipient cells are grown in a selective medium, which selects for the growth of vector-containing cells. Expression of the cloned gene sequence(s) results in the production of polypeptide (or enzyme). This can take place in the transformed cells as such, or following the induction of these cells to differentiate (for example, by administration of bromodeoxyuracil to neuroblastoma cells or the like).

One of skill in the art may also substitute appropriate codons to produce the desired amino acid substitutions by standard site-directed mutagenesis techniques. One may also use any sequence which differs from the nucleic acid equivalents of the nucleic acids that encode the polypeptides of the invention, e.g., SEQ ID NO: 1, SEQ ID NO: 3 or fragments thereof, only due to the degeneracy of the genetic code as the starting point for site directed mutagenesis. The mutated nucleic acid sequence may then be ligated into an appropriate expression vector and expressed in a host such as E. coli.

The invention, therefore, also provides the isolated nucleic acid molecules that code for the 6-O-sulfatase enzymes, N-sulfamidase enzymes or polypeptides as described herein. The term "isolated nucleic acid", as used herein, means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

According to the invention, isolated nucleic acid molecules that code for a 6-O-sulfatase or N-sulfamidase enzyme or polypeptide include: (a) nucleic acid molecules which hybridize under stringent conditions to a nucleotide sequence set forth in SEQ ID NO: 1 or 3, which code for a 6-O-sulfatase or N-sulfamidase (enzyme or polypeptide), respectively; (b) deletions, additions and substitutions of (a) which code for a 6-O-sulfatase or N-sulfamidase (enzyme or polypeptide), respectively, or parts thereof; (c) nucleic acid molecules that differ from the nucleic acid molecules of (a) or (b) in codon sequence due to the degeneracy of the genetic code, and (d) complements of (a), (b) or (c) (e.g., full complements). The isolated nucleic acid molecules include, in some embodiments, isolated nucleic acid molecules that code for a 6-O-sulfatase or N-sulfamidase (enzyme or polypeptide) which has an amino acid sequence set forth as SEQ ID NOs: 2 or 4, respectively.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating 6-O-sulfatase or N-sulfamidase polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The isolated nucleic acid molecules of the invention are also intended to encompass homologs and alleles which can be identified by conventional techniques. Identification of human and other organism homologs of 6-O-sulfatase or N-sulfamidase polypeptides will be familiar to those of skill in the art. In general, nucleic acid hybridization is a suitable method for identification of homologous sequences of another species, which correspond to a known sequence. Standard nucleic acid hybridization procedures can be used to identify related nucleic acid sequences of selected percent identity. For example, one can construct a library of cDNAs reverse transcribed from the mRNA of a sample and use the nucleic acids that encode a 6-O-sulfatase or N-sulfamidase identified therein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "stringent conditions" as used herein refers to parameters with which the art is familiar. Such parameters include salt, temperature, length of the probe, etc. The amount of resulting base mismatch upon hybridization can range from near 0% ("high stringency") to about 30% ("low stringency"). Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM NaH2PO4 (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

The skilled artisan also is familiar with the methodology for screening cells for expression of such molecules, which then are routinely isolated, followed by isolation of the pertinent nucleic acid. Thus, homologs and alleles of the 6-O-sulfatase and N-sulfamidase of the invention, as well as nucleic acids encoding the same, may be obtained routinely, and the invention is not intended to be limited to the specific sequences disclosed. It will be understood that the skilled artisan will be able to manipulate the conditions in a manner to permit the clear identification of homologs and alleles of the 6-O-sulfatase and N-sulfamidase nucleic acids of the invention. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 90% nucleotide identity and/or at least 95% amino acid identity to the sequences of the 6-O-sulfatase nucleic acids or N-sulfamidase nucleic acids or polypeptides, respectively. In some instances at least 95% nucleotide identity and/or at least 97% amino acid identity is shared. In other instances at least 97% nucleotide identity and/or at least 98% amino acid identity is shared, while in other instances at least 99% nucleotide identity and/or at least 99% amino acid identity is shared. In still other instances at least 99.5% nucleotide identity and/or at least 99.5% amino acid identity is shared. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for the 6-O-sulfatase or N-sulfamidase related genes, such as homologs and alleles of the 6-O-sulfatase and N-sulfamidase, a Southern blot may be performed using the foregoing conditions, together with a radioactive probe. After washing the membrane to which the DNA is finally transferred, the membrane can be placed against X-ray film or a phosphoimager plate to detect the radioactive signal.

The present invention also provides for the use of the 6-O-sulfatase and N-sulfamidase molecules provided as enzymatic tools. The molecules include those with the native sequence as well as molecules that are fragments or functional variants of the native. A "native 6-O-sulfatase or N-sulfamidase specific activity" is the measure of enzymatic activity of native 6-O-sulfatase or N-sulfamidase obtained from cell lysates of *F. heparinum*. Therefore, based on the disclosure provided herein, those of ordinary skill in the art will be able to identify other 6-O-sulfatase or N-sulfamidase enzymes having altered enzymatic activity with respect to the native 6-O-sulfatase or N-sulfamidase, such as functional variants. The term "specific activity" as used herein refers to the enzymatic activity of a preparation of 6-O-sulfatase or N-sulfamidase.

The methods that may be used to test the specific activity of the 6-O-sulfatase and N-sulfamidase of the present invention are known in the art, e.g., those described in the Examples or as identified by the alignment provided in FIG. 11. These methods may also be used to assess the function of variants and functionally active fragments of 6-O-sulfatase or N-sulfamidase. For example, the $k_{cat}$ value may be determined using any enzymatic activity assay to assess the activity of a 6-O-sulfatase or N-sulfamidase enzyme. Several such assays are well-known in the art. For instance, an assay for measuring $k_{cat}$ is described in Ernst, S. E., Venkataraman, G., Winkler, S., Godavarti, R., Langer, R., Cooney, C. and Sasisekharan. R. (1996) Biochem. J. 315, 589-597. Therefore, based on the disclosure provided herein, those of ordinary skill in the art will be able to identify other 6-O-sulfatase or N-sulfamidase molecules having enzymatic activity that is similar to or altered in comparison with the native 6-O-sulfatase or N-sulfamidase molecule, such as 6-O-sulfatase or N-sulfamidase functional variants.

The activity of an enzyme can also be assessed according to its "product profile" (i.e., a characterization of the enzymatic products that result from contact of the enzyme with a monosaccharide or polysaccharide or a sample containing the monosaccharide or polysaccharide). The product profile may be determined by any method known in the art for examining the type or quantity of degradation products produced by a 6-O-sulfatase or N-sulfamidase alone or in combination with other enzymes. One preferred method for determining the type and quantity of product is described in Rhomberg, A. J. et al., *PNAS*, v. 95, p. 4176-4181, (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HSGAGs to produce HSGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative.

Other methods for assessing the product profile may also be utilized. For instance, other methods include methods which rely on parameters such as viscosity (Jandik, K. A., Gu, K. and Linhardt, R. J., (1994), *Glycobiology*, 4:284-296) or total UV absorbance (Ernst, S. et al., (1996), *Biochem. J.*, 315:589-597) or mass spectrometry or capillary electrophoresis alone.

The 6-O-sulfatase and N-sulfamidase of the invention are useful as tools for degrading and/or analyzing monosaccharides (e.g., a monosaccharide of a GAG) or polysaccharides, such as sulfated polysaccharides (e.g., GAGs). The invention, therefore, includes a variety of in vitro, in vivo and ex vivo methods in which it is useful to degrade or analyze monosaccharides or polysaccharides or to determine whether or not monosaccharides or polysaccharides can be degraded. Such methods, in some embodiments, include the step of contacting a monosaccharide or polysaccharide or sample containing monosaccharides or polysaccharides with a 6-sulfatase or N-sulfamidase (or composition thereof) of the invention. The methods can further include steps whereby the sample or portion thereof is then analyzed with an analytic technique to determine the result of the contacting (e.g., the products formed or not formed).

In any of the methods provided the 6-O-sulfatase or N-sulfamidase can be used alone or with other polysaccharide-degrading enzymes, such as GAG-degrading enzymes. "GAG-degrading enzymes" refer to enzymes that degrade a glycosaminoglycan and include but are not limited to heparinase I, heparinase II, heparinase III, 2-O sulfatase, Δ4,5 glycuronidase, other sulfatases, glycosyl hydrolases, endoglucuronidases, α-glucosidase, β-glucosidase, other lyases, modified versions of these enzymes, variants and functionally active fragments thereof. In particular, in some embodiments, 6-O-sulfatase or N-sulfamidase can be used subsequent to or concomitantly with a heparinase, 2-O-sulfatase, Δ4,5 glycuronidase, or all or some combination of these enzymes, to degrade and/or analyze a monosaccharide or polysaccharide. In addition, in some embodiments, N-sulfamidase is used subsequent to or concomitantly with 6-O-sulfatase.

As used herein the terms "glycosaminoglycan" and "GAG" are used interchangeably to refer to a family of molecules, which include HSGAGs that are molecules having heparin-like/heparan sulfate-like structures and properties. These molecules include but are not limited to low molecular weight heparin (LMWH), heparin, biotechnologically prepared heparin, chemically modified heparin, synthetic heparin and heparan sulfate. The term "biotechnological heparin" encompasses heparin that is prepared from natural sources of polysaccharides which have been chemically modified and is described for example in Razi et al., Bioche. J. 1995 Jul. 15; 309 (Pt 2): 465-72. Chemically modified heparin is described in Yates et al., Carbohydrate Res (1996) Nov. 20; 294:15-27, and is known to those of skill in the art. Synthetic heparin is well known to those of skill in the art and is described in Petitou, M. et al., Bioorg Med Chem. Lett. (1999) Apr. 19; 9(8):1161-6.

In some embodiments, the GAG, such as a HSGAG, or monosaccharide thereof is or contains a N-sulfated or N-acetylated 6-O-sulfated glucosamine. In further embodiments, the GAG or monosaccharide thereof is sulfated or acetylated at the 2-amino position. In other embodiments the GAG or monosaccharide thereof does not contain 3-O sulfation, 6-O sulfation or does not contain both. In another embodiment, the GAG, such as a HSGAG, or monosaccharide thereof does not contain an unsubstituted amine on the same pyranose ring. In still another embodiment, the GAG, such as a HSGAG, does not contain a glycosidically linked uronic acid at the non-reducing C4 position. In yet another embodiment, the GAG, such as a HSGAG, or monosaccharide thereof is not unsaturated. In other embodiments, the GAG, such as a HSGAG, or monosaccharide thereof is any of the specific substrates used in the analysis described further below in the Examples.

The 6-O-sulfatase and N-sulfamidase of the invention may be used, for example, as a tool to sequence polysaccharides. Detailed methods for sequencing polysaccharides and other polymers are disclosed in U.S. patent application Ser. Nos. 09/557,997 and 09/558,137. These methods utilize tools such as GAG-degrading enzymes in the sequencing process. The 6-O-sulfatase and N-sulfamidase of the invention are useful as such a tool. Briefly, the method is performed by enzymatic digestion, followed by mass spectrometry and capillary electrophoresis. In the example described in the Rhomberg reference, enzymatic reactions are performed by adding 1 microliter of enzyme solution to 5 microliter of substrate solution. The digestion is then carried out at room temperature (22° C.), and the reaction is stopped at various time points by removing 0.5 microliter of the reaction mixture and adding it to 4.5 microliter of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199-204). A two-fold lower access of basic peptide $(Arg/Gly)_{15}$ is premixed with matrix before being added to the oligosaccharide solution. A 1 microliter aliquot of sample/matrix mixture containing 1-3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide. Capillary electrophoresis may then be performed on a Hewlett-Packard$^{3D}$ CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 233 nm and an extended light path cell (Hewlett-Packard). The electrolyte is a solution of 10 microliter dextran sulfate and 50 millimolar Tris/phosphoric acid (pH 2.5). Dextran sulfate is used to suppress nonspecific interactions of the glycosaminoglycan oligosaccharides with a silica wall. Separations are carried out at 30 kV with the anode at the detector side (reversed polarity). A mixture of a 1/5-naphtalenedisulfonic acid and 2-naphtalene-sulfonic acid (10 micromolar each) is used as an internal standard.

Additionally, the coupling of CE and MALDI-MS with enzymes and a bioinformatics-based, property-encoded nomenclature (PEN) have led to a sequencing strategy (PEN-MALDI) described in (Venkataraman, G., Shriver, Z., Raman, R., and Sasisekharan, R. (1999) Science 286, 537-42). Other analytic techniques for use in sequencing (or analyzing generally) polysaccharides or monosaccharides are known in the art and include the use of 1 and 2D NMR, ion exchange HPLC, gel electrophoresis, etc. An analysing step of any of the methods provided herein can include the use of any of the analytic techniques listed herein or otherwise known in the art.

The 6-O-sulfatase and N-sulfamidase of the invention can also be used in other methods of analyzing monosaccharides, polysaccharides or samples containing them. Such methods include methods for identifying the presence of a particular monosaccharide or polysaccharide in a sample, methods for determining the purity of a monosaccharide or polysaccharide in a sample, methods for determining the composition of a polysaccharide in a sample, etc. A "sample", as used herein, refers to any sample that may contain a monosaccharide or polysaccharide.

In another aspect of the invention, it was found that the activity of 6-O-sulfatase and N-sulfamidase can be affected by pH as well as the presence of sodium chloride, sulfate, phosphate, calcium or chelators. Therefore, compositions of 6-O-sulfatase and N-sulfamidase are provided in which the composition is of a certain pH. The pH can be for example greater than 4.5 or less than 9 or both. In some embodiments the pH is in the range of 5-9, 6-8 or 5.5-6.5. In still other embodiments, the pH is 5, 5.5, 6, 6.5, 7, 7.5, 8, 8.5 or 9.

Compositions are also provided wherein the composition further comprises calcium. Compositions are further provided where in the composition does not comprise a chelator. In some embodiments, the compositions that do not contain a chelator also do not contain calcium. Chelators are known in the art and include, for example, EDTA and EGTA. In some embodiments, the chelator is at a concentration of less than 5 mM, less than 4 mM, less than 3 mM, less than 2 mM, less than 1.5 mM, less than 1 mM, less than 0.5 mM, etc. In some embodiments, the chelator is present at a concentration of 5 mM, 4 mM, 3 mM, 2 mM, 1.5 mM, 1 mM, or 0.5 mM, etc.

Compositions are further provided wherein the composition does not comprise sulfate ions, phosphate ions or both. In some embodiments, the sulfate ions are present at a concentrations of less than 20 mM, less than 19 mM, less than 18 mM, less than 17 mM, less than 16 mM, less than 15 mM, less than 14 mM, less than 13 mM, less than 12 mM, less than 11 mM, less than 10 mM, less than 9 mM, less than 8 mM, less than 7 mM, less than 6 mM, less than 5 mM, less than 4 mM, less than 3 mM, less than 2 mM, or less than 1 mM, etc. In other embodiments, the sulfate ions are present at a concentration of between 5-20 mM. In still other embodiments, the composition comprises phosphate ions at a concentration that is less than or equal to 5 mM, less than 4 mM, less than 3 mM, less than 2 mM, or less than 1 mM, etc.

Compositions are also provided wherein the composition has a concentration of sodium chloride that is less than 1 M, less than 0.9 M, less than 0.8 M, less than 0.7 M, less than 0.6 M, less than 0.5 M, less than 0.4 M, less than 0.3 M, less than 0.2 M, or less than 0.1 M, etc. In still other embodiments the concentration of sodium chloride is between 0.5 M and 1 M.

Compositions are also provided in which the composition further comprises acetate buffer.

In addition, methods of degrading or analyzing monosaccharides or polysaccharides with such compositions or in the presence or absence of the above compounds are also provided.

One of ordinary skill in the art, in light of the present disclosure, is enabled to produce substantially pure preparations of degraded monosaccharide or polysaccharide compositions utilizing the a 6-O-sulfatase or N-sulfamidase enzymes alone or in conjunction with other polysaccharide-degrading enzymes. The preparations can be prepared from HSGAG sources. A "HSGAG source" as used herein refers to heparin-like/heparan sulfate-like glycosaminoglycan compositions which can be manipulated to produce degraded products using standard technology, including enzymatic degradation, etc. As described above, HSGAGs include but are not limited to isolated heparin, chemically modified heparin, biotechnology prepared heparin, synthetic heparin, heparan sulfate, and LMWH. The HSGAGs sources can be natural sources, prepared by direct synthesis, etc.

The enzymatic compositions of the invention may also be used to remove active monosaccharides or polysaccharides (e.g., GAGs, such as HSGAGs) from a fluid (e.g., a GAG containing fluid, such as a HSGAG containing fluid). A fluid is contacted with the 6-O-sulfatase or N-sulfamidase of the invention, alone or in combination with other enzymes. The method is particularly useful for the ex vivo removal of GAGs, such as HSGAGs, from blood. In one embodiment of the invention the 6-O-sulfatase or N-sulfamidase is immobilized on a solid support as is conventional in the art. The solid support containing the immobilized 6-O-sulfatase or N-sulfamidase may be used in extracorporeal medical devices (e.g. hemodialyzer, pump-oxygenator) for systemic heparinization to prevent the blood in the device from clotting. The support membrane containing immobilized 6-O-sulfatase or N-sulfamidase is positioned at the end of the device to neutralize the GAG, such as a HSGAG, before the blood is returned to the body.

The 6-O-sulfatase or N-sulfamidase may be immobilized to any type of support but if the support is to be used in vivo or ex vivo it is desired that the support is sterile and biocompatible. A biocompatible support is one which would not cause an immune or other type of damaging reaction when used in a subject. The 6-O-sulfatase or N-sulfamidase may be immobilized by any method known in the art. Many methods are known for immobilizing proteins to supports. A "solid support" as used herein refers to any solid material to which a polypeptide can be immobilized.

Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

It has been recognized that cells synthesize distinct GAG sequences and decorate themselves with these sequences, using the extraordinary information content present in the sequences to bind specifically to many signaling molecules and thereby regulate various biological processes. The compositions of the invention, therefore, have many therapeutic utilities. The invention is useful in a variety of in vitro, in vivo and ex vivo methods in which therapies are useful. The compositions include the enzymatic compositions provided as well as the compositions that contain a degraded GAG, such as a degraded HSGAG, or monosaccharide thereof. A "degraded GAG" as used herein refers to a molecule or molecules which are degraded GAGs or pieces or fragments thereof that have been degraded through the use of the enzymatic compositions provided herein. Such compounds may be generated using an enzymatic composition or they may be synthesized de novo. Degraded GAG fragments, such as degraded HSGAG fragments, including monosaccharides, can be tested for therapeutic activity using any of the assays described herein or known in the art.

The compositions of the invention can be used for the treatment of any type of condition in which such therapy has been identified as or can be determined to be a useful therapy, such as for treating coagulation disorders, treating cancer, treating inflammatory disorders, inhibiting angiogenesis, preventing neovascularization, inhibiting metastasis, regulating apoptosis, etc. One of ordinary skill in the art is enabled to prepare or identify an appropriate therapeutic composition, depending on the subject and the disorder being treated. These compositions may be used alone or in combination with other therapeutics.

The invention is useful for treating and/or preventing any disease/condition in a subject whereby glycosaminoglycans have been found to be important in the development and/or progress of the disease. The terms "treat" and "treating" as used herein refers to reversing or blocking the progression of the disease in the subject. Treating a disease also includes exacting a desired improvement in the disease or symptoms of the disease. For example to treat a subject with tumor cell proliferation refers to inhibiting completely or partially the proliferation or metastasis of a cancer or tumor cell, as well as inhibiting or preventing any increase in the proliferation or metastasis of a cancer or tumor cell.

A "subject having a disease" is a subject that can be diagnosed as having the disease, e.g., a person having cancer is identified by the presence of cancerous cells. A "subject at risk of having a disease" as used herein is a subject who has a high probability of developing the disease. These subjects include, for instance, subjects having a genetic abnormality, the presence of which has been demonstrated to have a correlative relation to a higher likelihood of developing the disease. For diseases brought about by exposure to disease causing agents, subjects at risk are those who are exposed to the disease causing agents such as tobacco, asbestos, chemical toxins, viruses, parasites, etc. A subject at risk also includes those who have previously been treated for the disease and have the possibility of having a recurrence of the disease. When a subject at risk of developing a disease is treated with a composition of the invention, the subject is able to prevent the occurrence of the disease or reduce the possibility of developing the disease.

The compositions are useful for treating or preventing disorders associated with coagulation. A "disease associated with coagulation" or "coagulation disorder" as used herein refers to a condition characterized by an interruption in the blood supply to a tissue due to a blockage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

A disease associated with coagulation as used herein also is intended to encompass atherosclerosis. Atherosclerosis is a disease of the arteries whereby blood flow can be reduced due to the development of atheromatous plaques along the interior walls of the arteries. These plaques begin by the initial deposition of cholesterol crystals which grow larger with time. In addition to the cholesterol deposition, plaques also grow due to the proliferation of the surrounding cells. In time, the artery may become completely occluded due to this plaque growth.

The compositions may be used alone or in combination with a therapeutic agent for treating a disease associated with coagulation. Examples of therapeutics useful in the treatment of diseases associated with coagulation include anticoagulation agents, antiplatelet agents and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v. 25 (7 suppl), p. 10S-17S (1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. et al., 1991, *J. Biol. Chem.* 266(8):5191-5201, the entire contents of which are hereby incorporated by reference.

The compositions of the invention are also useful for inhibiting angiogenesis. An effective amount for inhibiting angiogenesis of the preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of a preparation which is sufficient to diminish the number of blood vessels growing into a tumor. This amount can be assessed in an animal model of tumors and angiogenesis, many of which are known in the art.

The compositions of the invention are also useful for treating and preventing cancer cell metastasis. The invasion and metastasis of cancer is a complex process which involves changes in cell adhesion properties which allow a transformed cell to invade and migrate through the extracellular matrix (ECM) and acquire anchorage-independent growth properties (Liotta, L. A., et al., Cell 64:327-336, 1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus, the enzymatic compositions or degradation products thereof can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer, 1992, 52:378-383. Matrigel is a reconstituted basement membrane containing type IV collagen, laminin, heparan sulfate proteoglycans such as perlecan, which bind to and localize bFGF, vitronectin as well as transforming growth factor-β (TGF-β) urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

According to another aspect of the invention, there is provided methods for treating subjects having or at risk of having cancer. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

When administered to a patient undergoing cancer treatment, the compounds may be administered in cocktails containing other anti-cancer agents. The compounds may also be administered in cocktails containing agents that treat the side-effects of radiation therapy, such as anti-emetics, radiation protectants, etc.

Anti-cancer drugs that can be co-administered with the compounds of the invention include, but are not limited to, Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

The compositions of the invention can also be used to treat a subject with an inflammatory disorder. In some embodiments the inflammatory disorder is non-autoimmune inflammatory bowel disease, post-surgical adhesions, coronary artery disease, hepatic fibrosis, acute respiratory distress syndrome, acute inflammatory pancreatitis, endoscopic retrograde cholangiopancreatography-induced pancreatitis, burns, atherogenesis of coronary, cerebral and peripheral arteries, appendicitis, cholecystitis, diverticulitis, visceral fibrotic disorders, wound healing, skin scarring disorders (keloids, hidradenitis suppurativa), granulomatous disorders (sarcoidosis, primary biliary cirrhosis), asthma, pyoderma gandrenosum, Sweet's syndrome, Behcet's disease, primary sclerosing cholangitis or an abscess. In still another embodiment the inflammatory condition is an autoimmune condition. The autoimmune condition in some embodiments is rheumatoid arthritis, rheumatic fever, ulcerative colitis, Crohn's disease, autoimmune inflammatory bowel disease, insulin-dependent diabetes mellitus, diabetes mellitus, juvenile diabetes, spontaneous autoimmune diabetes, gastritis, autoimmune atrophic gastritis, autoimmune hepatitis, thyroiditis, Hashimoto's thyroiditis, insulitis, oophoritis, orchitis, uveitis, phacogenic uveitis, multiple sclerosis, myasthenia gravis, primary myxoedema, thyrotoxicosis, pernicious anemia, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, sympathetic opthalmia, idiopathic thrombocylopenic purpura, idiopathic feucopenia, Siogren's syndrome, Wegener's granulomatosis, poly/dermatomyositis or systemic lupus erythematosus.

The compositions provided thus can also include anti-inflammatory agents. Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; and Zomepirac Sodium.

HSGAGs (along with collagen) are key components of the cell surface-extracellular matrix (ECM) interface. While collagen-like proteins provide the necessary extracellular scaffold for cells to attach and form tissues, the complex polysaccharides fill the space created by the scaffold and act as a molecular sponge by specifically binding and regulating the biological activities of numerous signaling molecules like growth factors, cytokines etc. Therefore, the compositions provided herein can also be used in methods of repairing tissues.

Each of these disorders mentioned herein is well-known in the art and is described, for instance, in *Harrison's Principles of Internal Medicine* (McGraw Hill, Inc., New York), which is incorporated by reference.

The invention also encompasses screening assays for identifying other compounds for the treatment of a tumor and for preventing metastasis. The assays can be accomplished, for example, by treating a tumor or isolated tumor cells with an enzymatic composition as provided herein and isolating the resultant degraded GAGs, such as degraded HSGAGs. Thus, the invention encompasses individualized therapies, in which a tumor or portion of a tumor is isolated from a subject and used to prepare the therapeutic degraded GAGs, such as degraded HSGAGs. These therapeutic GAGs can be re-administered to the subject to protect the subject from further tumor cell proliferation or metastasis or from the initiation of metastasis if the tumor is not yet metastatic. Alternatively the GAGs can be used in a different subject having the same type or tumor or a different type of tumor.

The compounds provided herein may also be linked to a targeting molecule. A targeting molecule is any molecule or compound which is specific for a particular cell or tissue and which can be used to direct the compound to the cell or tissue. Preferably, in some embodiments, the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Effective amounts of the compounds of the invention are administered to subjects in need of such treatment. Effective amounts are those amounts which will result in a desired improvement in the condition or symptoms of the condition, e.g., for cancer, this can be a reduction in cellular proliferation or metastasis, without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise the compounds of the invention with one or more pharmaceutically acceptable carriers and optionally other therapeutic ingredients. The term "pharmaceutically-acceptable carrier" as used herein, means one or more compatible solid or liquid filler, diluants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being comingled with the compounds of the present invention or other compositions, and with each other, in a manner such that there is no interaction which would substantially impair the desired pharmaceutical efficiency.

A variety of administration routes are available. The particular mode selected will depend, of course, upon the particular active agent selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. A preferred mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, and transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above.

The pharmaceutical compositions are suitable for use in a variety of drug delivery systems. For a brief review of methods for drug delivery, see Langer, Science 249:1527-1533, 1990, which is incorporated herein by reference.

The compositions may conveniently be presented in unit dosage form and may be prepared by any of the methods well known in the art of pharmacy. All methods include the step of bringing the active compound into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The compositions may be stored lyophilized.

Other delivery systems can include time-release, delayed release or sustained release delivery systems. Such systems can avoid repeated administrations of the heparinases of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. No. 4,748,034 and U.S. Pat. No. 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

A subject is any human or non-human vertebrate, e.g., dog, cat, horse, cow, pig.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Reagents

Fluorescent glucopyranoside substrates 4-methyllumbelliferyl-α/β-D-glucopyranoside (4-MU-α-D-Glc, 4-MU-β-D-Glc) were purchased from EMD Biosciences, Inc (San Diego, Calif.). 6-O and N-sulfated fluorogenic glycopyranoside derivatives were obtained through Toronto Research Chemicals (Toronto, Canada). Glucosamine and galactosamine monosaccharides, arylsulfate substrates 4-catecholsulfate and 4-methyllumbelliferyl-sulfate were purchased from Sigma Chemical Co. (St. Louis, Mo.). Exoglucosidases were purchased from MP Biomedicals (Irvine, Calif.). Materials for genomic library construction and screening were obtained from Stratagene (La Jolla, Calif.). PCR enzymes, TOP10 chemically competent cells, and oligonucleotide primers were obtained from Invitrogen (Carlsbad, Calif.). Additional molecular cloning reagents were purchased from New England Biolabs (Beverly, Mass.) or the manufacturers listed.

Molecular Cloning of Flavobacterial 6-O-Sulfatase and N-Sulfamidase

Both flavobacterial sulfatase genes were cloned by PCR from a λZAPII flavobacterial genomic library originally screened using DNA hybridization probes specific to 2-O-sulfatase. Library construction, hybridization screening, and phage excision were as described. Two overlapping clones were expanded by chromosomal walking and restriction mapping using the Lambda DASH II genomic cloning kit (Stratagene, La Jolla, Calif.) for the ligation of size fractionated genomic DNA (generated by a partial Sau3A I digestion). 2-O-sulfatase positive clones from an amplified library were plaque purified through three successive rounds and the DNA purified from a high titer lysate using standard techniques (Ausubel et al., eds. 1987 Current Protocols in Molecular Biology, John Wiley and Sons, NY, N.Y.). For DNA sequencing, recombinant phage DNA was subcloned into pBluescript SK+/− (Stratagene, La Jolla, Calif.). The coding sequences of two putative sulfatase genes (described as ORF B and ORF C) were identified by the canonical PFAM sulfatase family identifier (CXPXRXXXXS/TG; SEQ ID NO: 5) and subsequently PCR amplified using the following primer sets: 1) for ORF B (6-O-sulfatase), 5' GAA TT CATATGG GTA AAT TGA AAT TAA TTT TA 3' (forward; SEQ ID NO: 11) and 5' GGA TCCTCGAGT TAT AAA GCT TCA GTT GGA TTC GT 3' (reverse; SEQ ID NO: 12) for ORF C(N-sulfamidase), 5' TCT AGA CATATG AAA TTT AAC AAA TTG AAA TAT TTC 3' (forward; SEQ ID NO: 13) and 5' GGA TCCTCGAGT TAC TTC AAA TAA TTG TAA CTG GAA T 3' (reverse; SEQ ID NO: 14). Amplified genes were subcloned into the T7-based bacterial expression vector pET28a (Novagen, San Diego, Calif.) as an Nde 1-Xho 1 cassette (restriction sites underlined). Cloning, as such, allowed these genes to be expressed as an $NH_2$-terminal 6×His fusion with an intervening thrombin cleavage site for facile removal of this tag following protein purification.

Bacterial Expression and Protein Purification

Recombinant protein expression in the E. coli strain BL21 (DE3) and one-step affinity purification by nickel chelation chromatography were as described for 2-O-sulfatase (Myette et al., 2003 J Biol Chem 278, 12157-12166). The prediction of $NH_2$-terminal signal sequences and putative cleavage sites for the two respective proteins was made by the Von Heijne computational method (Nielsen et al., 1997 Protein Eng 10, 1-6.). Engineering and expression of these truncated proteins (minus signal sequences) were as described above for the full-length genes with the exception of substituting the 5' primers which were used in the original PCR amplification step. These internal primers included 5' TCT AGA CATATG TCT TGC CAG CAG CCT AAA C 3' (for ORF B; SEQ ID NO: 15) and 5' TCT AGA CATATG TCC TGC ACT TCG CCG GAA 3' (for ORF C; SEQ ID NO: 16), with the Nde 1 site underlined. As such, the ORF B gene sequence begins at Met 18 (FIG. 1). Likewise, the ORF C gene sequence begins at Ser 21 (FIG. 2). Removal of the 6×His tag was achieved by site-specific protease cleavage using the thrombin cleavage capture kit (Novagen, San Diego, Calif.). Proteolysis conditions were generally as described for other recombinantly expressed flavobacterial heparin degrading enzymes. Following concentrating the enzymes by ultrafiltration, cleaved proteins were dialyzed overnight against 4 liters of 50 mM Tris, pH 7.5 and 0.1 M NaCl, 4° C., using a 3 mL slide-a-lyzer cassette with a 10,000 molecular weight cutoff (MWCO) (Pierce Chemical, Rockland, Ill.).

Final protein concentrations were determined colorimetrically using the Bradford Assay (Bio-Rad, Hercules, Calif.) and confirmed by UV absorption spectroscopy using theoretical molar extinction coefficients ($\epsilon_{280}$) of 94,730 M$^{-1}$ (61,572 Da) and 86,340 (53,193 Da) for the NH$_2$-terminally truncated ORF B (6-O-sulfatase) and ORF C(N-sulfamidase), respectively. These values were calculated for thrombin-cleaved proteins lacking a 6×His purification tag. Enzymes were stored at 4° C. at a concentration of ~10 mg/mL. Full enzyme activity was retained for several months under these conditions.

Arylsulfatase Assay

Arylsulfatase activity was measured independently using two chromogenic substrates, 4-catechol-sulfate and 4-methylumbelliferyl-sulfate (4-MUS). The catechol substrate assay was conducted generally as described (Beil et al., 1995 *Eur J Biochem* 229, 385-394). Briefly, 10 mM substrate were incubated with ~30 µM recombinant enzyme overnight (12-15 hours) at 37° C. in a 100 µL reaction which included 50 mM MES pH 7.0 and +2 mM CaCl$_2$. Reactions were quenched by the addition of 5 µL 5M NaOH and colorimetric activity determined spectroscopically at 515 nm. Fluorimetric arylsulfatase assay using 4-MUS was as described (Morimoto-Tomita et al., 2002 *J Biol Chem* 277, 49175-85) with some modifications. Reaction conditions included 10 µM enzyme, 2 mM 4-MUS, 50 mM sodium acetate, pH 6.0, and 5 mM CaCl$_2$ in a 20 µL reaction volume. The enzyme incubation temperature was 30° C. Activity was measured as a function of time ranging from 3 to 24 hours; the reactions were quenched by the addition of 200 µL 0.5 M Na$_2$CO$_3$, pH 10.7. Detection of fluorescent methylumbelliferone was measured at this alkaline pH using a SpectraMax microtiter plate reader (Molecular Dynamics, Sunnyvale, Calif.) set at excitation and emission wavelengths of 360 and 440 nm, respectively. Fluorescence intensity was corrected against background (minus enzyme control). In both assays, 0.5 unit of arylsulfatase from *Aerobacter aerogenes* (Sigma, St. Louis, Mo.) was used as a positive control.

Pilot 6-O-Sulfatase and N-Sulfamidase Assays

Initial assessment of substrate specificity and pH optima was made using a capillary electrophoresis-based assay for the detection of desulfated products. Preliminary enzyme activity was measured against the following series of fluorescently derivatized, monosulfated gluco and galactopyranosides: 4-MU-GlcNAc,6S, 4-MU-GlcNS, 4-MU-GalNAc,6S and 4-MU-Gal6S. Standard reactions included 1 mM substrate, 1-10 µM enzyme, 50 mM sodium acetate, pH 5.5-6.5 and 5 mM CaCl$_2$ in a 20 µL reaction volume. For pilot experiments, exhaustive reactions involved overnight incubations at 30° C. Enzyme was inactivated by heat denaturation at 95° C. for 10 minutes, followed by a 10-fold dilution into water. Reaction products were resolved by capillary electrophoresis using a 25 cm long, 75 µm (i.d.) fused silica capillary (Agilent Technologies, Palo Alto, Calif.). Electrophoresis was carried out under negative polarity by applying a voltage of −15 kV (~1.2 W) for 10 minutes. Substrate desulfation was measured as a percentage of substrate depletion relative to a minus enzyme control as monitored by the loss of UV absorbance at 315 nm detected at approximately 4 minutes. A standard capillary electrophoresis buffer included 50 mM Tris and 10 µM dextran sulfate (average MW of 10,000 Da) adjusted to pH 2.0 with phosphoric acid. At this pH, saccharide migration occurred on the basis of charge without the influence of electro-osmotic flow.

The effect of pH was likewise measured by capillary electrophoresis using the following three sets of buffers with overlapping pH ranging from 4.5 to 8.0: 50 mM sodium citrate at 4.5, 5.0, and 5.5; 50 mM MES at 5.5, 6.0, 6.5 and 7.0; and 50 mM MOPS at 6.5, 7.0, 7.5, and 8.0. Reactions included 1 µM enzyme, 2 mM 4-MU-GlcNAc,6S (for 6-O-sulfatase) or 4-MU-GlcNS (for N-sulfamidase), 50 mM buffer and 5 mM CaCl$_2$ in a 20 µL reaction volume. Assay was initiated by the addition of 2 µl of a 10× enzyme stock to 18 µL of preheated reaction mixture. Reactions were carried out at 30° C. for either 30 minutes (N-sulfamidase assay) or 60 minutes (6-O-sulfatase assay) and quenched by heat and dilution as described above.

The ability of both enzymes to desulfate unsaturated heparin and chondroitin disaccharides was assessed essentially as described for capillary electrophoresis based compositional analyses of enzymatically generated glycosaminoglycan di- and tetra-saccharides (Venkataraman et al., 1999 *Science* 286, 537-542). For these studies, the following disaccharide substrates were tested: ΔUGlcNAc,6S; ΔU2SGlcNAc,6S; ΔUGlcNS; ΔUGlcNS,6S; ΔU2SGlcNS, 6S; and ΔUGalNac,6S. Reactions included 500 µM substrate, 10 µM enzyme, 50 mM sodium acetate, pH 6.5 and +/−2 mM CaCl$_2$ in a 20 µL reaction volume.

Coupled Enzyme Assay for the Determination of Biochemical Reaction Conditions and Steady-State Kinetics Indirect measurement of enzyme activity was also made using a fluorimetrically-based plate assay in which the prerequisite desulfation of the appropriate glucopyranoside 1→4 methlybelliferone substrate by either the 6-O-sulfatase or N-sulfamidase was coupled to the glucosidase-mediated hydrolysis of the stereo-specific 1→4 glycosidic linkage between the pyranose ring and the adjoining fluorophore. Release of the free fluorophore (4-MU) was monitored spectroscopically as described above for the arylsulfatase assay using 4-MU sulfate. The two sulfatase assays differed in the choice of substrate in accordance to their specificity as well as the glucosidase added during the second, rate-limiting step. For the 6-O-sulfatase, the hydrolysis of the substrate 4-MU-β-D-GlcNAc,6S at the 6-OH position was coupled to β-glucosidase purified from sweet almonds (MP Biomedicals, Solon, Ohio, Catalog No. 195197). Likewise, N-sulfamidase hydrolysis of 4-MU-α-D-GlcNS at the 2-amino position was coupled to α-glucosidase (MP Biomedicals, Catalog No. 153487). In both cases, the efficacy of the coupled assay was contingent on the intrinsically poor ability either glucosidase possesses for hydrolyzing the glycosidic bond when the adjoining glucosamine is modified by a sulfate. The presumption of the first (sulfatase) activity being the rate-limiting step was established experimentally. Reaction conditions were optimized to satisfy three related criteria: 1) linear readout of fluorescent signal which is directly proportional to sulfatase activity; 2) quantitative release of 4-MU by glucosidase activity under every biochemical condition examined and; 3) negligible fluorescent quenching of the free chromophore.

For the 6-O-sulfatase/β-glucosidase assay, the standard reaction conditions included 2 µM recombinant enzyme, 50 mM sodium acetate buffer, pH 5.5, and 5 mM CaCl$_2$ in a 20 µl reaction volume. 4-MU-GlcNAc,6S substrate concentration was varied from 0.1-2 mM. 2 µL of enzyme were added to each well of a microtiter plate (prechilled on ice), plate gently vortexed, and contents of each well spun down for 1 minute at 500×g, 4° C. The assay was initiated by transferring the 96 well plate to a heating block prequilibrated at 30° C. Sulfatase incubation (first enzyme) was carried out at 30° C. for 20 minutes, after which enzyme activity was inactivated by heat denaturation (95° C., 10 minutes). In the second enzyme (glucosidase) step, the microtiter plate was once again chilled on ice. 40 units of β-glucosidase was added to each well, the plate mixed by gentle vortexing, spun down at 500×g for 1 minute at 4° C. and transferred to a heating block prequilibrated at 37° C. Incubation proceeded for 60 minutes prior to being quenched with 200 µL 0.5 M Na$_2$CO$_3$, pH 10.7. Reactions were transferred to a black 96 well, flat-bottom FIA-plate and fluorescence measured as described above for the detection of free 4-MU. Fluorescent signal was adjusted to background (minus sulfatase control). For β-glucosidase, this background hydrolysis was somewhat dependent on initial 4-MU-GlcNAc,6S concentration, but typically was less than 10%. Molar conversion of product was extrapolated from a standard curve generated from varying concentrations of 4-MU from 0-300 µM.

Coupled N-sulfamidase assay was generally described for the 6-O-sulfatase, but with the following modifications: 4-MU-GlcNS as substrate, 50 mM sodium acetate at pH 6.0 (instead of 5.5) and 1 µM enzyme. For the second enzyme step, 5 units of α-glucosidase were added. Enzyme incubation was carried out for 22 hours at 37° C. The obvious difference in enzyme efficacies between α-glucosidase versus β-glucosidase is reflected in the substantially longer incubation times required for the α-glucosidase to quantitatively hydrolyze the glycosidic α1→4 linkage between the fluorophore and the desulfated glucosamine. All other reaction conditions were as described for the coupled 6-O-sulfatase/β-glucosidase assay.

Michaelis-Menten kinetics were extrapolated from $V_o$ vs. substrate concentration plots fit by non-linear regression to pseudo-first order kinetics. Data represent the average of three experiments. Substrate concentration was varied from 0.1 to 2 mM 4-MU-GlcNAc,6S (for 6-O-sulfatase kinetics) or 4-MU-GlcNS (for N-sulfamidase kinetics). Additional conditions included the presence of 0, 0.5 mM, or 5 mM CaCl$_2$ or 1 mM EDTA under otherwise standard conditions described.

Compositional Analyses of Sulfatase Treated Heparin

20 µg heparin were preincubated with 10 µM 6-O-sulfatase or N-sulfamidase for 8 hours at 30° C. in a 20 µL reaction which included 25 mM sodium acetate, pH 7.0 and 2 mM calcium acetate, pH 7.0. Following this preincubation, enzymes were inactivated by heat denaturation at 95° C. for 10 minutes and heparin exhaustively digested overnight at 37° C. by the addition of 2 µL of a concentrated enzyme cocktail containing heparinase I and III. Subsequent CE-based compositional analyses of heparinase-derived disaccharides were completed as described (Venkataraman et al., 1999 *Science* 286, 537-542).

Sequential Degradation of Heparin Oligosaccharide by Flavobacterial Exo-Enzymes

The purified pentasulfated tetrasaccharide $\Delta U_{2S}H_{NS,6S}$ $IH_{NS,6S}$ was provided by Dr. I. Capila (Momenta Pharmaceuticals, Cambridge, Mass.). Enzyme sequence was as follows: 2-O-sulfatase→Δ4,5 glycuronidase→6-O-sulfatase→N-sulfamidase. After each step, the enzyme was heat inactivated and 20 µL aliquots removed prior to the addition of the next enzyme in the sequence. Initial reaction conditions included 20 mM Tris, pH 7.2 and 60 nanomoles of tetrasaccharide in a 120 µL reaction volume. All enzyme reactions were carried out at 30° C. Enzyme specific conditions included the following: 1) 2-O-sulfatase, 1 µM enzyme, 6 hours; 2) Δ4,5 glycuronidase, 1 µM enzyme, 6 hours; 3) 6-O-sulfatase, 5 µM enzyme, 5 mM CaCl$_2$, 12-15 hours; 4) N-sulfamidase, same conditions as for 6-O-sulfatase. Molecular masses of enzyme products were determined by MALDI mass spectrometry using established methods (Rhomberg et al., 1998, *Proc Natl Acad Sci USA* 95, 12232-12237).

CE-LIF for the Detection of Sequentially Degraded Oligosaccharides

The APTS derivitization protocol was adapted from Chen et al. (Chen F. T. A., and Evangelista R. A. (1995) *Analytical Biochemistry* 230, 273-280). Briefly, 2 µl of 100 mM 9-aminopyrene-1,4,6-trisulfonate (APTS) in 25% acetic acid (v/v) were mixed with 10 µl of 1M sodium cyanoborohydride in tetrahydrofuran and 1 µmol of saccharide. The reaction mixture was incubated at 75° C. for 2 hr and was diluted 1:100 prior to CE analysis. CE-LIF was performed on a Beckman Coulter ProteomeLab PA 800 with 488 nm argon LIF module. Samples were loaded onto a N—CHO capillary (50 µm I.D.× 65 cm total length) using 0.5 psi of pressure at the anode for 20 sec. Electrophoretic separations were performed using a 20 kV potential in a 100 mM sodium borate, pH 10.2 buffer for 15 min at 25° C. Fluorescence emission spectra were collected using a 520 nm narrow band filter.

ESI-Mass Spectrometry of Sulfated Glucosamine Monosaccharides

Electrospray ionization mass spectrometry was performed in the negative ion mode using an Agilent 1100 Series VL LC/MSD Trap. For simplicity, the samples were prepared by adding MeOH directly to the enzymatic reaction mixtures without purification and were directly injected into the source of the mass spectrometer using a syringe pump at a rate of ~8 µl/min, The SPS function of the software (LC/MSD Trap Software 4.1 Build 143, MSD Trap Control Version 5.0 Build 65) was used to tune the instrument with the target mass set to the mass of the substrate, the sample stability set to 50% and the drive level set to 100%. Data were acquired over the scan range of 100-2200 m/z by accumulating 30,000 ions per scan. Capillary voltage was set to 3000 V. Nitrogen was used as the drying gas while helium was used as the nebulizing gas, with flow rates of 5 and 15 liters/min, respectively. In each case a minimum of ten spectra were averaged.

For the initial substrate specificity experiments on unlabeled monosaccharides, reactions were carried out with 2.5 mM substrate, 2.5 mM CaCl$_2$, excess enzyme and 37.5 mM Tris Buffer at pH 7.5 at 37° C. overnight. For the experiments determining the order of action of the enzymes, reactions were carried out with 100 µM substrate, 2 mM CaCl$_2$, 5 µM enzyme and various buffers at 37° C. overnight. Samples were diluted 1:10 in MeOH prior to analysis in the ESI, and the carrier solvent was H2O:MeOH (1:10, v/v). For the time course experiments showing desulfation of different unlabeled monosaccharides, reactions were carried out with 2.5 mM substrate, 5 mM CaCl$_2$, 1 µM enzyme and 50 mM acetate buffer at pH 5.5 for the 6-O-sulfatase and pH 6.0 for the N-sulfamidase at 37° C. Reactions were quenched by diluting the samples 1:4 in MeOH. The carrier solvent was H2O: MeOH (1:4, v/v). In these experiments, 4-MU-GlcNS was added prior to injection as an internal standard to monitor ionization efficiency and mass accuracy within the source and trap.

Results

Molecular Cloning and Recombinant Expression of *Flavobacterium* Heparinum Sulfatase Genes The two sulfatase genes were identified through the screening of a genomic library with hybridization probes directed toward the flavobacterial 2-O-sulfatase. Two overlapping phagemid clones identified during this process were expanded by chromosomal walking and restriction mapping. Sequence analyses of this genomic region revealed two sizeable open reading frames of 1647 and 1524 base pairs (described hereafter as ORF B and ORF C, respectively). The two gene sequences putatively encode proteins of 545 (FIG. 1) and 500 (FIG. 2) amino acids in length (starting at the initiating Met). Neither sequence possessed an obvious Shine-Dalgarno ribosomal binding site within 10 nucleotides of the initiating ATG codon. A closer examination of their individual sequences at the protein level noted several important features. Both flavobacterial ORFs possess a N-terminal hydrophobic signal peptide and corresponding cleavage site sequence predicted by the Von Heijne method for gram-negative bacteria (Nielsen, H., et al. (1997) *Protein Eng* 10, 1-6). Both genes encode basic protein sequences of comparable amino acid composition (by mol percent). Of the two proteins, the ORF B gene product possesses a slightly higher theoretical pI (8.6 vs. 8.0) relative to ORF C. Both gene products also possess a canonical sulfatase domain as described by the Protein Family (PFAM) identifier PF 000884.

Both putative sulfatase genes were robustly expressed in *E. coli* as soluble enzymes. To achieve satisfactory expression levels, however, the removal of the amino terminal signal sequences of both proteins was genetically engineered. Exclusion of this domain, however, had little deleterious effect on each enzyme's specific activity. At the same time, replacement of this $NH_2$-terminal peptide with a histidine (6×His) tag facilitated purification of the recombinant proteins in essentially a single chromatographic step (to greater than 80% purity). Subsequent thrombin cleavage of the histidine tag was carried out. These $\Delta NH_2$-terminal truncations (lacking both the native signal sequence and $NH_2$-6×His tag) were used in all subsequent biochemical characterizations of the two sulfatases. The apparent molecular weights of the two recombinant proteins based on SDS-PAGE were consistent with their theoretical molecular weights calculated from their respective amino acid compositions (ORF B, 61,572 Da; ORF C, 53,193 Da).

Biochemical Characterization of Recombinant HSGAG Sulfatases: Preliminary Determination of Monosaccharide Substrate Specificity As a first step in the biochemical characterization of these enzymes, the possibility of both these enzymes (as well as the previously characterized 2-O-sulfatase) functioning as generic arylsulfatases was examined. All three enzyme activities were tested against 4-catechol sulfate and 4-MU-sulfate, two different aromatic sulfate esters commonly used as substrates to make this assessment. Of the three enzymes, only the 2-O-sulfatase exhibited an appreciable level of hydrolytic activity relative to a known arylsulfatase from *Aerobacter aerogenes* which served as a positive control. At the same time, the ORF B sulfatase did partly hydrolyze the 4-MU sulfate at a discernible rate, which was at least 3-fold greater than that measured for the ORF C protein, which exhibited only negligible activity.

The fact that the ORF B and ORF C encoded enzymes are both poor arylsulfatases does not preclude them from acting on sulfated carbohydrates. In reality, many such sulfatases (including those which desulfate heparin/heparan sulfate) fail to be classified as so-called "arylsulfatases" on the basis of this rather non-specific biochemical screen. Based at least in part on the multiple sequence alignment, it was thought that two additional glycosaminoglycan sulfatases, namely the heparan N-acetylglucosamine-6-O-sulfatase and heparan N-sulfamidase, had indeed been cloned. To further test these enzymes and examine their ability to act on carbohydrates, such as heparin and heparan sulfate, a modified substrate whereby the sulfated hexosamine was linked 1→4 ($\alpha$ or $\beta$) to methylbelliferone (4-MU) was used. The presence of this chromophore allowed for the direct monitoring of desulfation of the monosaccharide by capillary electrophoresis. Four monosulfated substrates were tested, all of which were commercially available. These included the two "heparin" monosaccharides 4-MU-GlcNAc,6S and 4-MU-GlcNS in addition to the 6-O-sulfated galactose sugars 4-MU-Gal6S and 4-MU-GalNAc,6S (corresponding to the monsaccharide constituents of keratan sulfate and chondroitin/dermatan sulfate, respectively). In this analysis, the ORF B sulfatase was specific for the 6-O-sulfated glucosamine (FIG. 5A). The ORF C gene product could only hydrolyze the glucosamine sulfated at the 2-amino position. The recombinantly expressed ORF B gene product did not act upon either of the two 6-O-sulfated galactose sugars. The structural discrimination for the two enzymes observed for the fluorescently derivatized sugars was confirmed by mass spectrometry using non-derivatized monosaccharides possessing otherwise identical chemistries.

Figure 5B:
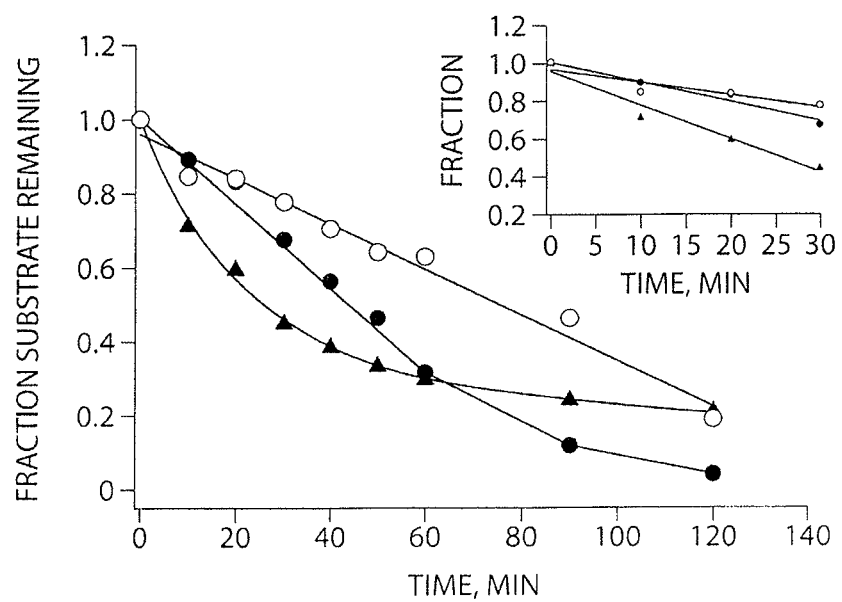
FIG. 5B shows results from the timecourse analyses of recombinant 6-O-sulfatase activity using three different, 6-O-sulfated monosaccharide substrates (each at 2.5 µM). GlcNAc,6S (●), GlcNS,6S (○), 4MUGlcNAc,6S (▲). Inset: time course out to 30 minutes.
Figure 6:
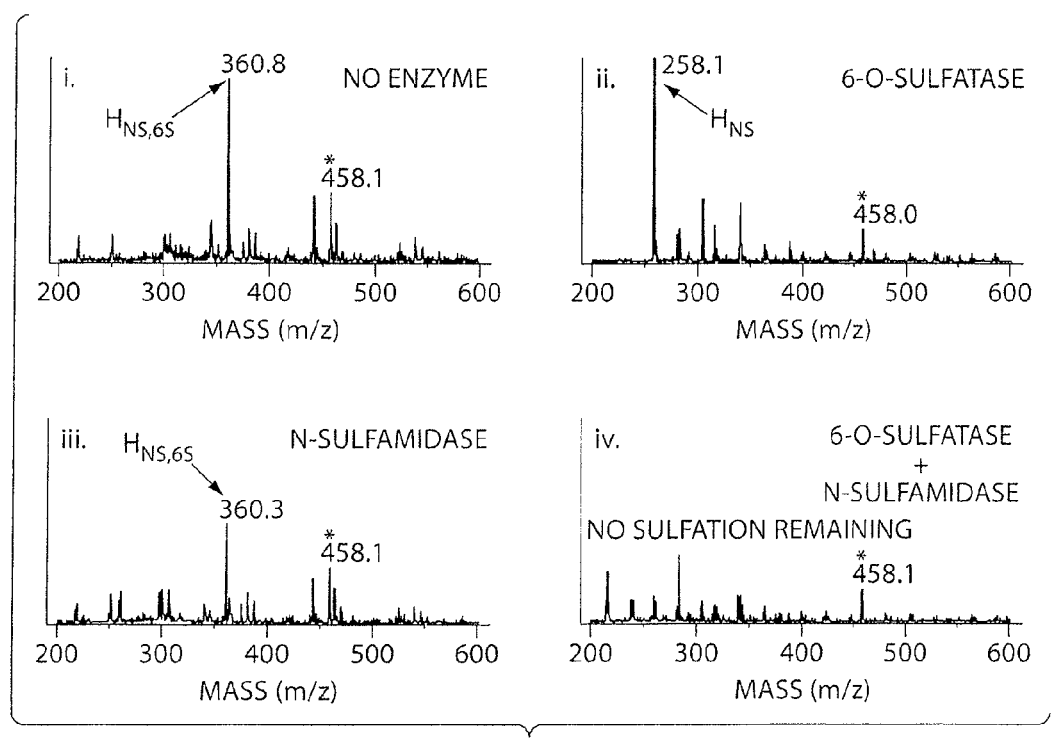
FIG. 6 illustrates the obligatory substrate-product relationship of the 6-O-sulfatase and N-sulfamidase. Desulfation of the disulfated monosaccharide $H_{NS,6S}$ by the two enzymes was followed by electrospray mass spectrometry (ESI-MS). Panel i): substrate only shown as the sodium adduct of a single ion species (M-1) with molecular mass of 360.8 Da; ii) desulfation of disulfated monosaccharide by 6-O-sulfatase, resulting in the monosulfated product (258.1 Da); iii) inability of N-sulfamidase to hydrolyze the original disulfated monosaccharide (compare with i); iv) co-treatment of the disulfated substrate with both enzymes showing the disappearance of all sulfated monosaccharides and demonstrating 6-O-desulfation by the 6-O-sulfatase prior to sulfate hydrolysis at the 2N position by the N-sulfamidase. Internal standard (458.1 Da) used in mass calibration is noted by an asterisk.

The substrate specificities of the two flavobacteria-derived sulfatases was further investigated by examining the influence of various substitutions at the 2-amino, 3-OH and 6-OH positions of the glucosamine. In these experiments, desulfation of non-derivatized monosaccharide substrates was detected and quantified by electrospray ionization (ESI) mass spectrometry. The 6-O-sulfatase required a substituted amine (acetate or sulfate) at the 2-amino position. A comparative kinetic analysis of the two corresponding substrates (GlcNAc,6S vs. GlcNS,6S) indicated only a modest preference of the enzyme for the monosulfated substrate (FIG. 5B). Reciprocally related to this observation (FIG. 6), it was found that the N-sulfamidase activity at the 2-amino position was absolutely abolished when a second sulfate at the 6-O-sulfate was also present. Both hydrolases were completely inhibited by the presence of a 3-O-sulfate.

Optimization of In Vitro Reaction Conditions

Having identified chromogenic substrates for each recombinant sulfatase, these substrates were also used to further develop a fluorescence-based plate assay as the means to define the optimal in vitro reaction conditions for each sulfatase. Parameters, such as ionic strength, and the effect of divalent metal ions as well as steady-state enzyme kinetics were investigated. A coupled enzyme assay in which the recombinant sulfatase served as the primary (product limiting) enzyme and either $\alpha$ or $\beta$-glucosidase as the secondary enzyme was chosen. Use of this second enzyme permitted the indirect detection of relative sulfatase activity by means of the stoichiometric release of free 4-MU which served as the fluorescent signal. This coupled assay for both enzymes was validated in control experiments demonstrating only modest hydrolysis of the 1→4-MU glycosidic linkage of the sulfated glucosamine (6-O or NS) by either glucosidase.

Figure 7A:
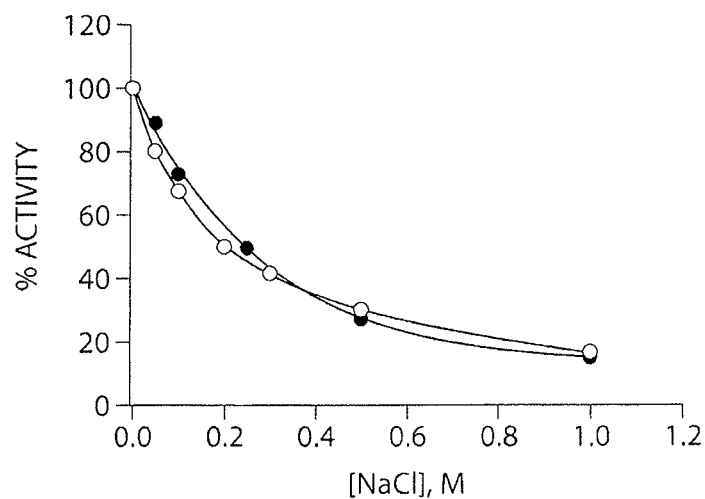
FIG. 7A demonstrates the inhibition by NaCl. Results are normalized to 0.0 M NaCl added (which is shown as 100%). 6-O-sulfatase (●); N-sulfamidase (○).
Figure 7B:
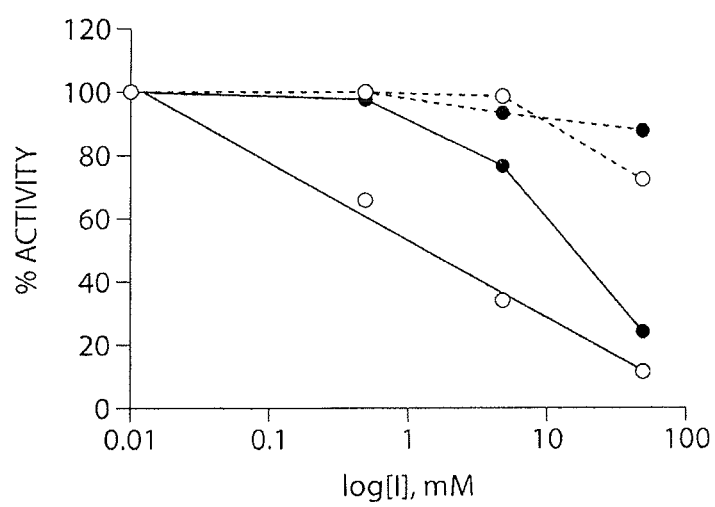
FIG. 7B demonstrates the inhibition by sulfate (●) or phosphate (○). Results for 6-O-sulfatase are represented by a solid line; results for N-sulfamidase are represented by a dashed line. Results are normalized to 0 sulfate or phosphate added. Log scale for inhibitor concentration, [I].
Figure 7C:
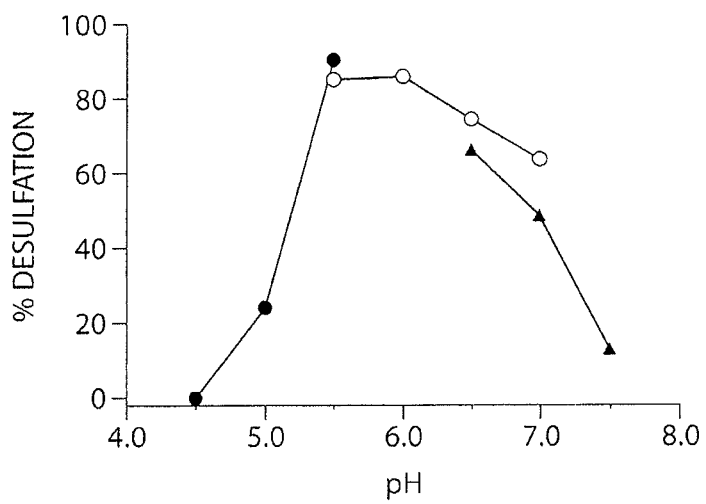
FIGS. 7C and 7D show the pH profile of sulfatase activity for 6-O-sulfatase and N-sulfamidase, respectively. Relative activities (% desulfation) were measured over a pH range of 4-8 using three buffers: sodium acetate (●), MES (○) and MOPS (▲).
Figure 7D:
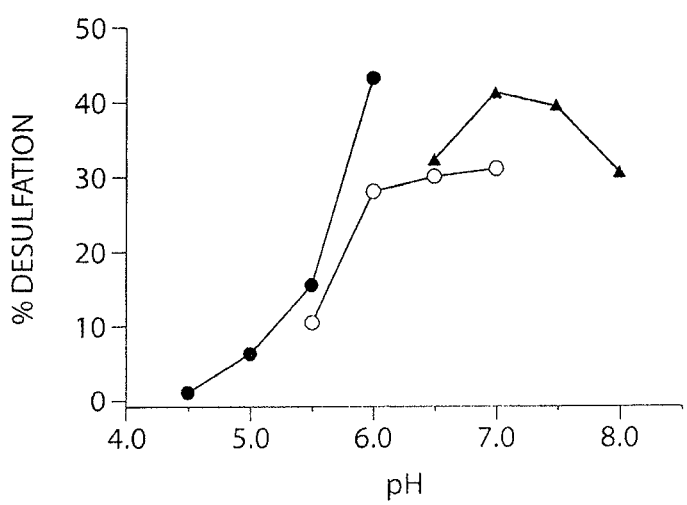

Both the 6-O-sulfatase and the N-sulfamidase were sensitive to increasing ionic strength as measured by the addition of NaCl (FIG. 7A). For both enzymes, 50% inhibition was observed at approximately 200 mM NaCl with less than 20% activity remaining at 1 M NaCl relative to the zero NaCl control. Both enzymes exhibited slightly acidic pH optima (between 5.5 and 6.5) (FIGS. 7B and D). Of the two enzymes, the N-sulfamidase was active over a broader range, especially above pH 7.0. Neither enzyme was active below pH 4.5. The enzymes showed higher activity in acetate buffer when compared to sulfonate buffers such as MES and MOPS when examined over this same pH range. However, only the 6-O-sulfatase was inhibited by the addition of sulfate or phosphate (FIG. 7B). Of the two anions, phosphate was clearly a more effective inhibitor, with 50% inhibition of 6-O-sulfatase activity observed at approximately 2 mM $PO_4^{2-}$ compared with approximately 20 mM $SO_4$.

Other members of this enzyme family share a relatively conserved active site and a common enzyme mechanism for sulfate hydrolysis (Parente et al., 1997 *Curr Opin Genet Dev* 7, 386-39; Bond et al., 1997 *Structure* 5, 277-289). Histidine, for example, is a candidate for participating in enzyme catalysis. At least two catalytic roles have been proposed for separate histidines based on crystallographic studies. The first role is stabilizing the Oγ2 oxygen of the hydrated formylglycine through hydrogen bonding, while also possibly acting as a proton acceptor. A second histidine stabilizes the sulfate itself, likewise through hydrogen bond contacts with one of the terminal oxygen atoms. Local sequence alignments between each of the flavobacterial sulfatases and the three structurally defined sulfatases (human arylsulfatase A (Lukatela et al., 1998) *Biochemistry* 37, 3654-3664; Waldow was largely manifested as a $k_{cat}$ effect (Table 1). For the N-sulfamidase, the effect of calcium was predictably more pronounced, with both kinetic parameters being affected in a generally proportional fashion. The catalytic role for calcium is supported by the consensus structure of the enzyme active site. In this snapshot, a divalent metal ion coordinates with at least one sulfate oxygen of the substrate while also coordinating with the carboxylates of four highly conserved acid residues surrounding the modified cysteine (FGly). Presumably, this coordination would promote catalysis by properly orienting the sulfate ester/amide bond for hydrolysis. Candidates are as predicted in FIG. 11 or as elsewhere described herein.

TABLE 1

Steady state kinetic parameters using 4-MU monosaccharide substrates

| | 6-O-sulfatase | | | N-sulfamidase | | |
|---|---|---|---|---|---|---|
| Addition | $k_{cat}$ (min$^{-1}$) | Km (μM) | $k_{cat}$/Km(×10$^2$) | $k_{cat}$ (min$^{-1}$) | Km (nM) | $k_{cat}$/Km (×10$^2$) |
| none | 2.5 | 146 | 1.7 | N.D.* | N.D.* | N.D.* |
| 0.5 mM Ca$^{+2}$ | 3.3 | 217 | 1.5 | 5.1 | 45 | 11.3 |
| 5 mM Ca$^{+2}$ | 6.8 | 327 | 2.1 | 21.9 | 178 | 12.3 |
| 1 mM EDTA | 2.5 | 264 | 0.95 | N.D.* | N.D.* | N.D.* |

*N.D. not determined due to lack of activity et al., 1999 *J Biol Chem* 274, 12284-12288) and B (Bond et al., 1997 *Structure* 5, 277-289) and the sulfatase from *P. aeruginosa* (Boltes et al., 2001 *Structure* (Camb) 9, 483-491) suggest histidine 130 for the 6-O-sulfatase as at least one of the homologous active site residues serving in this capacity.

In addition to histidine, other residues which line this consensus active site include at least three additional basic residues, which appear to form a binding pocket of positive ions. Two of these positively charged residues interact electrostatically with the negatively charged oxyanions of the sulfate; a third appears to interact with the hydrated formylglycine via a hydrogen bond. Potential homologous positions in the primary sequences of the two flavobacterially derived enzymes are, for example, depicted in FIG. 11 or as elsewhere described herein.

Role of Divalent Metal Ions in Enzyme Catalysis

Both sulfohydrolase activities were activated by the presence of calcium in a concentration-dependent manner albeit to clearly differing extents (FIG. 8). This divalent metal ion effect was especially pronounced for the N-sulfamidase which, in these experiments, required calcium for activity (FIG. 8B). In comparison, the 6-O-sulfatase, although activated 2-3 fold by the presence of calcium, was somewhat active even in the presence of 1 mM EDTA (FIG. 8A). Interestingly, the divalent metal activation for both enzymes was specific to calcium; inclusion of Mg$^{+2}$ or Mn$^{+2}$ had only negligible effects. To further examine this metal selectivity, the potential for enzyme inhibition in the presence of the calcium specific chelator, EGTA, was measured. EGTA was found to inhibit calcium-dependent N-sulfamidase activity (at 5 mM Ca$^{2+}$) in a concentration-dependent manner, with 50% inhibition occurring at approximately 3 mM EGTA. In contrast, EGTA had no appreciable effect on 6-O-sulfatase specific activity when measured under the same conditions.

Figure 8A:
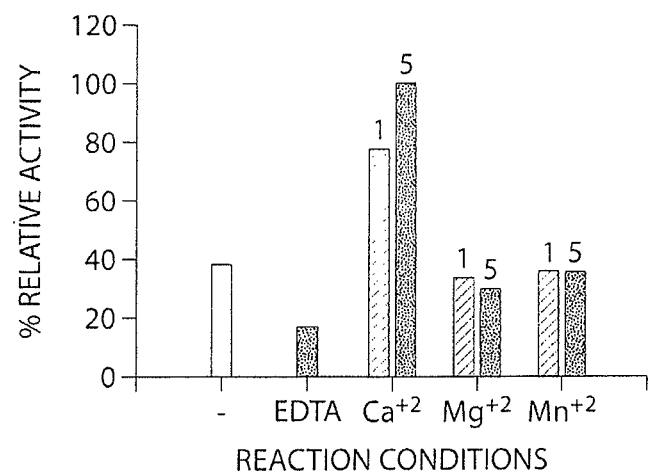
FIGS. 8A and 8B illustrates the calcium specific activation of 6-O-sulfatase activity and inhibition by EDTA (FIG. 8A). The calcium-specific requirement for N-sulfamidase activity and inhibition by EDTA is shown in FIG. 8B. In both cases, the divalent metal effect was not observed when calcium was replaced by either $Mg^{+2}$ or $Mn^{+2}$ (at either 1 mM or 5 mM concentrations). Open bars (no divalent metals added); black bars (1 mM EDTA added); light gray bars (1 mM divalent metal); stippled gray bars (5 mM divalent metal).
Figure 8B:
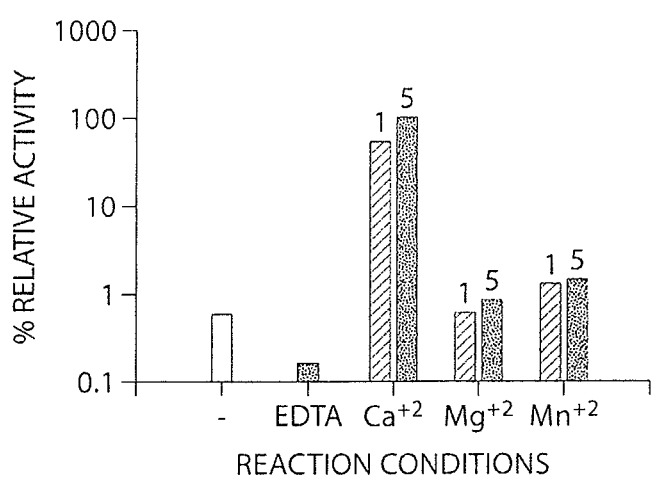
Figure 8C:
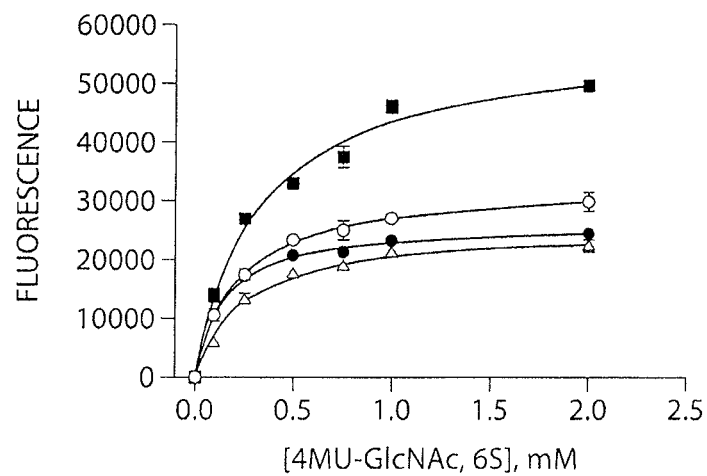
FIGS. 8C and 8D illustrate the effect of calcium on steady-state kinetics. Enzyme kinetics were measured for the 6-O-sulfatase (FIG. 8C) and N-sulfamidase (FIG. 8D) as described in Materials and Methods at varying concentrations of $Ca^{+2}$ or in the presence of 1 mM EDTA. Substrate saturation plots were fitted to pseudo first-order Michaelis-Menten kinetics by non-linear regression analyses. 0.5 mM Ca$^{+2}$ (●), 1 mM Ca$^{+2}$ (○), 5 mM Ca$^{+2}$ (■), 1 mM EDTA (Δ). The EDTA result (showing a lack of activity) is omitted in FIG. 8D.
Figure 8D:
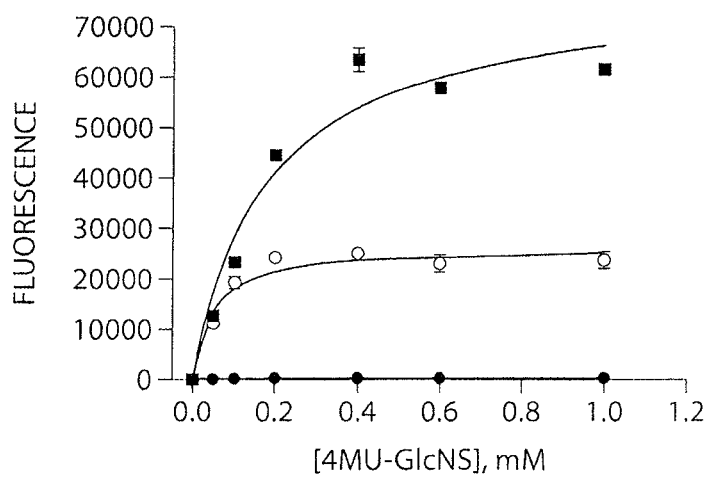
Figure 9A:
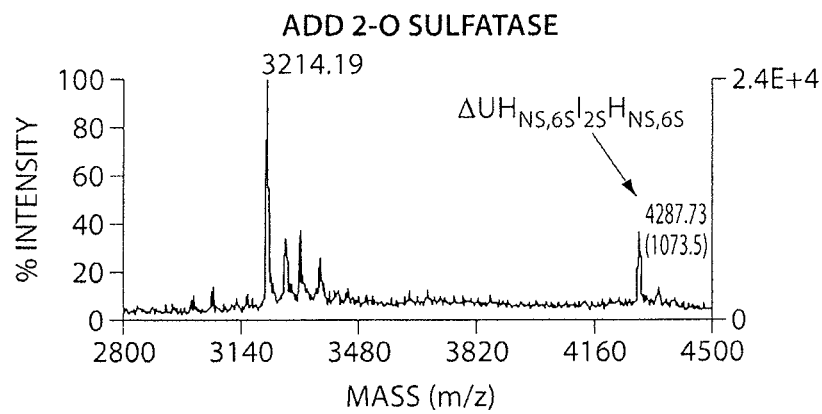
FIG. 9A provides results from the addition of the 2-O-sulfatase.
Figure 9B:
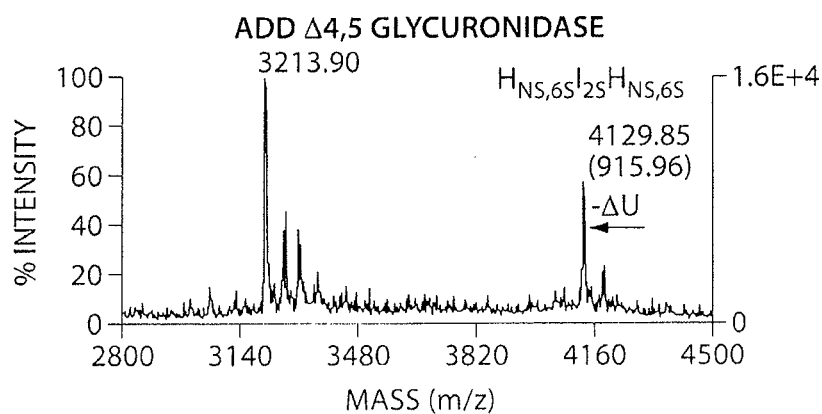
FIG. 9B provides results from the subsequent addition of the Δ4,5 glycuronidase.
Figure 9C:
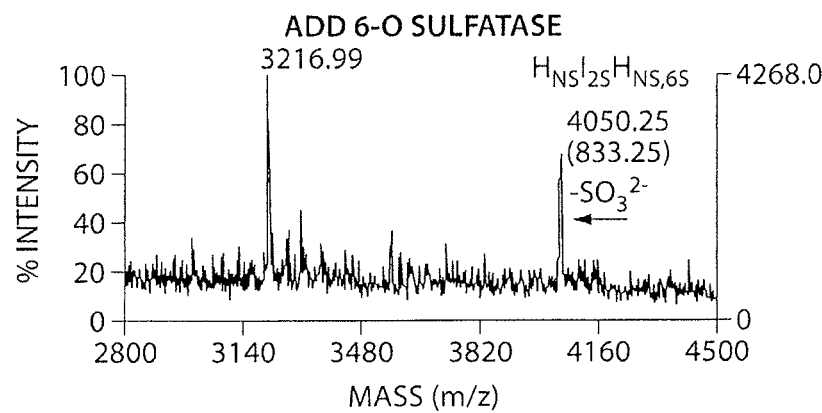
FIG. 9C provides results from the subsequent addition of the 6-O-sulfatase (note loss of a sulfate represented by a shift in net molecular mass from ~915 to ~835 Da)
Figure 9D:
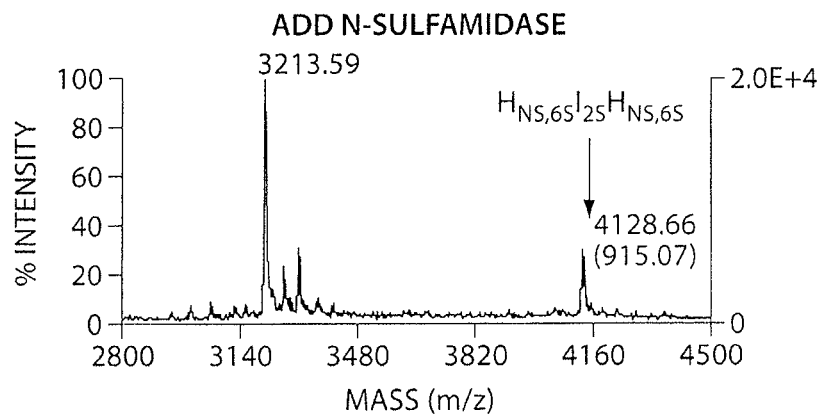
FIG. 9D provides results from the addition of N-sulfamidase directly after the Δ4,5 glycuronidase step (note the lack of any desulfation)
Figure 9E:
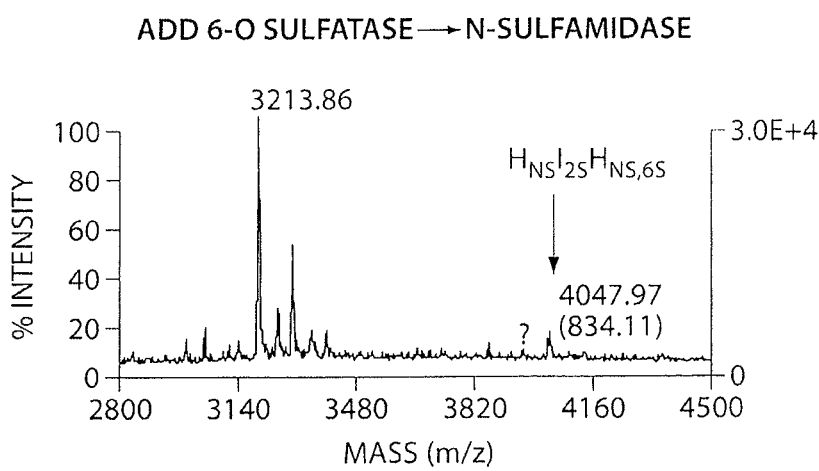
FIG. 9E provides results from the addition of the N-sulfamidase subsequent to the 6-O-sulfatase. The results in FIG. 9E are equivocal inasmuch as a double desulfated species with a net molecular mass of ~755 Da was not clearly detected in this experiment.

In an attempt to determine the mechanism by which calcium exerts its effect on the two HSGAG sulfatases, the effect of calcium on enzyme steady-state kinetics was measured (FIGS. 8C and 8D). Consistent with the previous results, the initial rates of both enzymes were affected by calcium in a concentration dependent fashion. For the 6-O-sulfatase, this Oligosaccharides Substrates The standard sulfatase assay described typically used singly sulfated, fluorogenic monosaccharides as substrates. The use of these enzymes to desulfate heparin/heparan sulfate oligosaccharides in accordance with their defined substrate specificities, however, was also explored. In nature, these HSGAG oligosaccharides could possess either an uronic acid (even number of saccharide units) or hexosamine (off number oligosaccharide) at their non-reducing ends. In the former case, the uronic acid would likely be unsaturated due to the preceding action of heparin lyases which cleave the GAG chain through a β-eliminative catalytic mechanism. To address this, both enzymes were initially tested against a panel of unsaturated heparin disaccharides. These included $\Delta U_{\pm 2S} H_{NAc,6S}$ and $\Delta U_{\pm 2S} H_{NS,6S}$ for the 6-O-sulfatase and $\Delta U_{\pm 2S} H_{NS+6S}$ for the N-sulfamidase. For these experiments, standard reaction conditions were chosen as defined in the monosaccharide studies. None of the unsaturated disaccharides were desulfated by either enzyme. The inability of these enzymes to do so was confirmed in a related experiment in which all possible heparin disaccharides were first generated by pre-treating heparin with heparinase I and III prior to adding the sulfatases to the same reaction tube. The converse experiment was also conducted in which unfractionated heparin was preincubated with either sulfatase for an extended period of time (8 hours) followed by the addition of heparinase I and III. In this sequence, sulfatase pretreatment had no effect on the compositional profile of the heparinase-derived cleavage products.

While the above-mentioned experiments categorize both the 6-O-sulfatase and the N-sulfamidase as exolytic enzymes, they do not rule out the possibility of these two sulfatases acting on the non-reducing end of saturated, odd-numbered oligosaccharides. This possibility was addressed using a combination of two structurally-related sulfated trisaccharides $H_{NS,6S} IH_{NS,6S}$ and $H_{NS,6S} I_{2S} H_{NS,6S}$. Each of these trisaccharides was generated from the corresponding tetrasaccharides $\Delta U_{2S} H_{NS,6S} I_{\pm 2S} H_{NS,6S}$ by the tandem use of the 2-O-sulfatase and the Δ4,5 glycuronidase prior to the addition of either the 6-O-sulfatase or N-sulfamidase. Desulfation was followed by MALDI-MS (FIG. 9). In this experiment, the 6-O-sulfatase was able to singularly desulfate both trisaccharides (FIG. 9C) The N-sulfamidase, however, was not able to do so (FIG. 9D), presumably because of the presence of the interfering 6-O-sulfate. The tandem use of the two enzymes (6-O-sufatase→N-sulfamidase) to doubly-desulfate either trisaccharide at the non-reducing end was also examined. The MALDI-MS results were equivocal, however, (FIG. 9E), and the possibility of such a species not sufficiently ionizing could not be ruled out.

Figure 10:
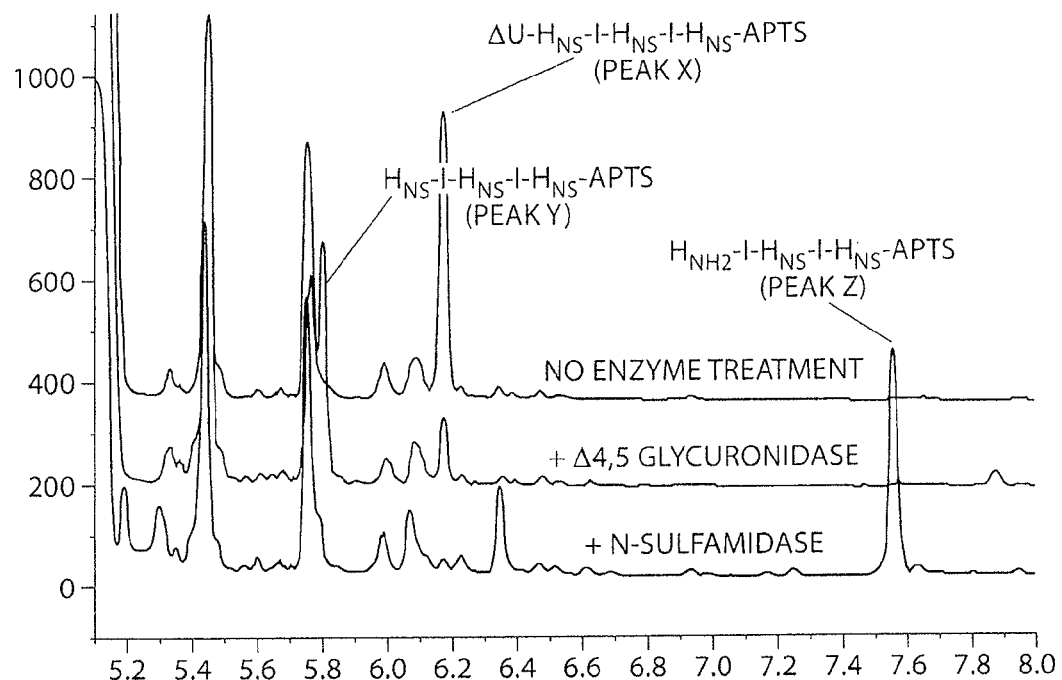
FIG. 10 demonstrates the sequential degradation of a HSGAG hexasaccharide. As in FIG. 9, the use of the flavobacterial exo-enzymes for sequentially degrading a HSGAG oligosaccharide is presented. In this experiment, the ability of the N-sulfamidase to desulfate the non-reducing end of an oligosaccharide is also demonstrated. The structurally-defined, heparin derived hexasaccharide $\Delta UH_{NS}IH_{NS}IH_{NS}$ was treated with Δ4,5 glycuronidase alone or with Δ4,5 glycuronidase followed by the N-sulfamidase. Resultant oligosaccharide products were fluorescently labeled at the reducing end with APTS by reductive amination as described in Materials and Methods. Oligosaccharides were resolved by capillary electrophoresis and detected by laser-induced fluorescence (CE-LIF). The N-desulfated pentasaccharide $H_{NH2}IH_{NS}IH_{NS}$ is observed as a unique peak appearing at approximately 7.6 minutes (peak Z).

The results presented for the exolytic desulfation of oligosaccharides at the non-reducing end are generally consistent with the substrate specificity data pertaining to desulfation of monosaccharide substrates. At the same time, the data could not rule out the possibility of the N-sulfamidase being absolutely refractory to oligosaccharides, perhaps as a result of the adjoining structure(s) at the reducing end. To resolve this, a modified approach was taken using both a different saccharide substrate ($H_{NS}IH_{NS}IH_{NS}$) as well as the means to detect the desulfated products. In this experiment, the trisulfated pentasaccharide was first generated by Δ4,5 glycuronidase treatment of the purified hexasaccharide $\Delta UH_{NS}IH_{NS}IH_{NS}$. Glycuronidase treatment was followed by incubation with the sulfamidase. All of the saccharides (untreated, Δ4,5 alone, Δ4,5 followed by N-sulfamidase) were fluorescently labeled at their reducing end through reductive amination. End labeling of the sugars permitted their detection by laser-induced fluorescence (LIF) following resolution of the products by capillary electrophoresis (FIG. 10). At each step in the experiment, saccharide peak assignment was inferred by observing discrete electrophoretic shifts in peak elution times as a function of exo-enzyme treatment. For example, conversion of the unsaturated hexasaccharide to a saturated pentasaccharide by glycuronidase-catalyzed uronic acid cleavage is consistent with the disappearance of peak X and the concomitant appearance of peak Y. Likewise, the N-desulfated pentasaccharide appears as a unique peak eluting at 7.6 minutes. From this analysis, it appears that the N-sulfamidase does desulfate some oligosaccharides in an exolytic fashion.

Discussion

Figure 4:
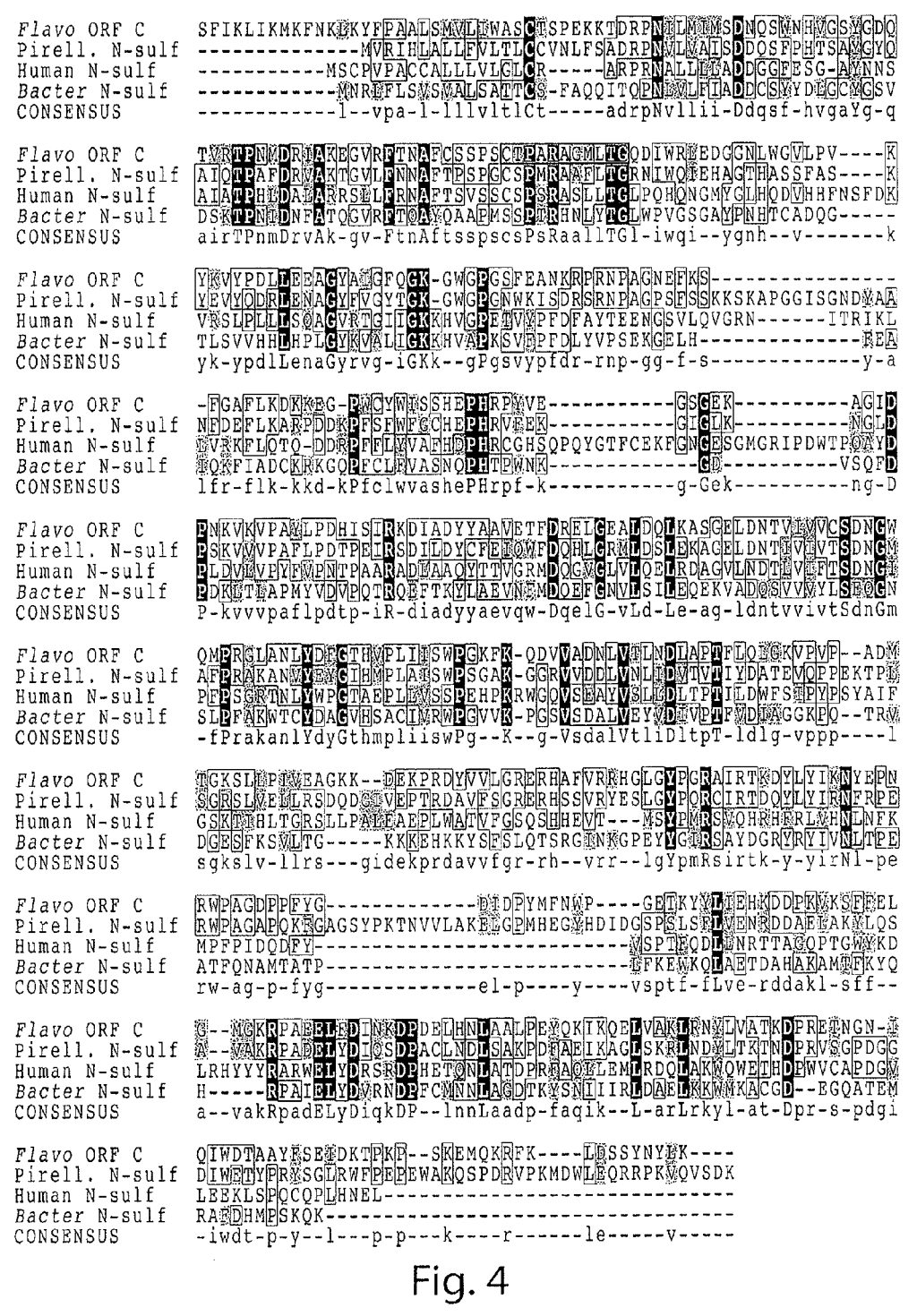

Two additional sulfatase genes from the *F. heparinum* genome have been cloned. A BLASTP sequence homology search of the two flavobacterial genes against the protein database unambiguously identified both gene products as members of a large sulfatase family. Both protein sequences possess the signature PFAM sulfatase motif C/SXPXRXXXXS/TG (SEQ ID NO: 5) as well as the highly conserved sequence LTG (at the +9 through +11 positions relative to this motif). As is the case for most (if not all) other sulfatases that comprise this large enzyme family, this sulfatase domain is located in the N-terminal region of the encoded polypeptide. The three flavobacterial sulfatases (2-O-sulfatase, ORF B and ORF C gene products) share only a limited overall homology to one another. While the latter two flavobacterial enzymes reported here are structurally distinct from each other at this level, they do exhibit some sequence similarity to other select (mostly bacterial) sulfatases, however. In particular, ORF B shows a strong sequence homology (greater than 50%) to the mucin-desulfating sulfatase encoded by the enteric bacterium *Prevotella* strain RS2 (MdsA gene) (FIG. 3). In addition to mucin, this particular enzyme is specific for free N-acetylglucosamine-6-O-sulfate (Roberton, A. M., et al. (2000) *Methods Mol Biol* 125, 417-26). The two respective genes code for proteins of comparable molecular weight; they also exhibit strong homology throughout their respective sequences (and not merely biased toward the N-terminal sulfatase domain). The only substantive difference in their primary structure essentially involves a 31 amino acid hydrophilic insertion present in the flavobacterial sulfatase which is lacking in the *Prevotella* enzyme. In a similar vein, ORF C shows considerable homology to several putative sulfohydrolases annotated in the *Pirelulla* sp. genome (Glockner, F. O., et al. (2003) *Proc Natl Acad Sci USA* 100, 8298-303). The best sequence alignment is with a predicted heparan N-sulfamidase with which the flavobacterial ORF C gene product shares approximately 40% compositional identity and nearly 60% conserved amino acid substitutions distributed throughout most of the protein (FIG. 4).

Both putative sulfatases possess a cysteine-specific active site. It is at this conserved cysteine (and not serine) that the critical co- or post-translational oxidation to an L-C-α formylglycine (FGly) presumably occurs (Dierks, T., et al. (1998) *FEBS Lett* 423, 61-5 and Dierks, T., et al. (2005) *Cell* 121, 541-52). A prediction in favor of this covalent modification taking place when these two enzymes are recombinantly expressed in *E. coli* would be consistent with the functional expression of other cys-based sulfatases in the same heterologous system (Dierks, T., et al. (1998) *J Biol Chem* 273, 25560-4). Results for 2-O-sulfatase identified FGly formation at a corresponding cysteine and demonstrated its function in enzyme catalysis.

Beyond the predicted function, the putative function was confirmed first by examining the ability of these enzymes to act as so-called "arylsulfatases", and second to act within the context of HSGAG degradation. To the first point, the results failed to unequivocally ascribe to either enzyme a "generic" sulfatase activity based exclusively on a commonly employed arylsulfatase assay. The fact that the ORF B and ORF C encoded enzymes are both poor arylsulfatases according to this assay; however, does not preclude them from acting on sulfated carbohydrates. In reality, many sulfatases (including those which desulfate heparin/heparan sulfate) fail to be classified as so-called "arylsulfatases" on the basis of this rather non-specific biochemical screen. At the same time, the results using more structurally directed monosaccharide substrates have unequivocally confirmed that two additional glycosaminoglycan sulfatases have been cloned. Moreover, the experiments go beyond this basic description and expound upon important structural determinants of enzyme specificity. In particular, the results presented identify the spatial orientation of the C4 hydroxyl as an additional structural determinant of substrate specificity, thus making the two flavobacterial sulfatases heparin/heparan sulfate degrading enzymes. The HSGAG specificity of this enzyme points to the likely existence of a unique flavobacterial gene (or set of genes) encoding the 6-O-desulfation of galactose/galactosamine.

The standard sulfatase assay described typically used singly sulfated, fluorogenic monosaccharides as substrates. In retrospect, these fluorogenic substrates were valuable in initially assigning enzyme function as well as defining the optimal in vitro reaction conditions by which to study their enzymology. At the same time, the potential use of these enzymes to desulfate heparin/heparan sulfate oligosaccharides in accordance with their defined substrate specificities was of interest. Central to this application is the question of the endolytic vs. exolytic potential of the two enzymes. By definition, the former mode of action would predict their ability to hydrolyze internally located sulfates within either a disaccharide or oligosaccharide chain. In the studies performed, neither enzyme was able to desulfate any of the unsaturated heparin/heparan disaccharides. Moreover, pre-treatment of unfractionated heparin with either enzyme failed to demonstrate loss of sulfates as assessed by compositional analysis following heparinase cleavage of the pre-treated polysaccharide.

On the other hand, an exolytic mode of action would require these enzymes to sequentially follow Δ4,5 glycuronidase hydrolysis of terminal uronic acids if, in fact, they are to act on the non-reducing end of these saccharides. The data presented here confirm this prediction, i.e., by demonstrating the ability of both enzymes to hydrolyze the non-reducing end of heparin-derived oligosaccharides. From the perspective of enzyme-substrate interactions, this reality places a structural constraint on the non-reducing end of the saccharide, namely a requirement of direct access to a sulfated hexosamine which is not hindered by the presence of an intervening uronate. It also imposes an apparent polarity to substrate binding within the enzyme active site. It is possible, however, that such a constraint is not absolutely imposed by the presence of the uronic acid per se (i.e., by virtue of being joined 1→4 to the sulfated hexosamine) but, more precisely, to the presence of the unsaturated bond at the C4 and C5 positions within this uronic acid. This chemical bond does impose a conformation of the sugar ring, which, in turn, restricts the relative orientation of the planar C5 carboxylate.

In addition, the $F.$ $heparinum$ HSGAG degradation pathway in vitro has been reconstructed through a biochemical description of the respective substrate specificities for each of the cloned enzymes. As such, the activity of these two enzymes has been placed in a sequential context related to the $F.$ $heparinum$ HSGAG degradation pathway as it presumably exists in vivo—i.e., a degradation pathway that begins with the heparin lyases (heparinases) and continues exolytically in the following order: 2-O-sulfatase→Δ4,5-glycuronidase→6-O-sulfatase→N-sulfamidase. Based on the results, it appears that both the 6-O-sulfatase and the N-sulfamidase also act downstream from 3-O-sulfatase activity.

Other questions related to the concerted activity of these enzymes in vivo also remain Chief among them is the question of what precise form the substrates for these end-of-the-line sulfatases actually take. Is may be reasonable to assume that the "natural" substrate for the 6-O-sulfatase and/or the N-sulfamidase are actually monosaccharides. This assumption is at least consistent with the sequentially exolytic nature of the flavobacterial HSGAG degrading pathway described. It is also in line with the HSGAG structure-activity relationships and the possibilities concerning active site architecture implied from these relationships. The ability of both these enzymes to desulfate fluorescently derivatized sugars in which the chromophore is linked 4→1 (α or β) to the adjoining hexosamine cannot be ignored. In addition, the ability of both these enzymes to act on longer oligosaccharides in a manner predicted by their substrate specificities is of practical value toward the use of these enzymes as discrete analytical tools for elucidating HSGAG fine structure.

In addition to describing the critical substrate specifity for each sulfohydrolase, important biochemical parameters related to their optimal use in vitro have been defined. These include pH and the role of divalent cations, namely calcium. In regard to pH, the slightly acidic pH optima demonstrated for both of these enzymes is consistent with observations for the pH optima of the 2-O-sulfatase (Myette, J. R., et al. (2003) $J$ $Biol$ $Chem$ 278, 12157-66) and Δ4,5 glycuronidase (Myette, J. R., et al. (2002) $Biochemistry$ 41, 7424-7434) enzymes. The flavobacterial HSGAG degrading enzymes are distinguished from their lysosomal counterparts, which, by virtue of their subcellular localization are most active at pH 4.5.

An investigation relating to enzyme catalysis has also been made with crystal structures of other members of this enzyme family, which share a relatively conserved active site and an enzyme mechanism for sulfate hydrolysis (Bond, C. S., et al. (1997) $Structure$ 5, 277-89 and Parenti, G., et al. (1997) Curr Opin Genet Dev 7, 386-91). Local sequence alignments between each of the flavobacterial sulfatases and the three structurally defined sulfatases (human arylsulfatase A (Lukatela, G., et al. (1998) $Biochemistry$ 37, 3654-64 and Waldow, A., et al. (1999) $J$ $Biol$ $Chem$ 274, 12284-8) and B (Bond, C. S., et al. (1997) $Structure$ 5, 277-89) and the sulfatase from $P.$ $aeriginosa$ (Boltes, I., et al. (2001) $Structure$ (Camb) 9, 483-91)) suggest histidine 130 for the 6-O-sulfatase as at least one of the homologous active site residues (FIG. 11).

In addition to histidine, other residues which line this consensus active site include at least three additional basic residues, which appear to form a binding pocket of positive ions. Two of these positively charged residues interact electrostatically with the negatively charged oxyanions of the sulfate; a third appears to interact with the hydrated formylglycine via a hydrogen bond. Potential homologous positions in the primary sequences of the two flavobacterially derived enzymes are shown in FIG. 11.

In addition, a catalytic role for calcium was supported by the kinetic data and consensus structure of the enzyme active site. In a snapshot of crystallographic studies, a divalent metal ion coordinates with at least one sulfate oxygen of the substrate while also coordinating with the carboxylates of four highly conserved acid residues surrounding the modified cysteine (FGly). Presumably, this coordination would promote catalysis by properly orienting the sulfate ester/amide bond for hydrolysis.

In reporting together the cloning of both sulfatase genes and an inclusive description of their enzymology, there is a risk of deemphasizing an obvious functional distinction. N-sulfated hexosamines are unique to heparin and heparan sulfate. It follows that the catalytic mechanism of sulfamide hydrolysis must also be somewhat unique from that of the sulfate ester. This distinction holds true, even when one considers the ubiquitous involvement of a formylglycine in enzyme catalysis. It is perhaps this unique chemistry that explains why the N-sulfamidase, unlike the 6-O-sulfatase, was largely uninhibited by sulfate or phosphate ions. It may also explain other empirical distinctions observed for the two enzymes, such as the involvement of calcium, the seeming inability to hydrolyze sulfated aromatic substrates (arylsulfates), or the inhibition by the presence of secondary sulfates within the glucosamine. As form follows function, this distinction naturally plays out at the level of enzyme structure. For the lysosomal N-sulfamidase, this distinction is evident even at the primary sequence level (where there is only about 10-25% identity to O-sulfatases). This limited sequence homology generally holds true when making the same comparison between the flavobacterial enzymes.

Even when one compares the heparan sulfamidase between divergent organisms such as $flavobacterium$ and mammals, discrete structural differences are likely given the reversed order within the degradation sequence in which the two enzymes act. In the lysosomal pathway, the N-sulfamidase is a relatively early enzyme that precedes the 6-O sulfatase, whereas our results indicate a reverse order for the flavobacterial enzymes. As such, the lysosomal heparin N-sulfamidase may naturally possess broader substrate specificity relative to the functional homologue from $F.$ $heparinum$. It follows that the relative active site topologies may also differ, especially as it pertains to additional residues for the lysosomal enzyme that must accommodate secondary sulfate interactions.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The listing of references herein is not intended to be an admission that any of the references is a prior art reference.

What is claimed is:

1. A method, comprising contacting a glycosaminoglycan with a glycosaminoglycan-degrading enzyme in an amount effective to cleave the glycosaminoglycan, thereby producing a cleavage product, wherein the glycosaminoglycan-degrading enzyme is an isolated sulfatase comprising the amino acid sequence of SEQ ID NO: 2 or 4.

2. The method of claim 1, wherein the isolated sulfatase comprises the amino acid sequence of SEQ ID NO:2.

3. The method of claim 1, wherein the isolated sulfatase comprises the amino acid sequence of SEQ ID NO:4.

4. The method of claim 1, wherein the glycosaminoglycan is further contacted with at least one additional glycosaminoglycan-degrading enzyme.

5. The method of claim 4, wherein the at least one additional glycosaminoglycan-degrading enzyme is used prior to, subsequent to, or concurrently with the sulfatase.

6. The method of claim 4, wherein the at least one additional glycosaminoglycan-degrading enzyme is heparinase I, heparinse II, heparinase III, 2-O sulfatase, or Δ4,5 glycuronidase.

7. The method of claim 4, wherein the at least one additional glycosaminoglycan-degrading enzyme is another sulfatase, glycosyl hydrolase, endoglucuronidase, or lyase.

8. The method of claim 6, wherein the at least one additional glycosaminoglycan-degrading enzyme is Δ4,5 glycuronidase.

9. The method of claim 8, wherein the Δ4,5 glycuronidase is contacted with the glycosaminoglycan prior to the sulfatase.

10. The method of claim 9, wherein the glycosaminoglycan is further contacted with a 2-O sulfatase and the contact with the 2-O sulfatase is prior to the contact with the Δ4,5 glycuronidase.

11. The method of claim 10, wherein the glycosaminoglycan is further contacted with a heparinase and the contact with the heparinase is prior to the contact with the 2-O sulfatase.

12. The method of claim 4, wherein the sulfatase comprises the amino acid sequence of SEQ ID NO:2; wherein the glycosaminoglycan is also contacted with N-sulfamidase, and wherein the glycosaminoglycan is contacted with the sulfatase prior to the N-sulfamidase.

13. The method of claim 11, wherein the sulfatase comprises the amino acid sequence of SEQ ID NO:2; wherein the glycosaminoglycan is also contacted with N-sulfamidase; and wherein the glycosaminoglycan is contacted with the sulfatase prior to the N-sulfamidase.

14. The method of claim 1, wherein the glycosaminoglycan is 3-O desulfated prior to contact with the sulfatase.

15. The method of claim 1, further comprising analyzing the cleavage product.

16. The method of claim 15, wherein the glycosaminoglycan is also contacted with at least one additional glycosaminoglycan-degrading enzyme.

17. The method of claim 16, wherein the at least one additional glycosaminoglycan-degrading enzyme is used prior to, subsequent to, or concurrently with the sulfatase.

18. The method of claim 16, wherein the at least one additional glycosaminoglycan-degrading enzyme is heparinase I, heparinse II, heparinase III, 2-O sulfatase, or Δ4,5 glycuronidase.

19. The method of claim 16, wherein the at least one additional glycosaminoglycan-degrading enzyme is another sulfatase, glycosyl hydrolase, endoglucuronidase, or lyase.

20. The method of claim 18, wherein the at least one additional glycosaminoglycan-degrading enzyme is Δ4,5 glycuronidase.

21. The method of claim 20, wherein the Δ4,5 glycuronidase is contacted with the glycosaminoglycan prior to the sulfatase.

22. The method of claim 21, wherein the glycosaminoglycan is further contacted with a 2-O sulfatase and the contact with the 2-O sulfatase is prior to the contact with the Δ4,5 glycuronidase.

23. The method of claim 22, wherein the glycosaminoglycan is further contacted with a heparinase and the contact with the heparinase is prior to the contact with the 2-O sulfatase.

24. The method of claim 16, wherein the sulfatase comprises the amino acid sequence of SEQ ID NO:2; wherein the glycosaminoglycan is also contacted with an N-sulfamidase; and wherein the glycosaminoglycan is contacted with the sulfatase prior to the N-sulfamidase.

25. The method of claim 23, wherein the sulfatase comprises the amino acid sequence of SEQ ID NO:2; wherein the glycosaminoglycan is also contacted with an N-sulfamidase; and wherein the glycosaminoglycan is contacted with the sulfatase prior to the N-sulfamidase.

26. The method of claim 15, wherein the glycosaminoglycan is 3-O desulfated prior to contact with the sulfatase.

27. The method of claim 15, wherein the presence of a particular glycosaminoglycan in a sample is determined based on the result from the analyzing step.

28. The method of claim 15, wherein the purity of a glycosaminoglycan in a sample is determined based on the result from the analyzing step.

29. The method of claim 15, wherein the composition of a glycosaminoglycan in a sample is determined based on the result from the analyzing step.

30. The method of claim 15, wherein the sequence of saccharide units in a glycosaminoglycan is determined based on the result from the analyzing step.

31. The method of claim 15, wherein the analyzing step is performed by subjecting the cleavage product to mass spectrometry, NMR spectroscopy, gel electrophoresis, capillary electrophoresis, or HPLC.

* * * * *

SEQUENCE LISTING

<160> NUMBER OF SEQ ID NOS: 27

<210> SEQ ID NO 1
<211> LENGTH: 1647
<212> TYPE: DNA
<213> ORGANISM: Flavobacterium heparinum

<400> SEQUENCE: 1

```
atactaaaaa tgggtaaatt gaaattaatt ttaccggttt tgtttgccgg tgccaccta      60 atgtcttgcc agcagcctaa acctgctgaa agtgccaaaa ggcccaatat tgtgttcatc     120
atgacagatg accataccat tcaggccata agcgcttatg gcagcaaatt ggtaaaaacg     180
cccaacctgg acagaattgc caacgagggt atgttgttta caactgttt tgtaaccaat     240 gcagtttgcg ggccatccag ggctactatc ctgaccggaa aatatagcca cctgaatggt     300
ttaacagaca attcaaaggt atttgacagt actcaggtta tttatccgca gttgttaaag     360
aaagcagggt accagaccgc aatgattggc aagtggcacc tgggctcaac accaatgggc     420
tttgactatt acagtatttt gcccaaccag ggacaatatt atcagcctga atttatagaa     480
aacgggcatc tggttaaaga aaaggatat gtaacgacc tcatcaccga taaggccatc      540
ggcttccttg aaaaaaggga ccatgataaa cccttctga tgatttacca gcacaaagca     600
ccgcaccgca actggttgcc ggcaccaaga cacctgggga tgtttgacga tacggttttt     660
cctgaacctg ccaatttact ggatgatttt aagggcaggg gcagggcagc aaaggagcag     720
ctgatgaaca tttctaccga tatgtggcct gcatgggacc ttaaaatgct ttctacagcc     780
cagcttgatt ctatggcgaa actacctgtt tcccctaagt ttaaagatgc caagggtgat     840
gattatcaac aggccaatga tccttcactg gataaagccc gttttttga agtgtacaac     900 cgcatgacag atgctgaaaa ggtacaatgg agaaaagtat atgacaaacg cgtagccgaa     960
tttaaaaggc tgaacccgaa aggggccgac ctggtgcgat ggaaatacca gcagtatatg    1020
cgcgattatc tggcctgcgt ggtttcggta gatgaaaatg taggcaggct gatggattac    1080
ctgaaaaaga taggggagct ggacaatacc attattgtct atacttccga tcagggcttt    1140
tatttgggtg agcatgggta tttcgacaaa cgtttttatgt acgatgaatc tttccgtaca    1200
cctttaatgg tgaggtatcc gccttcggtt aaagccggtt cagtaagtaa tgcctttgcc    1260
atgaacctcg attttgcacc aactttactg gattatgcag gggtaaaat accagccgat    1320 atgcagggcc tgtcgttacg tccggtattg gataacgcag gaaaatcgcc ggaaaactgg    1380
cgcaaggctg tatattatca ttattatgaa tttccaagct ggcacatggt taaaaggcac    1440
tatggcatca gaacggagcg ctataaactg atccattttt acaatgacat tgatgaatgg    1500
gaattatacg atatgcagaa agatccgcat gagatgcaaa acctgtataa cgataaggcc    1560
tatgagccga ttattaaaga cctgaaagtg caaatgaaaa agctgcaggt acaatataaa    1620
gatacgaatc caactgaagc tttataa                                         1647
```

<210> SEQ ID NO 2
<211> LENGTH: 530

<212> TYPE: PRT
<213> ORGANISM: Flavobacterium heparinum

<400> SEQUENCE: 2

```
Thr Leu Met Ser Cys Gln Gln Pro Lys Pro Ala Glu Ser Ala Lys Arg
1               5                   10                  15

Pro Asn Ile Val Phe Ile Met Thr Asp Asp His Thr Ile Gln Ala Ile
            20                  25                  30

Ser Ala Tyr Gly Ser Lys Leu Val Lys Thr Pro Asn Leu Asp Arg Ile
        35                  40                  45

Ala Asn Glu Gly Met Leu Phe Asn Asn Cys Phe Val Thr Asn Ala Val
    50                  55                  60

Cys Gly Pro Ser Arg Ala Thr Ile Leu Thr Gly Lys Tyr Ser His Leu
65                  70                  75                  80

Asn Gly Leu Thr Asp Asn Ser Lys Val Phe Asp Ser Thr Gln Val Ile
                85                  90                  95

Tyr Pro Gln Leu Leu Lys Lys Ala Gly Tyr Gln Thr Ala Met Ile Gly
            100                 105                 110

Lys Trp His Leu Gly Ser Thr Pro Met Gly Phe Asp Tyr Tyr Ser Ile
        115                 120                 125

Leu Pro Asn Gln Gly Gln Tyr Tyr Gln Pro Glu Phe Ile Glu Asn Gly
130                 135                 140

His Leu Val Lys Glu Lys Gly Tyr Val Thr Asp Leu Ile Thr Asp Lys
145                 150                 155                 160

Ala Ile Gly Phe Leu Glu Lys Arg Asp His Asp Lys Pro Phe Leu Met
                165                 170                 175

Ile Tyr Gln His Lys Ala Pro His Arg Asn Trp Leu Pro Ala Pro Arg
            180                 185                 190

His Leu Gly Met Phe Asp Asp Thr Val Phe Pro Glu Pro Ala Asn Leu
        195                 200                 205

Leu Asp Asp Phe Lys Gly Arg Gly Arg Ala Ala Lys Glu Gln Leu Met
210                 215                 220

Asn Ile Ser Thr Asp Met Trp Pro Ala Trp Asp Leu Lys Met Leu Ser
225                 230                 235                 240

Thr Ala Gln Leu Asp Ser Met Ala Lys Leu Pro Val Ser Pro Lys Phe
                245                 250                 255

Lys Asp Ala Lys Gly Asp Asp Tyr Gln Gln Ala Asn Asp Pro Ser Leu
            260                 265                 270

Asp Lys Ala Arg Phe Phe Glu Val Tyr Asn Arg Met Thr Asp Ala Glu
        275                 280                 285

Lys Val Gln Trp Arg Lys Val Tyr Asp Lys Arg Val Ala Glu Phe Lys
    290                 295                 300

Arg Leu Asn Pro Lys Gly Ala Asp Leu Val Arg Trp Lys Tyr Gln Gln
305                 310                 315                 320

Tyr Met Arg Asp Tyr Leu Ala Cys Val Val Ser Val Asp Glu Asn Val
                325                 330                 335

Gly Arg Leu Met Asp Tyr Leu Lys Lys Ile Gly Glu Leu Asp Asn Thr
            340                 345                 350

Ile Ile Val Tyr Thr Ser Asp Gln Gly Phe Tyr Leu Gly Glu His Gly
        355                 360                 365

Tyr Phe Asp Lys Arg Phe Met Tyr Asp Glu Ser Phe Arg Thr Pro Leu
370                 375                 380

Met Val Arg Tyr Pro Pro Ser Val Lys Ala Gly Ser Val Ser Asn Ala
385                 390                 395                 400
```

```
Phe Ala Met Asn Leu Asp Phe Ala Pro Thr Leu Leu Asp Tyr Ala Gly
            405                 410                 415

Val Lys Ile Pro Ala Asp Met Gln Gly Leu Ser Leu Arg Pro Val Leu
            420                 425                 430

Asp Asn Ala Gly Lys Ser Pro Glu Asn Trp Arg Lys Ala Val Tyr Tyr
            435                 440                 445

His Tyr Tyr Glu Phe Pro Ser Trp His Met Val Lys Arg His Tyr Gly
            450                 455                 460

Ile Arg Thr Glu Arg Tyr Lys Leu Ile His Phe Tyr Asn Asp Ile Asp
465                 470                 475                 480

Glu Trp Glu Leu Tyr Asp Met Gln Lys Asp Pro His Glu Met Gln Asn
            485                 490                 495

Leu Tyr Asn Asp Lys Ala Tyr Glu Pro Ile Ile Lys Asp Leu Lys Val
            500                 505                 510

Gln Met Lys Lys Leu Gln Val Gln Tyr Lys Asp Thr Asn Pro Thr Glu
            515                 520                 525

Ala Leu
    530

<210> SEQ ID NO 3
<211> LENGTH: 1524
<212> TYPE: DNA
<213> ORGANISM: Flavobacterium heparinum

<400> SEQUENCE: 3
agctttataa aattgataaa gatgaaattt aacaaattga atatttccc tgcagcactt      60 tcaatggtgc tgatatgggc ttcctgcact tcgccggaaa aaaaaacgga tcgtccgaat    120
atcctgatga tcatgtccga taaccaatcc tggaaccacg tagggagcta tggtgatcaa    180
acggtacgca cgcccaatat ggaccggatt gcgaagaag gggtacgttt taccaatgct     240
ttttgcagtt caccttcctg tacgcccgca agggctggaa tgctgaccgg acaggatata    300
tggaggttag aagatggggg caatttatgg ggtgttttac cggttaaata taagtatat     360 ccggatttgc tggaagaagc tggctatgcc ataggttttc agggaaaagg ctggggcccg    420
ggaagctttg aggccaataa acgcccaaga atcctgcag ggaatgagtt taaaagtttt     480
ggcgcatttt taaagataa aaaagaaggt ccctggtgtt attggatcag tagtcatgaa    540
cctcaccgtc cttatgtgga aggttccggc gaaaaagctg gtatcgatcc aaataaagta    600
aaagttcctg cctatttgcc agatcatatc agtataagaa aagacattgc agattactac    660
gctgcggttg aaaccttga tcgtgaactg ggcgaggccc ttgaccagtt gaaagcaagt    720
ggtgagctgg acaatacggt aattgtggta tgcagtgaca acggctggca atgccgcgt    780 ggactggcca acttgtacga ttttggtaca catgtgcccc tgatcatttc atggccaggt    840
aagtttaaac aggatgtagt tgccgataac ctggtcacac tgaatgacct tgccccaaca    900
ttcttacaac tgggtaaggt acctgtaccg gccgatatga cgggtaaaag tttattgccc    960
attgttgagg caggtaaaaa agatgaaaaa ccccggggatt atgtagtact gggaagagag   1020
cgtcatgcat tcgttcgtcg gcatggcctt ggctatcctg caggcaat tcgtactaaa     1080 gattatcttt acattaaaaa ttatgaacca atagatggc cggcaggtga tccgccgttt    1140
tatggagaca ttgatcccta catgttcaac tggccgggtg aaaccaaata ttacctgata    1200
gaacataaag atgatccgaa agtaaagtct ttctttgaac tgggaatggg caaacgtccg    1260
gcagaagaat tatttgatat caataaagat ccggatgaat tacacaatct ggcagcactt    1320
```

```
cctgaatatc aaaaaataaa acaggagctt gttgctaaat tgcgtaatta tttggtagca    1380
acgaaagatc cgagagaaac taatggtaat atacagatct gggatactgc tgcttatttt    1440
agtgaaatag ataaaacgcc aaaccaagt aaagagatgc aaaagcgttt taaattagat    1500
tccagttaca attatttgaa gtaa                                           1524

<210> SEQ ID NO 4
<211> LENGTH: 480
<212> TYPE: PRT
<213> ORGANISM: Flavobacterium heparinum

<400> SEQUENCE: 4

Ser Cys Thr Ser Pro Glu Lys Lys Thr Asp Arg Pro Asn Ile Leu Met
1               5                   10                  15

Ile Met Ser Asp Asn Gln Ser Trp Asn His Val Gly Ser Tyr Gly Asp
            20                  25                  30

Gln Thr Val Arg Thr Pro Asn Met Asp Arg Ile Ala Lys Glu Gly Val
        35                  40                  45

Arg Phe Thr Asn Ala Phe Cys Ser Ser Pro Ser Cys Thr Pro Ala Arg
50                  55                  60

Ala Gly Met Leu Thr Gly Gln Asp Ile Trp Arg Leu Glu Asp Gly Gly
65                  70                  75                  80

Asn Leu Trp Gly Val Leu Pro Val Lys Tyr Lys Val Tyr Pro Asp Leu
                85                  90                  95

Leu Glu Glu Ala Gly Tyr Ala Ile Gly Phe Gln Gly Lys Gly Trp Gly
            100                 105                 110

Pro Gly Ser Phe Glu Ala Asn Lys Arg Pro Arg Asn Pro Ala Gly Asn
        115                 120                 125

Glu Phe Lys Ser Phe Gly Ala Phe Leu Lys Asp Lys Glu Gly Pro
        130                 135                 140

Trp Cys Tyr Trp Ile Ser Ser His Glu Pro His Arg Pro Tyr Val Glu
145                 150                 155                 160

Gly Ser Gly Glu Lys Ala Gly Ile Asp Pro Asn Lys Val Lys Val Pro
                165                 170                 175

Ala Tyr Leu Pro Asp His Ile Ser Ile Arg Lys Asp Ile Ala Asp Tyr
            180                 185                 190

Tyr Ala Ala Val Glu Thr Phe Asp Arg Glu Leu Gly Glu Ala Leu Asp
        195                 200                 205

Gln Leu Lys Ala Ser Gly Glu Leu Asp Asn Thr Val Ile Val Val Cys
    210                 215                 220

Ser Asp Asn Gly Trp Gln Met Pro Arg Gly Leu Ala Asn Leu Tyr Asp
225                 230                 235                 240

Phe Gly Thr His Val Pro Leu Ile Ile Ser Trp Pro Gly Lys Phe Lys
                245                 250                 255

Gln Asp Val Val Ala Asp Asn Leu Val Thr Leu Asn Asp Leu Ala Pro
            260                 265                 270

Thr Phe Leu Gln Leu Gly Lys Val Pro Val Pro Ala Asp Met Thr Gly
        275                 280                 285

Lys Ser Leu Leu Pro Ile Val Glu Ala Gly Lys Lys Asp Glu Lys Pro
    290                 295                 300

Arg Asp Tyr Val Val Leu Gly Arg Glu Arg His Ala Phe Val Arg Arg
305                 310                 315                 320

His Gly Leu Gly Tyr Pro Gly Arg Ala Ile Arg Thr Lys Asp Tyr Leu
                325                 330                 335
```

-continued

```
Tyr Ile Lys Asn Tyr Glu Pro Asn Arg Trp Pro Ala Gly Asp Pro Pro
                340                 345                 350

Phe Tyr Gly Asp Ile Asp Pro Tyr Met Phe Asn Trp Pro Gly Glu Thr
            355                 360                 365

Lys Tyr Tyr Leu Ile Glu His Lys Asp Pro Lys Val Lys Ser Phe
    370                 375                 380

Phe Glu Leu Gly Met Gly Lys Arg Pro Ala Glu Glu Leu Phe Asp Ile
385                 390                 395                 400

Asn Lys Asp Pro Asp Glu Leu His Asn Leu Ala Ala Leu Pro Glu Tyr
                405                 410                 415

Gln Lys Ile Lys Gln Glu Leu Val Ala Lys Leu Arg Asn Tyr Leu Val
            420                 425                 430

Ala Thr Lys Asp Pro Arg Glu Thr Asn Gly Asn Ile Gln Ile Trp Asp
        435                 440                 445

Thr Ala Ala Tyr Phe Ser Glu Ile Asp Lys Thr Pro Lys Pro Ser Lys
    450                 455                 460

Glu Met Gln Lys Arg Phe Lys Leu Asp Ser Ser Tyr Asn Tyr Leu Lys
465                 470                 475                 480
```

<210> SEQ ID NO 5
<211> LENGTH: 11
<212> TYPE: PRT
<213> ORGANISM: Artificial Sequence
<220> FEATURE:
<223> OTHER INFORMATION: PFAM sulfatase consensus
<220> FEATURE:
<221> NAME/KEY: misc_feature
<222> LOCATION: (1)..(1)
<223> OTHER INFORMATION: Xaa can be either Cysteine or Serine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (10)
<223> OTHER INFORMATION: Xaa can be either Serine or Threonine

<400> SEQUENCE: 5

```
Xaa Xaa Pro Xaa Arg Xaa Xaa Xaa Xaa Xaa Gly
1               5                   10
```

<210> SEQ ID NO 6
<211> LENGTH: 527
<212> TYPE: PRT
<213> ORGANISM: Bacteroides

<400> SEQUENCE: 6

```
Met Lys Ser Asn Pro Ser Thr Leu Leu Pro Leu Ala Ala Leu Ser
1               5                   10                  15

Leu Ala Ser Cys Ala Asn Pro Gln Lys Glu Thr Lys Arg Pro Asn
            20                  25                  30

Ile Ile Phe Met Met Thr Asp Asp His Thr Thr Gln Ala Met Ser Cys
        35                  40                  45

Tyr Gly Gly Asn Leu Ile Gln Thr Pro Asn Met Asp Arg Ile Ala Asn
```

```
              50                  55                  60
Glu Gly Ile Arg Phe Asp Asn Cys Tyr Ala Val Asn Ala Leu Ser Gly
 65                  70                  75                  80

Pro Ser Arg Ala Cys Ile Leu Thr Gly Lys Phe Ser His Glu Asn Gly
                 85                  90                  95

Phe Thr Asp Asn Ala Ser Thr Phe Asn Gly Asp Gln Gln Thr Phe Pro
            100                 105                 110

Lys Leu Leu Gln Gln Ala Gly Tyr Gln Thr Ala Met Ile Gly Lys Trp
        115                 120                 125

His Leu Ile Ser Glu Pro Gln Gly Phe Asp His Trp Ser Ile Leu Ser
    130                 135                 140

Gly Gln His Glu Gln Gly Asp Tyr Tyr Asp Pro Asp Phe Trp Glu Asp
145                 150                 155                 160

Gly Lys His Ile Val Glu Lys Gly Tyr Ala Thr Asp Ile Ile Thr Asp
                165                 170                 175

Lys Ala Ile Asn Phe Leu Glu Asn Arg Asp Lys Asn Lys Pro Phe Cys
            180                 185                 190

Met Met Tyr His Gln Lys Ala Pro His Arg Asn Trp Met Pro Ala Pro
        195                 200                 205

Arg His Leu Gly Ile Phe Asn Asn Thr Ile Phe Pro Glu Pro Ala Asn
    210                 215                 220

Leu Phe Asp Asp Tyr Glu Gly Arg Gly Lys Ala Ala Arg Glu Gln Asp
225                 230                 235                 240

Met Ser Ile Glu His Thr Leu Thr Asn Asp Trp Asp Leu Lys Leu Leu
                245                 250                 255

Thr Arg Glu Glu Met Leu Lys Asp Thr Thr Asn Arg Leu Tyr Ser Val
            260                 265                 270

Tyr Lys Arg Met Pro Ser Glu Val Gln Asp Lys Trp Asp Ser Ala Tyr
        275                 280                 285

Ala Gln Arg Ile Ala Glu Tyr Arg Lys Gly Asp Leu Lys Gly Lys Ala
    290                 295                 300

Leu Ile Ser Trp Lys Tyr Gln Gln Tyr Met Arg Asp Tyr Leu Ala Thr
305                 310                 315                 320

Val Leu Ala Val Asp Glu Asn Ile Gly Arg Leu Leu Asn Tyr Leu Glu
                325                 330                 335

Lys Ile Gly Glu Leu Asp Asn Thr Ile Ile Val Tyr Thr Ser Asp Gln
            340                 345                 350

Gly Phe Phe Leu Gly Glu His Gly Trp Phe Asp Lys Arg Phe Met Tyr
        355                 360                 365

Glu Glu Cys Gln Arg Met Pro Leu Ile Ile Arg Tyr Pro Lys Ala Ile
    370                 375                 380

Lys Ala Gly Ser Thr Ser Ser Ala Ile Ser Met Asn Val Asp Phe Ala
385                 390                 395                 400

Pro Thr Phe Leu Asp Phe Ala Gly Val Glu Val Pro Ser Asp Ile Gln
                405                 410                 415

Gly Ala Ser Leu Lys Pro Val Leu Glu Asn Glu Gly Lys Thr Pro Ala
            420                 425                 430

Asp Trp Arg Lys Ala Ala Tyr Tyr His Tyr Tyr Glu Tyr Pro Ala Glu
        435                 440                 445

His Ser Val Lys Arg His Tyr Gly Ile Arg Thr Gln Asp Phe Lys Leu
    450                 455                 460

Ile His Phe Tyr Asn Asp Ile Asp Glu Trp Glu Met Tyr Asp Met Lys
465                 470                 475                 480
```

-continued

```
Ala Asp Pro Arg Glu Met Asn Asn Ile Phe Gly Lys Ala Glu Tyr Ala
            485                 490                 495

Lys Lys Gln Lys Glu Leu Met Gln Leu Leu Glu Thr Gln Lys Gln
        500                 505                 510

Tyr Lys Asp Asn Asp Pro Asp Glu Lys Glu Thr Val Leu Phe Lys
        515                 520                 525

<210> SEQ ID NO 7
<211> LENGTH: 517
<212> TYPE: PRT
<213> ORGANISM: Prevotella sp.

<400> SEQUENCE: 7

Met Lys Ser Asp Asn Met Arg Phe Tyr Ser Ala Met Leu Met Ala Gly
 1               5                  10                  15

Cys Gly Leu His Ala Ala Ala Gln Thr Gln Arg Pro Asn Ile Val Phe
                20                  25                  30

Ile Ile Thr Asp Asp His Ser Phe Gln Thr Ile Ser Ala Tyr Gly Ser
            35                  40                  45

Glu Val Ser Lys Leu Ala Pro Thr Pro Asn Ile Asp Arg Leu Ala Asn
        50                  55                  60

Glu Gly Ala Arg Phe Asp Asp Ala Phe Val Glu Asn Ser Leu Ser Thr
65                  70                  75                  80

Pro Ala Arg Ala Cys Leu Leu Thr Gly Leu Tyr Ser His Gln Asn Gly
                85                  90                  95

Gln Arg Thr Leu Gly Lys Gly Ile Asp Ser Thr Lys Thr Phe Val Ser
            100                 105                 110

Glu Leu Leu Gln Asp Ala Gly Tyr Gln Thr Gly Val Val Gly Lys Trp
        115                 120                 125

His Met Gln Cys Arg Pro Lys Gly Phe Asp Phe Phe Arg Ile Phe Glu
    130                 135                 140

Gly Gln Gly Asp Tyr Tyr Asn Pro Leu Val Leu Ser His Asp Ser Asn
145                 150                 155                 160

Gly Lys Tyr Glu Arg Glu Gln Gly Tyr Ala Thr Asp Ile Val Thr Glu
                165                 170                 175

His Ala Val Glu Phe Leu Asn Gln Arg Asp Glu Gln Lys Pro Phe Phe
            180                 185                 190

Leu Leu Val Glu His Lys Ala Pro His Arg Thr Trp Met Pro Asn Leu
        195                 200                 205

Lys Tyr Leu Gly Leu Tyr Asp Lys Val Glu Phe Pro Leu Pro Thr Thr
    210                 215                 220

Phe Trp Asp Asp Tyr Ala Thr Arg Gly Thr Cys Ala Ser Gln Gln Glu
225                 230                 235                 240

Met Thr Ile Ala Arg His Met Gln Leu Ala Tyr Asp Asn Lys Val Phe
                245                 250                 255

Glu Ile Asp Asn Ala Met Arg Thr Arg Met Leu Asp Arg Met Asp Arg
            260                 265                 270

Leu Gln Lys Gln Ala Trp Asp Ala Tyr Tyr Ser Pro Arg Asn Arg Ala
        275                 280                 285

Met Leu Asp Ala His Leu Thr Asp Ser Ala Leu Thr Val Trp Lys Tyr
    290                 295                 300

Gln Arg Tyr Met His Asp Tyr Leu Ser Thr Ile His Ser Val Asp Glu
305                 310                 315                 320

Ser Val Gly Glu Ile Tyr Glu Tyr Leu Lys Asn His Asn Leu Leu Asp
```

```
            325                 330                 335
Asn Thr Ile Leu Val Tyr Cys Ser Asp Gln Gly Phe Tyr Met Gly Glu
            340                 345                 350

His Gly Trp Phe Asp Lys Arg Phe Met Tyr Glu Glu Ser Leu Arg Thr
            355                 360                 365

Pro Leu Val Val Arg Tyr Pro Lys Ala Ile Lys Pro Gly Thr Val Asp
            370                 375                 380

Lys His Leu Val Gln Asn Ile Asp Phe Ala Pro Thr Leu Leu Asp Val
385                 390                 395                 400

Ala Gly Val Thr Lys Pro Glu Thr Met Ser Gly Arg Ser Phe Leu Asp
            405                 410                 415

Leu Phe Asp Gly Lys Gly Gln Asp Trp Arg Gln Ser Ile Tyr Tyr His
            420                 425                 430

Tyr Tyr Asp Tyr Pro Ala Glu His His Val Arg Arg His Asp Gly Val
            435                 440                 445

Arg Thr Asp Arg Tyr Lys Leu Ile His Phe Tyr Gly Ala Pro Met Glu
            450                 455                 460

Gly Asp His Asp Thr Val Asp Tyr Glu Glu Leu Tyr Asp Met Gln Asn
465                 470                 475                 480

Asp Pro Asn Glu Leu Asn Asn Leu Tyr Gly Lys Lys Gly Tyr Glu Lys
            485                 490                 495

Ile Thr Lys Glu Leu Lys Lys Ala Leu Lys Asp Tyr Arg Lys Asn Leu
            500                 505                 510

Lys Val Asp Glu Tyr
            515

<210> SEQ ID NO 8
<211> LENGTH: 522
<212> TYPE: PRT
<213> ORGANISM: Homo sapiens

<400> SEQUENCE: 8

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Met Asp Asp Met Gly Trp Gly Asp Leu Gly Val
            35                  40                  45

Tyr Gly Glu Pro Ser Arg Glu Thr Pro Asn Leu Asp Arg Met Ala Ala
        50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
            85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
            115                 120                 125

Lys Lys Ala Gly Tyr Val Ser Lys Ile Val Gly Lys Trp His Leu Gly
        130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
            165                 170                 175
```

```
Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Thr Ser Asp
        275                 280                 285

Asn Gly Ala Ala Leu Ile Ser Ala Pro Glu Gln Gly Gly Ser Asn Gly
            290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
        515                 520

<210> SEQ ID NO 9
<211> LENGTH: 543
<212> TYPE: PRT
<213> ORGANISM: Pirellula sp.

<400> SEQUENCE: 9

Met Val Arg Ile His Leu Ala Leu Leu Phe Val Leu Thr Leu Cys Cys
1               5                   10                  15

Val Asn Leu Phe Ser Ala Asp Arg Pro Asn Val Leu Val Ala Ile Ser
            20                  25                  30
```

Asp Asp Gln Ser Phe Pro His Thr Ser Ala Tyr Gly Tyr Gln Ala Ile
                35                  40                  45

Gln Thr Pro Ala Phe Asp Arg Val Ala Lys Thr Gly Val Leu Phe Asn
        50                  55                  60

Asn Ala Phe Thr Pro Ser Pro Gly Cys Ser Pro Met Arg Ala Ala Phe
65                  70                  75                  80

Leu Thr Gly Arg Asn Ile Trp Gln Ile Glu His Ala Gly Thr His Ala
                85                  90                  95

Ser Ser Phe Ala Ser Lys Tyr Glu Val Tyr Gln Asp Arg Leu Glu Asn
            100                 105                 110

Ala Gly Tyr Phe Val Gly Tyr Thr Gly Lys Gly Trp Gly Pro Gly Asn
            115                 120                 125

Trp Lys Ile Ser Asp Arg Ser Arg Asn Pro Ala Gly Pro Ser Phe Ser
    130                 135                 140

Ser Lys Lys Ser Lys Ala Pro Gly Gly Ile Ser Gly Asn Asp Tyr Ala
145                 150                 155                 160

Ala Asn Phe Asp Glu Phe Leu Lys Ala Arg Pro Asp Lys Pro Phe
            165                 170                 175

Ser Phe Trp Phe Gly Cys His Glu Pro His Arg Val Phe Glu Lys Gly
        180                 185                 190

Ile Gly Leu Lys Asn Gly Leu Asp Pro Ser Lys Val Val Pro Ala
        195                 200                 205

Phe Leu Pro Asp Thr Pro Glu Ile Arg Ser Asp Ile Leu Asp Tyr Cys
        210                 215                 220

Phe Glu Ile Gln Trp Phe Asp Gln His Leu Gly Arg Met Leu Asp Ser
225                 230                 235                 240

Leu Glu Lys Ala Gly Glu Leu Asp Asn Thr Ile Val Ile Val Thr Ser
                245                 250                 255

Asp Asn Gly Met Ala Phe Pro Arg Ala Lys Ala Asn Val Tyr Glu Tyr
            260                 265                 270

Gly Ile His Met Pro Leu Ala Ile Ser Trp Pro Ser Gly Ala Lys Gly
        275                 280                 285

Gly Arg Val Val Asp Asp Leu Val Asn Leu Ile Asp Val Thr Val Thr
    290                 295                 300

Ile Tyr Asp Ala Thr Glu Val Gln Pro Pro Glu Lys Thr Pro Leu Ser
305                 310                 315                 320

Gly Arg Ser Leu Val Glu Leu Leu Arg Ser Asp Gln Asp Gly Ile Val
            325                 330                 335

Glu Pro Thr Arg Asp Ala Val Phe Ser Gly Arg Glu Arg His Ser Ser
        340                 345                 350

Val Arg Tyr Glu Ser Leu Gly Tyr Pro Gln Arg Cys Ile Arg Thr Asp
    355                 360                 365

Gln Tyr Leu Tyr Ile Arg Asn Phe Arg Pro Glu Arg Trp Pro Ala Gly
    370                 375                 380

Ala Pro Gln Lys Phe Gly Ala Gly Ser Tyr Pro Lys Thr Asn Val Val
385                 390                 395                 400

Leu Ala Lys Glu Leu Gly Pro Met His Glu Gly Tyr His Asp Ile Asp
                405                 410                 415

Gly Ser Pro Ser Leu Ser Phe Leu Val Glu Asn Arg Asp Asp Ala Glu
            420                 425                 430

Leu Ala Lys Tyr Leu Gln Ser Ala Val Ala Lys Arg Pro Ala Asp Glu
            435                 440                 445

-continued

```
Leu Tyr Asp Ile Gln Ser Asp Pro Ala Cys Leu Asn Asp Leu Ser Ala
450                 455                 460

Lys Pro Asp Phe Ala Glu Ile Lys Ala Gly Leu Ser Lys Arg Leu Asn
465                 470                 475                 480

Asp Tyr Leu Thr Lys Thr Asn Asp Pro Arg Val Ser Gly Pro Asp Gly
                485                 490                 495

Gly Asp Ile Trp Glu Thr Tyr Pro Arg Tyr Ser Gly Leu Arg Trp Phe
        500                 505                 510

Pro Glu Pro Glu Trp Ala Lys Gln Ser Pro Asp Arg Val Pro Lys Met
    515                 520                 525

Asp Trp Leu Glu Gln Arg Pro Lys Val Gln Val Ser Asp Lys
530                 535                 540

<210> SEQ ID NO 10
<211> LENGTH: 502
<212> TYPE: PRT
<213> ORGANISM: Homo sapiens

<400> SEQUENCE: 10

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285
```

```
Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
                340                 345                 350

Glu Ala Glu Pro Leu Trp Ala Thr Val Phe Gly Ser Gln Ser His His
            355                 360                 365

Glu Val Thr Met Ser Tyr Pro Met Arg Ser Val Gln His Arg His Phe
        370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
                420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Lys Leu Ser Pro Gln Cys Gln
                485                 490                 495

Pro Leu His Asn Glu Leu
            500

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
gaattcatat gggtaaattg aaattaattt ta                              32

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
ggatcctcga gttataaagc ttcagttgga ttcgt                           35

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
tctagacata tgaaatttaa caaattgaaa tatttc                          36
```

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
ggatcctcga gttacttcaa ataattgtaa ctggaat                           37

<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
tctagacata tgtcttgcca gcagcctaaa c                                 31

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
tctagacata tgtcctgcac ttcgccggaa                                   30

<210> SEQ ID NO 17
<211> LENGTH: 545
<212> TYPE: PRT
<213> ORGANISM: Flavobacterium heparinum

<400> SEQUENCE: 17

Met Gly Lys Leu Lys Leu Ile Leu Pro Val Leu Phe Ala Gly Ala Thr
1               5                   10                  15

Leu Met Ser Cys Gln Gln Pro Lys Pro Ala Glu Ser Ala Lys Arg Pro
            20                  25                  30

Asn Ile Val Phe Ile Met Thr Asp Asp His Thr Ile Gln Ala Ile Ser
        35                  40                  45

Ala Tyr Gly Ser Lys Leu Val Lys Thr Pro Asn Leu Asp Arg Ile Ala
    50                  55                  60

Asn Glu Gly Met Leu Phe Asn Asn Cys Phe Val Thr Asn Ala Val Cys
65                  70                  75                  80

Gly Pro Ser Arg Ala Thr Ile Leu Thr Gly Lys Tyr Ser His Leu Asn
                85                  90                  95

Gly Leu Thr Asp Asn Ser Lys Val Phe Asp Ser Thr Gln Val Ile Tyr
            100                 105                 110

Pro Gln Leu Leu Lys Lys Ala Gly Tyr Gln Thr Ala Met Ile Gly Lys
        115                 120                 125

Trp His Leu Gly Ser Thr Pro Met Gly Phe Asp Tyr Tyr Ser Ile Leu
    130                 135                 140

Pro Asn Gln Gly Gln Tyr Tyr Gln Pro Glu Phe Ile Glu Asn Gly His
145                 150                 155                 160

Leu Val Lys Glu Lys Gly Tyr Val Thr Asp Leu Ile Thr Asp Lys Ala
                165                 170                 175

Ile Gly Phe Leu Glu Lys Arg Asp His Asp Lys Pro Phe Leu Met Ile
            180                 185                 190

Tyr Gln His Lys Ala Pro His Arg Asn Trp Leu Pro Ala Pro Arg His
          195                 200                 205

Leu Gly Met Phe Asp Asp Thr Val Phe Pro Glu Pro Ala Asn Leu Leu
    210                 215                 220

Asp Asp Phe Lys Gly Arg Gly Arg Ala Ala Lys Glu Gln Leu Met Asn
225                 230                 235                 240

Ile Ser Thr Asp Met Trp Pro Ala Trp Asp Leu Lys Met Leu Ser Thr
                245                 250                 255

Ala Gln Leu Asp Ser Met Ala Lys Leu Pro Val Ser Pro Lys Phe Lys
            260                 265                 270

Asp Ala Lys Gly Asp Asp Tyr Gln Gln Ala Asn Asp Pro Ser Leu Asp
        275                 280                 285

Lys Ala Arg Phe Phe Glu Val Tyr Asn Arg Met Thr Asp Ala Glu Lys
    290                 295                 300

Val Gln Trp Arg Lys Val Tyr Asp Lys Arg Val Ala Glu Phe Lys Arg
305                 310                 315                 320

Leu Asn Pro Lys Gly Ala Asp Leu Val Arg Trp Lys Tyr Gln Gln Tyr
                325                 330                 335

Met Arg Asp Tyr Leu Ala Cys Val Val Ser Val Asp Glu Asn Val Gly
            340                 345                 350

Arg Leu Met Asp Tyr Leu Lys Lys Ile Gly Glu Leu Asp Asn Thr Ile
        355                 360                 365

Ile Val Tyr Thr Ser Asp Gln Gly Phe Tyr Leu Gly Glu His Gly Tyr
    370                 375                 380

Phe Asp Lys Arg Phe Met Tyr Asp Glu Ser Phe Arg Thr Pro Leu Met
385                 390                 395                 400

Val Arg Tyr Pro Pro Ser Val Lys Ala Gly Ser Val Ser Asn Ala Phe
                405                 410                 415

Ala Met Asn Leu Asp Phe Ala Pro Thr Leu Leu Asp Tyr Ala Gly Val
            420                 425                 430

Lys Ile Pro Ala Asp Met Gln Gly Leu Ser Leu Arg Pro Val Leu Asp
        435                 440                 445

Asn Ala Gly Lys Ser Pro Glu Asn Trp Arg Lys Ala Val Tyr Tyr His
    450                 455                 460

Tyr Tyr Glu Phe Pro Ser Trp His Met Val Lys Arg His Tyr Gly Ile
465                 470                 475                 480

Arg Thr Glu Arg Tyr Lys Leu Ile His Phe Tyr Asn Asp Ile Asp Glu
                485                 490                 495

Trp Glu Leu Tyr Asp Met Gln Lys Asp Pro His Glu Met Gln Asn Leu
            500                 505                 510

Tyr Asn Asp Lys Ala Tyr Glu Pro Ile Ile Lys Asp Leu Lys Val Gln
        515                 520                 525

Met Lys Lys Leu Gln Val Gln Tyr Lys Asp Thr Asn Pro Thr Glu Ala
    530                 535                 540

Leu
545

<210> SEQ ID NO 18
<211> LENGTH: 500
<212> TYPE: PRT
<213> ORGANISM: Flavobacterium heparinum

<400> SEQUENCE: 18

Met Lys Phe Asn Lys Leu Lys Tyr Phe Pro Ala Ala Leu Ser Met Val

```
              1               5                  10                 15
Leu Ile Trp Ala Ser Cys Thr Ser Pro Glu Lys Lys Thr Asp Arg Pro
              20                 25                 30

Asn Ile Leu Met Ile Met Ser Asp Asn Gln Ser Trp Asn His Val Gly
              35                 40                 45

Ser Tyr Gly Asp Gln Thr Val Arg Thr Pro Asn Met Asp Arg Ile Ala
              50                 55                 60

Lys Glu Gly Val Arg Phe Thr Asn Ala Phe Cys Ser Ser Pro Ser Cys
 65                 70                 75                 80

Thr Pro Ala Arg Ala Gly Met Leu Thr Gly Gln Asp Ile Trp Arg Leu
                 85                 90                 95

Glu Asp Gly Gly Asn Leu Trp Gly Val Leu Pro Val Lys Tyr Lys Val
                100                105                110

Tyr Pro Asp Leu Leu Glu Glu Ala Gly Tyr Ala Ile Gly Phe Gln Gly
                115                120                125

Lys Gly Trp Gly Pro Gly Ser Phe Glu Ala Asn Lys Arg Pro Arg Asn
                130                135                140

Pro Ala Gly Asn Glu Phe Lys Ser Phe Gly Ala Phe Leu Lys Asp Lys
145                150                155                160

Lys Glu Gly Pro Trp Cys Tyr Trp Ile Ser Ser His Glu Pro His Arg
                165                170                175

Pro Tyr Val Glu Gly Ser Gly Glu Lys Ala Gly Ile Asp Pro Asn Lys
                180                185                190

Val Lys Val Pro Ala Tyr Leu Pro Asp His Ile Ser Ile Arg Lys Asp
                195                200                205

Ile Ala Asp Tyr Tyr Ala Ala Val Glu Thr Phe Asp Arg Glu Leu Gly
                210                215                220

Glu Ala Leu Asp Gln Leu Lys Ala Ser Gly Leu Asp Asn Thr Val
225                230                235                240

Ile Val Val Cys Ser Asp Asn Gly Trp Gln Met Pro Arg Gly Leu Ala
                245                250                255

Asn Leu Tyr Asp Phe Gly Thr His Val Pro Leu Ile Ile Ser Trp Pro
                260                265                270

Gly Lys Phe Lys Gln Asp Val Ala Asp Asn Leu Val Thr Leu Asn
                275                280                285

Asp Leu Ala Pro Thr Phe Leu Gln Leu Gly Lys Val Pro Val Pro Ala
290                295                300

Asp Met Thr Gly Lys Ser Leu Leu Pro Ile Val Glu Ala Gly Lys Lys
305                310                315                320

Asp Glu Lys Pro Arg Asp Tyr Val Val Leu Gly Arg Glu Arg His Ala
                325                330                335

Phe Val Arg Arg His Gly Leu Gly Tyr Pro Gly Arg Ala Ile Arg Thr
                340                345                350

Lys Asp Tyr Leu Tyr Ile Lys Asn Tyr Glu Pro Asn Arg Trp Pro Ala
                355                360                365

Gly Asp Pro Pro Phe Tyr Gly Asp Ile Asp Pro Tyr Met Phe Asn Trp
                370                375                380

Pro Gly Glu Thr Lys Tyr Tyr Leu Ile Glu His Lys Asp Pro Lys
385                390                395                400

Val Lys Ser Phe Phe Glu Leu Gly Met Gly Lys Arg Pro Ala Glu Glu
                405                410                415

Leu Phe Asp Ile Asn Lys Asp Pro Asp Glu Leu His Asn Leu Ala Ala
                420                425                430
```

Leu Pro Glu Tyr Gln Lys Ile Lys Gln Glu Leu Val Ala Lys Leu Arg
            435                 440                 445

Asn Tyr Leu Val Ala Thr Lys Asp Pro Arg Glu Thr Asn Gly Asn Ile
            450                 455                 460

Gln Ile Trp Asp Thr Ala Ala Tyr Phe Ser Glu Ile Asp Lys Thr Pro
465                 470                 475                 480

Lys Pro Ser Lys Glu Met Gln Lys Arg Phe Lys Leu Asp Ser Ser Tyr
            485                 490                 495

Asn Tyr Leu Lys
            500

<210> SEQ ID NO 19
<211> LENGTH: 548
<212> TYPE: PRT
<213> ORGANISM: Flavobacterium heparinum

<400> SEQUENCE: 19

Ile Leu Lys Met Gly Lys Leu Lys Leu Ile Leu Pro Val Leu Phe Ala
1               5                   10                  15

Gly Ala Thr Leu Met Ser Cys Gln Gln Pro Lys Pro Ala Glu Ser Ala
            20                  25                  30

Lys Arg Pro Asn Ile Val Phe Ile Met Thr Asp Asp His Thr Ile Gln
        35                  40                  45

Ala Ile Ser Ala Tyr Gly Ser Lys Leu Val Lys Thr Pro Asn Leu Asp
    50                  55                  60

Arg Ile Ala Asn Glu Gly Met Leu Phe Asn Asn Cys Phe Val Thr Asn
65                  70                  75                  80

Ala Val Cys Gly Pro Ser Arg Ala Thr Ile Leu Thr Gly Lys Tyr Ser
                85                  90                  95

His Leu Asn Gly Leu Thr Asp Asn Ser Lys Val Phe Asp Ser Thr Gln
            100                 105                 110

Val Ile Tyr Pro Gln Leu Leu Lys Lys Ala Gly Tyr Gln Thr Ala Met
        115                 120                 125

Ile Gly Lys Trp His Leu Gly Ser Thr Pro Met Gly Phe Asp Tyr Tyr
    130                 135                 140

Ser Ile Leu Pro Asn Gln Gly Gln Tyr Tyr Gln Pro Glu Phe Ile Glu
145                 150                 155                 160

Asn Gly His Leu Val Lys Glu Lys Gly Tyr Val Thr Asp Leu Ile Thr
                165                 170                 175

Asp Lys Ala Ile Gly Phe Leu Glu Lys Arg Asp His Asp Lys Pro Phe
            180                 185                 190

Leu Met Ile Tyr Gln His Lys Ala Pro His Arg Asn Trp Leu Pro Ala
        195                 200                 205

Pro Arg His Leu Gly Met Phe Asp Asp Thr Val Phe Pro Glu Pro Ala
    210                 215                 220

Asn Leu Leu Asp Asp Phe Lys Gly Arg Gly Arg Ala Ala Lys Glu Gln
225                 230                 235                 240

Leu Met Asn Ile Ser Thr Asp Met Trp Pro Ala Trp Asp Leu Lys Met
                245                 250                 255

Leu Ser Thr Ala Gln Leu Asp Ser Met Ala Lys Leu Pro Val Ser Pro
            260                 265                 270

Lys Phe Lys Asp Ala Lys Gly Asp Asp Tyr Gln Gln Ala Asn Asp Pro
        275                 280                 285

Ser Leu Asp Lys Ala Arg Phe Phe Glu Val Tyr Asn Arg Met Thr Asp

```
        290                 295                 300
Ala Glu Lys Val Gln Trp Arg Lys Val Tyr Asp Lys Arg Val Ala Glu
305                 310                 315                 320

Phe Lys Arg Leu Asn Pro Lys Gly Ala Asp Leu Val Arg Trp Lys Tyr
                325                 330                 335

Gln Gln Tyr Met Arg Asp Tyr Leu Ala Cys Val Val Ser Val Asp Glu
            340                 345                 350

Asn Val Gly Arg Leu Met Asp Tyr Leu Lys Lys Ile Gly Glu Leu Asp
        355                 360                 365

Asn Thr Ile Ile Val Tyr Thr Ser Asp Gln Gly Phe Tyr Leu Gly Glu
    370                 375                 380

His Gly Tyr Phe Asp Lys Arg Phe Met Tyr Asp Glu Ser Phe Arg Thr
385                 390                 395                 400

Pro Leu Met Val Arg Tyr Pro Pro Ser Val Lys Ala Gly Ser Val Ser
                405                 410                 415

Asn Ala Phe Ala Met Asn Leu Asp Phe Ala Pro Thr Leu Leu Asp Tyr
            420                 425                 430

Ala Gly Val Lys Ile Pro Ala Asp Met Gln Gly Leu Ser Leu Arg Pro
        435                 440                 445

Val Leu Asp Asn Ala Gly Lys Ser Pro Glu Asn Trp Arg Lys Ala Val
    450                 455                 460

Tyr Tyr His Tyr Glu Phe Pro Ser Trp His Met Val Lys Arg His
465                 470                 475                 480

Tyr Gly Ile Arg Thr Glu Arg Tyr Lys Leu Ile His Phe Tyr Asn Asp
                485                 490                 495

Ile Asp Glu Trp Glu Leu Tyr Asp Met Gln Lys Asp Pro His Glu Met
            500                 505                 510

Gln Asn Leu Tyr Asn Asp Lys Ala Tyr Glu Pro Ile Ile Lys Asp Leu
        515                 520                 525

Lys Val Gln Met Lys Lys Leu Gln Val Gln Tyr Lys Asp Thr Asn Pro
    530                 535                 540

Thr Glu Ala Leu
545

<210> SEQ ID NO 20
<211> LENGTH: 507
<212> TYPE: PRT
<213> ORGANISM: Flavobacterium heparinum

<400> SEQUENCE: 20

Ser Phe Ile Lys Leu Ile Lys Met Lys Phe Asn Lys Leu Lys Tyr Phe
1               5                   10                  15

Pro Ala Leu Ser Met Val Leu Ile Trp Ala Ser Cys Thr Ser Pro
                20                  25                  30

Glu Lys Lys Thr Asp Arg Pro Asn Ile Leu Met Ile Met Ser Asp Asn
            35                  40                  45

Gln Ser Trp Asn His Val Gly Ser Tyr Gly Asp Gln Thr Val Arg Thr
        50                  55                  60

Pro Asn Met Asp Arg Ile Ala Lys Glu Gly Val Arg Phe Thr Asn Ala
65                  70                  75                  80

Phe Cys Ser Ser Pro Ser Cys Thr Pro Ala Arg Ala Gly Met Leu Thr
                85                  90                  95

Gly Gln Asp Ile Trp Arg Leu Glu Asp Gly Gly Asn Leu Trp Gly Val
            100                 105                 110
```

```
Leu Pro Val Lys Tyr Lys Val Tyr Pro Asp Leu Leu Glu Glu Ala Gly
            115                 120                 125

Tyr Ala Ile Gly Phe Gln Gly Lys Gly Trp Gly Pro Gly Ser Phe Glu
130                 135                 140

Ala Asn Lys Arg Pro Arg Asn Pro Ala Gly Asn Glu Phe Lys Ser Phe
145                 150                 155                 160

Gly Ala Phe Leu Lys Asp Lys Lys Glu Gly Pro Trp Cys Tyr Trp Ile
                165                 170                 175

Ser Ser His Glu Pro His Arg Pro Tyr Val Glu Gly Ser Gly Glu Lys
            180                 185                 190

Ala Gly Ile Asp Pro Asn Lys Val Lys Val Pro Ala Tyr Leu Pro Asp
        195                 200                 205

His Ile Ser Ile Arg Lys Asp Ile Ala Asp Tyr Tyr Ala Ala Val Glu
    210                 215                 220

Thr Phe Asp Arg Glu Leu Gly Glu Ala Leu Asp Gln Leu Lys Ala Ser
225                 230                 235                 240

Gly Glu Leu Asp Asn Thr Val Ile Val Val Cys Ser Asp Asn Gly Trp
                245                 250                 255

Gln Met Pro Arg Gly Leu Ala Asn Leu Tyr Asp Phe Gly Thr His Val
            260                 265                 270

Pro Leu Ile Ile Ser Trp Pro Gly Lys Phe Lys Gln Asp Val Val Ala
        275                 280                 285

Asp Asn Leu Val Thr Leu Asn Asp Leu Ala Pro Thr Phe Leu Gln Leu
    290                 295                 300

Gly Lys Val Pro Val Pro Ala Asp Met Thr Gly Lys Ser Leu Leu Pro
305                 310                 315                 320

Ile Val Glu Ala Gly Lys Lys Asp Glu Lys Pro Arg Asp Tyr Val Val
                325                 330                 335

Leu Gly Arg Glu Arg His Ala Phe Val Arg Arg His Gly Leu Gly Tyr
            340                 345                 350

Pro Gly Arg Ala Ile Arg Thr Lys Asp Tyr Leu Tyr Ile Lys Asn Tyr
        355                 360                 365

Glu Pro Asn Arg Trp Pro Ala Gly Asp Pro Pro Phe Tyr Gly Asp Ile
    370                 375                 380

Asp Pro Tyr Met Phe Asn Trp Pro Gly Glu Thr Lys Tyr Tyr Leu Ile
385                 390                 395                 400

Glu His Lys Asp Asp Pro Lys Val Lys Ser Phe Phe Glu Leu Gly Met
                405                 410                 415

Gly Lys Arg Pro Ala Glu Glu Leu Phe Asp Ile Asn Lys Asp Pro Asp
            420                 425                 430

Glu Leu His Asn Leu Ala Ala Leu Pro Glu Tyr Gln Lys Ile Lys Gln
        435                 440                 445

Glu Leu Val Ala Lys Leu Arg Asn Tyr Leu Val Ala Thr Lys Asp Pro
    450                 455                 460

Arg Glu Thr Asn Gly Asn Ile Gln Ile Trp Asp Thr Ala Ala Tyr Phe
465                 470                 475                 480

Ser Glu Ile Asp Lys Thr Pro Lys Pro Ser Lys Glu Met Gln Lys Arg
                485                 490                 495

Phe Lys Leu Asp Ser Ser Tyr Asn Tyr Leu Lys
            500                 505

<210> SEQ ID NO 21
<211> LENGTH: 454
<212> TYPE: PRT
```

<213> ORGANISM: Artificial Sequence
<220> FEATURE:
<223> OTHER INFORMATION: Consensus Sequence

<400> SEQUENCE: 21

```
Met Lys Ser Leu Leu Leu Phe Ala Ala Leu Met Ser Cys Ala Gly Pro
1               5                   10                  15

Ala Ala Glu Thr Arg Pro Asn Ile Val Phe Ile Met Thr Asp Asp His
            20                  25                  30

Thr Phe Gln Ala Ile Ser Ala Tyr Gly Ser Lys Leu Ile Thr Pro Asn
        35                  40                  45

Leu Asp Arg Ile Ala Asn Glu Gly Ile Phe Asp Asn Cys Tyr Val Asn
    50                  55                  60

Ala Leu Gly Pro Ser Arg Ala Cys Ile Leu Thr Gly Lys Tyr Ser His
65                  70                  75                  80

Asn Gly Phe Thr Asn Ala Lys Gly Asp Ser Thr Gln Gln Ile Pro Glu
                85                  90                  95

Leu Leu Lys Ala Gly Tyr Gln Thr Ala Met Ile Gly Lys Trp His Leu
            100                 105                 110

Gly Ser Arg Pro Gln Gly Phe Asp Tyr Trp Ser Ile Asn Gln Gly Asp
        115                 120                 125

Tyr Tyr Gln Pro Phe Ile Glu Asp Asn Gly Lys Tyr Ile Lys Glu Lys
    130                 135                 140

Gly Tyr Ala Thr Asp Ile Ile Thr Asp Lys Ala Ile Glu Phe Leu Glu
145                 150                 155                 160

Arg Asp Lys Asn Lys Pro Phe Phe Met Met Tyr His Lys Ala Pro His
                165                 170                 175

Arg Asn Trp Met Pro Ala Pro Arg His Leu Gly Ile Phe Asp Lys Thr
            180                 185                 190

Ile Phe Pro Glu Pro Ala Asn Leu Asp Asp Tyr Gly Arg Gly Lys Ala
        195                 200                 205

Ala Arg Glu Gln Met Ser Ile Asp Leu Leu Ala Trp Asp Leu Lys Val
    210                 215                 220

Thr Thr Glu Met Leu Lys Asp Arg Tyr Val Tyr Arg Met Thr Glu Ala
225                 230                 235                 240

Trp Asp Ala Tyr Arg Ile Ala Glu Tyr Arg Gly Leu Lys Gly Ala Leu
                245                 250                 255

Ile Trp Lys Tyr Gln Gln Tyr Met Arg Asp Tyr Leu Ala Thr Val Leu
            260                 265                 270

Ser Val Asp Glu Asn Val Gly Arg Leu Leu Asp Tyr Leu Lys Lys Ile
        275                 280                 285

Gly Glu Leu Asp Asn Thr Ile Ile Val Tyr Thr Ser Asp Gln Gly Phe
    290                 295                 300

Tyr Leu Gly Glu His Gly Trp Phe Asp Lys Arg Phe Met Tyr Glu Glu
305                 310                 315                 320

Ser Leu Arg Thr Pro Leu Ile Val Arg Tyr Pro Lys Ala Ile Lys Ala
                325                 330                 335

Gly Ser Val Ser Ala Phe Asn Ile Asp Phe Ala Pro Thr Leu Leu Asp
            340                 345                 350

Val Ala Gly Val Thr Val Pro Asp Met Gln Gly Ser Leu Leu Pro Val
        355                 360                 365

Leu Asp Asn Gly Lys Thr Pro Ala Asp Trp Arg Lys Ala Val Tyr Tyr
    370                 375                 380

His Tyr Tyr Glu Tyr Pro Ala Glu His Val Lys Arg His Tyr Gly Ile
```

```
                385                 390                 395                 400
Arg Thr Glu Arg Tyr Lys Leu Ile His Phe Tyr Asn Asp Ile Asp Glu
                405                 410                 415

Trp Glu Leu Tyr Asp Met Gln Asp Pro Glu Met Asn Asn Leu Tyr Gly
                420                 425                 430

Lys Lys Gly Tyr Glu Lys Ile Lys Glu Leu Lys Leu Lys Glu Gln Lys
                435                 440                 445

Gln Lys Asp Asp Pro Glu
    450

<210> SEQ ID NO 22
<211> LENGTH: 455
<212> TYPE: PRT
<213> ORGANISM: Bacteroides

<400> SEQUENCE: 22

Met Asn Arg Leu Phe Leu Ser Val Ser Val Ala Leu Ser Ala Thr Thr
1               5                   10                  15

Cys Ser Phe Ala Gln Gln Ile Thr Gln Pro Asn Leu Val Leu Phe Ile
                20                  25                  30

Ala Asp Asp Cys Ser Tyr Tyr Asp Leu Gly Cys Tyr Gly Ser Val Asp
                35                  40                  45

Ser Lys Thr Pro Asn Ile Asp Asn Phe Ala Thr Gln Gly Val Arg Phe
50                  55                  60

Thr Gln Ala Tyr Gln Ala Ala Pro Met Ser Ser Pro Thr Arg His Asn
65                  70                  75                  80

Leu Tyr Thr Gly Leu Trp Pro Val Gly Ser Gly Ala Tyr Pro Asn His
                85                  90                  95

Thr Cys Ala Asp Gln Gly Thr Leu Ser Val Val His His Leu His Pro
                100                 105                 110

Leu Gly Tyr Lys Val Ala Leu Ile Gly Lys Lys His Val Ala Pro Lys
                115                 120                 125

Ser Val Phe Pro Phe Asp Leu Tyr Val Pro Ser Glu Lys Gly Glu Leu
130                 135                 140

His Phe Glu Ala Ile Gln Lys Phe Ile Ala Asp Cys Lys Arg Lys Gly
145                 150                 155                 160

Gln Pro Phe Cys Leu Phe Val Ala Ser Asn Gln Pro His Thr Pro Trp
                165                 170                 175

Asn Lys Gly Asp Val Ser Gln Phe Asp Pro Asp Lys Leu Thr Leu Ala
                180                 185                 190

Pro Met Tyr Val Asp Val Pro Gln Thr Arg Gln Glu Phe Thr Lys Tyr
                195                 200                 205

Leu Ala Glu Val Asn Phe Met Asp Gln Glu Phe Gly Asn Val Leu Ser
210                 215                 220

Ile Leu Glu Gln Glu Lys Val Ala Asp Gln Ser Val Val Tyr Leu
225                 230                 235                 240

Ser Glu Gln Gly Asn Ser Leu Pro Phe Ala Lys Trp Thr Cys Tyr Asp
                245                 250                 255

Ala Gly Val His Ser Ala Cys Ile Val Arg Trp Pro Gly Val Val Lys
                260                 265                 270

Pro Gly Ser Val Ser Asp Ala Leu Val Glu Tyr Val Asp Ile Val Pro
                275                 280                 285

Thr Phe Val Asp Ile Ala Gly Gly Lys Pro Gln Thr Arg Val Asp Gly
                290                 295                 300
```

```
Glu Ser Phe Lys Ser Val Leu Thr Gly Lys Lys Glu His Lys Lys
305                 310                 315                 320

Tyr Ser Phe Ser Leu Gln Thr Ser Arg Gly Ile Asn Lys Gly Pro Glu
            325                 330                 335

Tyr Tyr Gly Ile Arg Ser Ala Tyr Asp Gly Arg Tyr Arg Tyr Ile Val
            340                 345                 350

Asn Leu Thr Pro Glu Ala Thr Phe Gln Asn Ala Met Thr Ala Thr Pro
            355                 360                 365

Leu Phe Lys Glu Trp Lys Gln Leu Ala Glu Thr Asp Ala His Ala Lys
            370                 375                 380

Ala Met Thr Phe Lys Tyr Gln His Arg Pro Ala Ile Glu Leu Tyr Asp
385                 390                 395                 400

Val Arg Asn Asp Pro Phe Cys Met Asn Asn Leu Ala Gly Asp Thr Lys
            405                 410                 415

Tyr Ser Asn Ile Ile Ile Arg Leu Asp Ala Glu Leu Lys Lys Trp Met
            420                 425                 430

Lys Ala Cys Gly Asp Glu Gly Gln Ala Thr Glu Met Arg Ala Phe Asp
            435                 440                 445

His Met Pro Ser Lys Gln Lys
            450                 455

<210> SEQ ID NO 23
<211> LENGTH: 393
<212> TYPE: PRT
<213> ORGANISM: Artificial Sequence
<220> FEATURE:
<223> OTHER INFORMATION: Consensus Sequence

<400> SEQUENCE: 23

Leu Val Pro Ala Leu Leu Leu Val Leu Thr Leu Cys Thr Ala Asp
1               5                   10                  15

Arg Pro Asn Val Leu Leu Ile Ile Asp Asp Gln Ser Phe His Val Gly
                20                  25                  30

Ala Tyr Gly Gln Ala Ile Arg Thr Pro Asn Met Asp Arg Val Ala Lys
            35                  40                  45

Gly Val Phe Thr Asn Ala Phe Thr Ser Ser Pro Ser Cys Ser Pro Ser
        50                  55                  60

Arg Ala Ala Leu Leu Thr Gly Leu Ile Trp Gln Ile Tyr Gly Asn His
65                  70                  75                  80

Val Lys Tyr Lys Tyr Pro Asp Leu Leu Glu Asn Ala Gly Tyr Arg Val
                85                  90                  95

Gly Ile Gly Lys Lys Gly Pro Gly Ser Val Tyr Pro Phe Asp Arg Arg
            100                 105                 110

Asn Pro Gly Gly Phe Ser Tyr Ala Leu Phe Arg Phe Leu Lys Lys Lys
        115                 120                 125

Asp Lys Pro Phe Cys Leu Trp Val Ala Ser His Glu Pro His Arg Pro
130                 135                 140

Phe Lys Gly Gly Glu Lys Asn Gly Asp Pro Lys Val Val Pro Ala
145                 150                 155                 160

Phe Leu Pro Asp Thr Pro Ile Arg Asp Ile Ala Asp Tyr Tyr Ala Glu
        165                 170                 175

Val Gln Trp Asp Gln Glu Leu Gly Val Leu Asp Leu Glu Ala Gly Leu
            180                 185                 190

Asp Asn Thr Val Val Ile Val Thr Ser Asp Asn Gly Met Phe Pro Arg
            195                 200                 205
```

```
Ala Lys Ala Asn Leu Tyr Asp Tyr Gly Thr His Met Pro Leu Ile Ile
    210                 215                 220

Ser Trp Pro Gly Lys Gly Val Ser Asp Ala Leu Val Thr Leu Ile Asp
225                 230                 235                 240

Leu Thr Pro Thr Leu Asp Leu Gly Val Pro Pro Leu Ser Gly Lys
            245                 250                 255

Ser Leu Val Leu Leu Arg Ser Gly Ile Asp Glu Lys Pro Arg Asp Ala
        260                 265                 270

Val Val Phe Gly Arg Arg His Val Arg Arg Leu Gly Tyr Pro Met Arg
            275                 280                 285

Ser Ile Arg Thr Lys Tyr Tyr Ile Arg Asn Leu Pro Glu Arg Trp Ala
    290                 295                 300

Gly Pro Phe Tyr Gly Glu Leu Pro Tyr Val Ser Pro Thr Phe Phe Leu
305                 310                 315                 320

Val Glu Arg Asp Asp Ala Lys Leu Ser Phe Phe Ala Val Ala Lys Arg
            325                 330                 335

Pro Ala Asp Glu Leu Tyr Asp Ile Gln Lys Pro Leu Asn Asn Leu
        340                 345                 350

Ala Ala Asp Pro Phe Ala Gln Ile Lys Leu Ala Arg Leu Arg Lys Tyr
    355                 360                 365

Leu Ala Thr Asp Pro Arg Ser Pro Asp Gly Ile Ile Trp Asp Thr Pro
370                 375                 380

Tyr Leu Pro Pro Lys Arg Leu Glu Val
385                 390

<210> SEQ ID NO 24
<211> LENGTH: 533
<212> TYPE: PRT
<213> ORGANISM: Homo sapiens

<400> SEQUENCE: 24

Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
            85                  90                  95

Gln Leu Leu Thr Gly Arg Tyr Gln Ile Arg Thr Gly Leu Gln His Gln
        100                 105                 110

Ile Ile Trp Pro Cys Gln Pro Ser Cys Val Pro Leu Asp Glu Lys Leu
    115                 120                 125

Leu Pro Gln Leu Leu Lys Glu Ala Gly Tyr Thr Thr His Met Val Gly
130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
            165                 170                 175

Ser His Glu Arg Cys Thr Leu Ile Asp Ala Leu Asn Val Thr Arg Cys
        180                 185                 190
```

```
Ala Leu Asp Phe Arg Asp Gly Glu Glu Val Ala Thr Gly Tyr Lys Asn
            195                 200                 205

Met Tyr Ser Thr Asn Ile Phe Thr Lys Arg Ala Ile Ala Leu Ile Thr
210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Tyr Leu Lys Pro Tyr Asp
            245                 250                 255

Phe Ile Gln Asp Lys Asn Arg His His Tyr Ala Gly Met Val Ser Leu
                260                 265                 270

Met Asp Glu Ala Val Gly Asn Val Thr Ala Ala Leu Lys Ser Ser Gly
            275                 280                 285

Leu Trp Asn Asn Thr Val Phe Ile Phe Ser Thr Asp Asn Gly Gly Gln
290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
            340                 345                 350

Trp Leu Pro Thr Leu Val Lys Leu Ala Arg Gly His Thr Asn Gly Thr
                355                 360                 365

Lys Pro Leu Asp Gly Phe Asp Val Trp Lys Thr Ile Ser Glu Gly Ser
            370                 375                 380

Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
                405                 410                 415

Ser Ser Leu Pro Glu Tyr Ser Ala Phe Asn Thr Ser Val His Ala Ala
            420                 425                 430

Ile Arg His Gly Asn Trp Lys Leu Leu Thr Gly Tyr Pro Gly Cys Gly
                435                 440                 445

Tyr Trp Phe Pro Pro Ser Gln Tyr Asn Val Ser Glu Ile Pro Ser
450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
                485                 490                 495

Lys Leu Leu Ser Arg Leu Gln Phe Tyr His Lys His Ser Val Pro Val
            500                 505                 510

Tyr Phe Pro Ala Gln Asp Pro Arg Cys Asp Pro Lys Ala Thr Gly Val
            515                 520                 525

Trp Gly Pro Trp Met
    530

<210> SEQ ID NO 25
<211> LENGTH: 509
<212> TYPE: PRT
<213> ORGANISM: Homo sapiens

<400> SEQUENCE: 25

Met Ser Met Gly Ala Pro Arg Ser Leu Leu Leu Ala Leu Ala Ala Gly
1               5                   10                  15

Leu Ala Val Ala Arg Pro Pro Asn Ile Val Leu Ile Phe Ala Asp Asp
```

```
            20                  25                  30
Leu Gly Tyr Gly Asp Leu Gly Cys Tyr Gly His Pro Ser Ser Thr Thr
            35                  40                  45
Pro Asn Leu Asp Gln Leu Ala Ala Gly Gly Leu Arg Phe Thr Asp Phe
            50                  55                  60
Tyr Val Pro Val Ser Leu Cys Thr Pro Ser Arg Ala Ala Leu Leu Thr
 65                  70                  75                  80
Gly Arg Leu Pro Val Arg Met Gly Met Tyr Pro Gly Val Leu Val Pro
                    85                  90                  95
Ser Ser Arg Gly Gly Leu Pro Leu Glu Glu Val Thr Val Ala Glu Val
                   100                 105                 110
Leu Ala Ala Arg Gly Tyr Leu Thr Gly Met Ala Gly Lys Trp His Leu
                   115                 120                 125
Gly Val Gly Pro Glu Gly Ala Phe Leu Pro Pro His Gln Gly Phe His
                   130                 135                 140
Arg Phe Leu Gly Ile Pro Tyr Ser His Asp Gln Gly Pro Cys Gln Asn
145                 150                 155                 160
Leu Thr Cys Phe Pro Pro Ala Thr Pro Cys Asp Gly Cys Asp Gln
                   165                 170                 175
Gly Leu Val Pro Ile Pro Leu Leu Ala Asn Leu Ser Val Glu Ala Gln
                   180                 185                 190
Pro Pro Trp Leu Pro Gly Leu Glu Ala Arg Tyr Met Ala Phe Ala His
                   195                 200                 205
Asp Leu Met Ala Asp Ala Gln Arg Gln Asp Arg Pro Phe Phe Leu Tyr
                   210                 215                 220
Tyr Ala Ser His His Thr His Tyr Pro Gln Phe Ser Gly Gln Ser Phe
225                 230                 235                 240
Ala Glu Arg Ser Gly Arg Gly Pro Phe Gly Asp Ser Leu Met Glu Leu
                   245                 250                 255
Asp Ala Ala Val Gly Thr Leu Met Thr Ala Ile Gly Asp Leu Gly Leu
                   260                 265                 270
Leu Glu Glu Thr Leu Val Ile Phe Thr Ala Asp Asn Gly Pro Glu Thr
                   275                 280                 285
Met Arg Met Ser Arg Gly Gly Cys Ser Gly Leu Leu Arg Cys Gly Lys
                   290                 295                 300
Gly Thr Thr Tyr Glu Gly Gly Val Arg Glu Pro Ala Leu Ala Phe Trp
305                 310                 315                 320
Pro Gly His Ile Ala Pro Gly Val Thr His Glu Leu Ala Ser Ser Leu
                   325                 330                 335
Asp Leu Leu Pro Thr Leu Ala Ala Leu Ala Gly Ala Pro Leu Pro Asn
                   340                 345                 350
Val Thr Leu Asp Gly Phe Asp Leu Ser Pro Leu Leu Leu Gly Thr Gly
                   355                 360                 365
Lys Ser Pro Arg Gln Ser Leu Phe Phe Tyr Pro Ser Tyr Pro Asp Glu
                   370                 375                 380
Val Arg Gly Val Phe Ala Val Arg Thr Gly Lys Tyr Lys Ala His Phe
385                 390                 395                 400
Phe Thr Gln Gly Ser Ala His Ser Asp Thr Thr Ala Asp Pro Ala Cys
                   405                 410                 415
His Ala Ser Ser Ser Leu Thr Ala His Glu Pro Pro Leu Leu Tyr Asp
                   420                 425                 430
Leu Ser Lys Asp Pro Gly Glu Asn Tyr Asn Leu Leu Gly Gly Val Ala
                   435                 440                 445
```

```
Gly Ala Thr Pro Glu Val Leu Gln Ala Leu Lys Gln Leu Gln Leu Leu
        450                 455                 460

Lys Ala Gln Leu Asp Ala Ala Val Thr Phe Gly Pro Ser Gln Val Ala
465                 470                 475                 480

Lys Gly Glu Asp Pro Ala Leu Gln Ile Cys Cys His Pro Gly Cys Thr
                485                 490                 495

Pro Arg Pro Ala Cys Cys His Cys Pro Asp Pro His Ala
            500                 505
```

<210> SEQ ID NO 26
<211> LENGTH: 536
<212> TYPE: PRT
<213> ORGANISM: Pseudomonas aeruginosa

<400> SEQUENCE: 26

```
Met Ser Lys Arg Pro Asn Phe Leu Val Ile Val Ala Asp Asp Leu Gly
1               5                   10                  15

Phe Ser Asp Ile Gly Ala Phe Gly Gly Glu Ile Ala Thr Pro Asn Leu
            20                  25                  30

Asp Ala Leu Ala Ile Ala Gly Leu Arg Leu Thr Asp Phe His Thr Ala
        35                  40                  45

Ser Thr Cys Ser Pro Thr Arg Ser Met Leu Leu Thr Gly Thr Asp His
    50                  55                  60

His Ile Ala Gly Ile Gly Thr Met Ala Glu Ala Leu Thr Pro Glu Leu
65                  70                  75                  80

Glu Gly Lys Pro Gly Tyr Glu Gly His Leu Asn Glu Arg Val Val Ala
                85                  90                  95

Leu Pro Glu Leu Leu Arg Glu Ala Gly Tyr Gln Thr Leu Met Ala Gly
            100                 105                 110

Lys Trp His Leu Gly Leu Lys Pro Glu Gln Thr Pro His Ala Arg Gly
        115                 120                 125

Phe Glu Arg Ser Phe Ser Leu Leu Pro Gly Ala Ala Asn His Tyr Gly
    130                 135                 140

Phe Glu Pro Pro Tyr Asp Glu Ser Thr Pro Arg Ile Leu Lys Gly Thr
145                 150                 155                 160

Pro Ala Leu Tyr Val Glu Asp Glu Arg Tyr Leu Asp Thr Leu Pro Glu
                165                 170                 175

Gly Phe Tyr Ser Ser Asp Ala Phe Gly Asp Lys Leu Leu Gln Tyr Leu
            180                 185                 190

Lys Glu Arg Asp Gln Ser Arg Pro Phe Phe Ala Tyr Leu Pro Phe Ser
        195                 200                 205

Ala Pro His Trp Pro Leu Gln Ala Pro Arg Glu Ile Val Glu Lys Tyr
    210                 215                 220

Arg Gly Arg Tyr Asp Ala Gly Pro Glu Ala Leu Arg Gln Glu Arg Leu
225                 230                 235                 240

Ala Arg Leu Lys Glu Leu Gly Leu Val Glu Ala Asp Val Glu Ala His
                245                 250                 255

Pro Val Leu Ala Leu Thr Arg Glu Trp Glu Ala Leu Glu Asp Glu Glu
            260                 265                 270

Arg Ala Lys Ser Ala Arg Ala Met Glu Val Tyr Ala Ala Met Val Glu
        275                 280                 285

Arg Met Asp Trp Asn Ile Gly Arg Val Val Asp Tyr Leu Arg Arg Gln
    290                 295                 300

Gly Glu Leu Asp Asn Thr Phe Val Leu Phe Met Ser Asp Asn Gly Ala
```

```
            305                 310                 315                 320
        Glu Gly Ala Leu Leu Glu Ala Phe Pro Lys Phe Gly Pro Asp Leu Leu
                        325                 330                 335

Gly Phe Leu Asp Arg His Tyr Asp Asn Ser Leu Glu Asn Ile Gly Arg
                        340                 345                 350

Ala Asn Ser Tyr Val Trp Tyr Gly Pro Arg Trp Ala Gln Ala Ala Thr
                        355                 360                 365

Ala Pro Ser Arg Leu Tyr Lys Ala Phe Thr Thr Gln Gly Gly Ile Arg
                        370                 375                 380

Val Pro Ala Leu Val Arg Tyr Pro Arg Leu Ser Arg Gln Gly Ala Ile
        385                 390                 395                 400

Ser His Ala Phe Ala Thr Val Met Asp Val Thr Pro Thr Leu Leu Asp
                        405                 410                 415

Leu Ala Gly Val Arg His Pro Gly Lys Arg Trp Arg Gly Arg Glu Ile
                        420                 425                 430

Ala Glu Pro Arg Gly Arg Ser Trp Leu Gly Trp Leu Ser Gly Glu Thr
                        435                 440                 445

Glu Ala Ala His Asp Glu Asn Thr Val Thr Gly Trp Glu Leu Phe Gly
                        450                 455                 460

Met Arg Ala Ile Arg Gln Gly Asp Trp Lys Ala Val Tyr Leu Pro Ala
        465                 470                 475                 480

Pro Val Gly Pro Ala Thr Trp Gln Leu Tyr Asp Leu Ala Arg Asp Pro
                        485                 490                 495

Gly Glu Ile His Asp Leu Ala Asp Ser Gln Pro Gly Lys Leu Ala Glu
                        500                 505                 510

Leu Ile Glu His Trp Lys Arg Tyr Val Ser Glu Thr Gly Val Val Glu
                        515                 520                 525

Gly Ala Ser Pro Phe Leu Val Arg
                        530                 535

<210> SEQ ID NO 27
<211> LENGTH: 205
<212> TYPE: PRT
<213> ORGANISM: Artificial Sequence
<220> FEATURE:
<223> OTHER INFORMATION: Consensus sequence

<400> SEQUENCE: 27

Leu Leu Val Leu Leu Ala Ser Arg Arg Pro Asn Ile Val Leu Ile
        1               5                   10                  15

Leu Ala Asp Asp Leu Gly Trp Asn Asp Val Gly Tyr Gly Ile Arg Thr
                        20                  25                  30

Pro Asn Leu Asp Leu Ala Gly Gly Val Arg Phe Thr Asn Tyr Tyr Leu
                        35                  40                  45

Cys Thr Pro Ser Arg Ala Leu Leu Thr Gly Arg Tyr Ile Gly Leu Ile
                        50                  55                  60

Val Pro Val Leu Val Leu Leu Pro Glu Leu Leu Lys Glu Ala Gly Tyr
        65                  70                  75                  80

Thr Gly Met Gly Lys Trp His Leu Gly Met Pro Pro Gly Phe Asp Tyr
                        85                  90                  95

Phe Ile Leu Gln Tyr Asp Val Lys Asp Glu Tyr Ile Pro Arg Pro Phe
                        100                 105                 110

Phe Tyr Ala His Glu Pro Gln Val Glu Asp Tyr Val Asp Val Gly Val
                        115                 120                 125

Leu Gly Leu Leu Thr Val Ile Asp Asn Gly Gln Ala Leu Gly Lys Trp
```

-continued

```
            130                 135                 140
Glu Val Phe Gly Val Leu Asp Trp Leu Pro Leu Val Leu Ala Leu Gly
145                     150                 155                 160

Asp Ser Leu Ile Ala Asp Phe Val Val Arg Pro Arg Gly Phe Thr Ser
                165                 170                 175

Val Ala Ile Arg His Lys Leu Ala Tyr Val Lys Asp Pro Asn Trp Arg
                180                 185                 190

Lys Leu Leu Thr Phe Leu Val Lys Val Ile Pro Gly Pro
        195                 200                 205
```